US010001483B2

(12) United States Patent
Yarchoan et al.

(10) Patent No.: US 10,001,483 B2
(45) Date of Patent: Jun. 19, 2018

(54) METHODS FOR THE TREATMENT OF KAPOSI'S SARCOMA OR KSHV-INDUCED LYMPHOMA USING IMMUNOMODULATORY COMPOUNDS, AND USES OF BIOMARKERS

(71) Applicants: Celgene Corporation, Summit, NJ (US); The United States of America, as represented by the Secretary, Department of Health and Human Services, Office of Technology Transfer, National Institutes of Health, Washington, DC (US)

(72) Inventors: Robert Yarchoan, Bethesda, MD (US); Jerome B. Zeldis, Princeton, NJ (US); Mark N. Polizzotto, New South Wales (AU); David A. Davis, Bethesda, MD (US); Irini Sereti, Washington, DC (US); Thomas S. Uldrick, Washington, DC (US); Denise Whitby, Frederick, MD (US); Vikram Khetani, Short Hills, NJ (US)

(73) Assignees: Celgene Corporation, Summit, NJ (US); The United States of America, as Represented by the Secretary, Department of Health and Human Services, Washington, DC (US)

( * ) Notice: Subject to any disclaimer, the term of this patent is extended or adjusted under 35 U.S.C. 154(b) by 0 days. days.

(21) Appl. No.: 15/192,819

(22) Filed: Jun. 24, 2016

(65) Prior Publication Data
US 2016/0377621 A1    Dec. 29, 2016

Related U.S. Application Data

(60) Provisional application No. 62/185,265, filed on Jun. 26, 2015.

(51) Int. Cl.
| | |
|---|---|
| *A61K 31/40* | (2006.01) |
| *G01N 33/574* | (2006.01) |
| *A61K 31/454* | (2006.01) |
| *A61K 45/06* | (2006.01) |
| *A61K 31/704* | (2006.01) |
| *A61K 31/4035* | (2006.01) |

(52) U.S. Cl.
CPC ..... *G01N 33/57407* (2013.01); *A61K 31/454* (2013.01); *A61K 31/704* (2013.01); *A61K 45/06* (2013.01); *A61K 31/4035* (2013.01); *G01N 2333/70539* (2013.01); *G01N 2800/52* (2013.01)

(58) Field of Classification Search
CPC .................................................. A61K 31/4035
USPC ...................................................... 514/416
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni et al. | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,810,643 A | 3/1989 | Souza | |
| 4,999,291 A | 3/1991 | Souza | |
| 5,059,595 A | 10/1991 | Le Grazie | |
| 5,073,543 A | 12/1991 | Marshall et al. | |
| 5,120,548 A | 6/1992 | McClelland et al. | |
| 5,134,127 A | 7/1992 | Stella et al. | |
| 5,229,496 A | 7/1993 | Deeley et al. | |
| 5,354,556 A | 10/1994 | Sparks et al. | |
| 5,385,901 A | 1/1995 | Kaplan et al. | |
| 5,391,485 A | 2/1995 | Deeley et al. | |
| 5,393,870 A | 2/1995 | Deeley et al. | |
| 5,528,823 A | 6/1996 | Rudy, Jr. et al. | |
| 5,580,755 A | 12/1996 | Souza | |
| 5,591,767 A | 1/1997 | Mohr et al. | |
| 5,593,990 A | 1/1997 | D'Amato | |
| 5,629,327 A | 5/1997 | D'Amato | |
| 5,635,517 A | 6/1997 | Muller et al. | |
| 5,639,476 A | 6/1997 | Oshlack et al. | |
| 5,674,533 A | 10/1997 | Santus et al. | |
| 5,698,579 A | 12/1997 | Muller | |
| 5,712,291 A | 1/1998 | D'Amato | |
| 5,731,325 A | 3/1998 | Andrulis, Jr. et al. | |
| 5,733,566 A | 3/1998 | Lewis | |

(Continued)

FOREIGN PATENT DOCUMENTS

| | | |
|---|---|---|
| WO | WO 92/014455 | 9/1992 |
| WO | WO 94/020085 | 9/1994 |

(Continued)

OTHER PUBLICATIONS

"Celgene drug promises activity in solid tumors," Marketletter, Jun. 18, 2001.
"List of Approved Oncology Drugs with Approved Indications," http://www.accessdata.fda.gov/scripts/cder/onctools/druglist.cfm, last accessed on Sep. 11, 2008.
Alexanian et al., 2004, "VTD (Velcade, thalidomide, dexamethasone) as primary therapy for newly-diagnosed multiple myeloma," Am. Soc. Hematol. 46th Ann. Meeting Dec. 4-7, 2004, San Diego, CA Abstract #210.

(Continued)

*Primary Examiner* — Kevin E Weddington
(74) *Attorney, Agent, or Firm* — Jones Day

(57) ABSTRACT

Provided herein are uses of gene and protein biomarkers as a predictor of clinical sensitivity of Kaposi's sarcoma (KS) or Kaposi's sarcoma-associated herpesvirus (KSHV) induced lymphoma and patient response to treatment with an immunomodulatory compound. Further provided herein are methods for the treatment or management of Kaposi's sarcoma or KSHV-induced lymphoma with an immunomodulatory compound, alone or in combination with doxorubicin.

29 Claims, 16 Drawing Sheets

(56) References Cited

U.S. PATENT DOCUMENTS

| | | |
|---|---|---|
| 5,798,368 A | 8/1998 | Muller et al. |
| 5,874,448 A | 2/1999 | Muller et al. |
| 5,877,200 A | 3/1999 | Muller |
| 5,929,117 A | 7/1999 | Muller et al. |
| 5,955,476 A | 9/1999 | Muller et al. |
| 6,020,358 A | 2/2000 | Muller et al. |
| 6,071,948 A | 6/2000 | D'Amato |
| 6,114,355 A | 9/2000 | D'Amato |
| 6,140,346 A | 10/2000 | Andrulis, Jr. et al. |
| 6,228,879 B1 | 5/2001 | Green et al. |
| 6,235,756 B1 | 5/2001 | D'Amato |
| 6,281,230 B1 | 8/2001 | Muller et al. |
| 6,316,471 B1 | 11/2001 | Muller et al. |
| 6,326,388 B1 | 12/2001 | Man et al. |
| 6,335,349 B1 | 1/2002 | Muller et al. |
| 6,380,239 B1 | 4/2002 | Muller et al. |
| 6,395,754 B1 | 5/2002 | Muller et al. |
| 6,403,613 B1 | 6/2002 | Man et al. |
| 6,420,414 B1 | 7/2002 | D'Amato |
| 6,458,810 B1 | 10/2002 | Muller et al. |
| 6,469,045 B1 | 10/2002 | D'Amato |
| 6,476,052 B1 | 11/2002 | Muller et al. |
| 6,518,298 B2 | 2/2003 | Green et al. |
| 6,555,554 B2 | 4/2003 | Muller et al. |
| 6,673,828 B1 | 1/2004 | Green et al. |
| 7,112,602 B2 | 9/2006 | D'Amato et al. |
| 7,323,479 B2 | 1/2008 | Zeldis |
| 7,393,862 B2 | 7/2008 | Zeldis |
| 7,435,745 B2 | 10/2008 | D'Amato |
| 7,468,363 B2 | 12/2008 | Zeldis |
| 7,968,569 B2 | 6/2011 | Zeldis |
| 8,198,262 B2 | 6/2012 | Zeldis |
| 8,722,647 B2 | 5/2014 | Zeldis |
| 9,050,324 B2 | 6/2015 | Zeldis |
| 2001/0018445 A1 | 8/2001 | Huang et al. |
| 2001/0056114 A1 | 12/2001 | D'Amato |
| 2002/0035090 A1 | 3/2002 | Zeldis et al. |
| 2002/0045643 A1 | 4/2002 | Muller et al. |
| 2002/0052398 A1 | 5/2002 | D'Amato |
| 2002/0054899 A1 | 5/2002 | Zeldis |
| 2002/0061923 A1 | 5/2002 | D'Amato |
| 2002/0128228 A1 | 9/2002 | Hwu |
| 2002/0161023 A1 | 10/2002 | D'Amato |
| 2002/0173658 A1 | 11/2002 | Muller et al. |
| 2002/0183360 A1 | 12/2002 | Muller et al. |
| 2003/0013739 A1 | 1/2003 | Masferrer et al. |
| 2003/0028028 A1 | 2/2003 | Man et al. |
| 2003/0045552 A1 | 3/2003 | Robarge et al. |
| 2003/0069428 A1 | 4/2003 | Muller et al. |
| 2003/0096841 A1 | 5/2003 | Robarge et al. |
| 2003/0139451 A1 | 7/2003 | Shah et al. |
| 2003/0144325 A1 | 7/2003 | Muller et al. |
| 2003/0181428 A1 | 9/2003 | Green et al. |
| 2003/0187024 A1 | 10/2003 | D'Amato |
| 2003/0191098 A1 | 10/2003 | D'Amato |
| 2003/0235909 A1 | 12/2003 | Hariri et al. |
| 2004/0029832 A1 | 2/2004 | Zeldis |
| 2004/0077685 A1 | 4/2004 | Figg et al. |
| 2004/0077686 A1 | 4/2004 | Dannenberg et al. |
| 2004/0087546 A1 | 5/2004 | Zeldis |
| 2004/0091455 A1 | 5/2004 | Zeldis |
| 2004/0122052 A1 | 6/2004 | Muller et al. |
| 2004/0266809 A1 | 12/2004 | Emanuel et al. |
| 2008/0145368 A1 | 6/2008 | Zeldis |
| 2008/0292583 A1 | 11/2008 | Zeldis |
| 2008/0317708 A1 | 12/2008 | Zeldis |
| 2009/0010877 A1 | 1/2009 | Zeldis |
| 2009/0123416 A1 | 5/2009 | Zeldis |
| 2009/0155265 A1 | 6/2009 | Zeldis |
| 2010/0093683 A1 | 4/2010 | Zeldis |
| 2010/0196369 A1 | 8/2010 | Zeldis |
| 2010/0260719 A1 | 10/2010 | Zeldis |
| 2013/0224201 A1 | 8/2013 | Garcia-Martinez et al. |
| 2014/0142102 A1 | 5/2014 | Fairfax et al. |
| 2015/0190386 A1 | 7/2015 | Zeldis |

FOREIGN PATENT DOCUMENTS

| | | | |
|---|---|---|---|
| WO | WO 98/003502 | 1/1998 | |
| WO | WO 98/054170 | 12/1998 | |
| WO | WO 01/070275 | 9/2001 | |
| WO | WO 01/087307 | 11/2001 | |
| WO | WO 02/015926 | 2/2002 | |
| WO | WO 02/059106 | 8/2002 | |
| WO | WO 02/064083 | 8/2002 | |
| WO | WO 03/086373 | 10/2003 | |
| WO | WO 2004103274 A2 * | 12/2004 | ............ A61K 31/00 |
| WO | 2015/002754 A2 | 1/2015 | |

OTHER PUBLICATIONS

Alexanian, R. et al., "Primary Dexamethasone Treatment of Multiple Myeloma," *Blood*, 1992, 80(4):887-890.

Anderson, "Moving disease biology from the laboratory to the clinic," *Seminars in Oncology*, 2002 29:17-20.

Anderson, "The Role of Immunomodulatory Drugs in Multiple Myeloma," *Seminars in Hematology*, vol. 40, No. 4, Suppl 4, 2003: pp. 23-32.

Anderson, 2000, "Thalidomide: Therapeutic potential in hematologic malignancies," Seminars in Hematology 37(1 Supp 3): 1-4.

Attal et al., 2004, "Maintenance treatment with thalidomide after autologous transplantation for myeloma: First analysis of a prospective randomized study of the Intergroupe Francophone du Myeloma (IFM 99 02)," Am. Soc. Hematol. 46$^{th}$ Ann. Meeting Dec. 4-7, 2004, San Diego, CA Abstract #535.

Bach, 1963, "Studies on the Possible Anti-Neoplastic Effect of Thalidomide," *Acta Pathologica Et Microbiologica Scandinavica* 59:491-499.

Bach, 1963, "Thalidomide in Cancer Chemotherapy," *The Lancet*, No. 1271, p. 71.

Barlogie et al., "High-dose therapy immunomodulatory drugs in multiple myeloma," *Seminars in Oncology*, 2002, 29 (6):26-33.

Barlogie et al., "Introduction: Thalidomide and the IMiDs in multiple myeloma," *Seminars in Hematology*, 2003, 40 (4):1-2.

Barlogie et al., "Total Therapy II (TTII) for newly diagnosed multiple myeloma (MM): preliminary data on feasibility and efficacy in the first 231 enrolled patients; comparison with predecessor trial total therapy I ((TTI) (N=231)," *Blood*, Abstract # 2857, Dec. 7-11, 2001, *American Society of Hematology*.

Barlogie, "Thalidomide and CC-5013 in Multiple Myeloma: The University of Arkansas experience," *Seminars in Hematology*, 2003, 40 (4):33-38.

Barlogie, B. et al., "Effective Treatment of Advanced Multiple Myeloma Refractory to Alkylating Agents," *N. Engl. J. Med.*, 1984, 310(21):1353-1356.

Barlogie, B., Desikan, R., Munshi, N., Siegel, D., Mehta, J., Singhal, S., Anaissie, E., Single Course D.T. Pace Anti-Angiochemotherapy Effects CR in Plasma Cell Leukemia and Fulminant Multiple Myeloma (MM). Abstract #4180. American Society of Hematology, Dec. 4-9, 1998.

Bartlett et al., "Phase I study to determine the safety, tolerability and immunostimulatory activity of thalidomide analogue CC-5013 in patients with metastatic malignant melanoma and other advanced cancers," *British Journal of Cancer*, 2004, 90:955-961.

Bartlett et al., "The evolution of thalidomide and its IMiD derivatives as anticancer agents," *Nature Reviews Cancer*, 2004, 4 (4):1-9.

Battegay, "Angiogenesis: mechanistic insights, neovascular diseases, and therapeutic prospects," *J. Mol. Med.*, 1995, 73:333-346.

Baz et al., "Doxil (D), vincristine (V), reduced frequency dexamethasone (d) and revlimid (R) (DVd-R) results in a high response rate in patients with refractory multiple myeloma (RMM)," *Blood*, Abstract # 2559, *American Society of Hematology*, Dec. 10-13, 2005.

Berenson, J. R. et al., "Long-Term Pamidronate Treatment of Advanced Multiple Myeloma Patients Reduces Skeletal Events," *Journal of Clinical Oncology*, 1998, 16(2):593-602.

Berenson, J.R.; Bergsagel, P. L.; Munshi, N.; Initiation and Maintenance of Multiple Myeloma; Seminars in Hematology, vol. 36, No. 1, Supp. 3, Jan. 1999, pp. 9-13.

(56) References Cited

OTHER PUBLICATIONS

Bernardeschi et al., 2003, J. Exp. Clin. Cancer Res. 22(4):129-133.
Brennen et al., "Thalidomide and analogues: current proposed mechanisms and therapeutic usage," *Clinical Prostate Cancer*, 2004, 3 (1):54-61.
Carstensen, 1995, *Drug Stability: Principles & Practice*, $2^{nd}$. ed., Marcel Dekker, New York, NY pp. 379-380.
Cavanagh, L.L.; Barnetson, R.S.; Basten, A.; Halliday, G.M.; Dendritic Epidermal T-Cell Involvement in Induction of CD8+ T-Cell-Mediated Immunity Against an Ultraviolet Radiation-Induced Skin Tumor Int. J. Cancer: 70, 98-105, 1997.
Celgene Corporation, "Additional clinical data presented on Revimid™ in myelody splastic sydromes at the American Society of Hematology $45^{th}$ annual meeting," Press Release, Dec. 2003.
Celgene Corporation, "Blood reports Revimid™ has anti-tumor activity in patients with relapsed and refractory multiple myeloma," Press Release, Nov. 1, 2002.
Celgene Corporation, "Celgene advances immunomodulatory drug (IMiD™) clinical program," Press Release, Feb. 2000.
Celgene Corporation, "Celgene announces plans to stop phase III trials in melanoma due to lack of efficacy," Press Release, Apr. 2004.
Celgene Corporation, "Celgene corporation advances Actimid™ (CC-4047) into phase II trial for prostate cancer," Press Release, Oct. 2003.
Celgene Corporation, "Celgene Corporation announces fourth quarter and full year results for 2002," Press Release, Jan. 2003.
Celgene Corporation, "Celgene Corporation announces third quarter results. Thalomid® (thalidomide) sales increase 24%. Prescriptions up 50%. Enhanced S.T.E.P.S.® launched. Pilot d-MPH data presented," Press Release, Oct. 2001.
Celgene Corporation, "Celgene Corporation announces third quarter results. Thalomid® (thalidomide) revenue increases 41% to $30.5 million. Pivotal programs for Thalomid and Revimid™ finalized. Peer-reviewed publications of Thalomid and Revimid data. First JNK inhibitor advanced to Phase I clinical trial," Press Release, Oct. 2002.
Celgene Corporation, "Celgene Corporation receives orphan drug designation for Revimid™ for multiple myeloma," Press Release, Oct. 2001.
Celgene Corporation, "Celgene corporation reports record operating performance in third quarter as total revenue increases 117% and profits rise," Press Release, Oct. 2003.
Celgene Corporation, "Celgene corporation reports record operating performance in first quarter with strong revenue growth and profits," Press Release, Apr. 2004.
Celgene Corporation, "Celgene corporation reports strong operating performance in second quarter as total sales increase 100 percent and profits rise," Press Release, Jul. 2003.
Celgene Corporation, "Celgene corporation reviews 2003 achievements and announces 2004 financial outlook," Press Release, Jan. 2004.
Celgene Corporation, "Celgene expands clinical development program for Revimid™. Five additional trials of Revimid initiated in hematological and solid tumor cancers," Press Release, Jun. 2002.
Celgene Corporation, "Celgene provides update on clinical pipeline. Celgene Announces first target indication for Actimid™, CC-8490. SelCID™ program to advance based on results from Phase I/II trial of CC-1088. First JNK inhibitor successfully completes phase I trial," Press Release, Jan. 2003.
Celgene Corporation, "Celgene receives fast track status from FDA for Revimid™ in multiple myloma," Press Release, Feb. 2003.
Celgene Corporation, "Celgene receives fast track status from FDA for Revimid™ in myelodysplastic sydromes," Press Release, Apr. 2003.
Celgene Corporation, "Initial Phase I solid tumor data on Celgene's lead IMiD™, Revimid™," Press Release, Jun. 2001.
Celgene Corporation, "New Revimid™ clinical data shows potential as novel approach to treating myelodysplastic syndromes (MDS)," Press Release, May 2003.
Celgene Corporation, "Revlimid™ receives orphan drug designation from the European commission for multiple myeloma," Press Release, Feb. 2004.
Celgene Corporation, "Revlimid™ receives orphan drug designation from the European commission for myelodysplastic sydromes," Press Release, Mar. 2004.
Celgene Press Release, "Celgene Will Discontinue Phase III Origin® Trial in Previously Untreated Elderly Patients with B-Cell Chronic Lymphocytic Leukemia," published on Celgene Newsroom, http://newsroom.celgene.com on Jul. 18, 2013 at 7:30 am EDT.
Chaundhry, 1966, *Cancer Research*, "Effect of Prednisolone and Thalidomide on Induced Submandibular Gland Tumors in Hamster," 26(part 1)1884-86.
Answer to Complaint filed on Nov. 18, 2010 by Natco Pharma Limited in the U.S. District Court, District of New Jersey.
Complaint for Patent Infringement filed on Oct. 8, 2010 by Celgene Corporation in the U.S. District Court, District of New Jersey against Natco Pharma Limited.
Notice of Allowance from U.S. Appl. No. 11/096,155 dated Jan. 12, 2010.
Notice of Opposition to EP 1 505 973 filed by Strawman Limited dated Dec. 1, 2010.
Notice of Opposition to EP 1 505 973 filed by Synthon B. V. dated Nov. 30, 2010.
Notification letter dated Aug. 30, 2010 from Natco Pharma Limited to Celgene Corporation re: Notification pursuant to § 505(j)(2)(B) of the Federal Food, Drug and Cosmetic Act.
Official Action dated Feb. 10, 2009 in JP Application No. 2004-545192. (English translation provided.)
Official Action in corresponding Canadian Application No. 2,476,983 dated Aug. 21, 2009.
Corral et al., 1999, "Differential cytokine modulation and T cell activation by two distinct classes of thalidomide analogues that are potent inhibitors of TNF-alpha," J. Immunol. 163(1):380-386.
Corral et al., 1999, "Immunomodulation by thalidomide and thalidomide analogues," Ann. Rheum. Dis. 58(Suppl 1):I107-113.
Craig et al., 1967, "Potential anticancer agents. III. 2-phthalimidoaldehydes and derivatives," Potential Anticancer Agents III 10:1071-1073.
D 'Amato et al., 1994, "Thalidomide is an Inhibitor of Angiogenesis", Proc. Natl. Acad. Sci. 91:4082-4085.
D 'Amato et al., 2001, "Mechanism of action of thalidomide and 3-aminothalidomide in multiple myeloma," Semin. Oncol. 28:597-601.
Dalgleish et al., "Thalidomide analogues CC-5013 and CC-4047 induce T cell activation and IL-12 production in patients with both solid tumours and relapsed and refractory multiple myeloma," *British Journal of Cancer*, 2003, 88(Suppl I), S25-S54.
Dalgleish, et al., "New thalidomide analogues; anti-cancer, anti-angiogenic and immunostimulatory," *British Journal of Cancer*, 2001, 85 (1)25.
Davies et al., "Thalidomide (Thal) and immunomodulatory derivatives (IMiDs) augment natural killer (NK) cell cytotoxicity in multiple myeloma(MM))," Abstract # 3617, *American Society of Hematology*, Dec. 1-5, 2000.
Davies et al., "Thalidomide (Thal) and immunomodulatory derivatives (IMiDs) augment natural killer (NK) cell cytotoxicity in multiple myeloma ~MM)," Abstract # P222, *VIIIth International Myeloma Workshop*, May 4-8, 2001.
Davies et al., 2001, "Thalidomide and immunomodulatory derivatives augment natural killer cell cytotoxicity in multiple myeloma," Blood 98(1):210-216.
De et al., 1976, "Hansch analysis for some antineoplastic glutarimides," J. Indian Chem. Soc. L.III: 825-826.
De et al., 1976, "Possible antineoplastic agents: III. Synthesis of 6-alkyl-2-[4'-methoxyphthalimido] and 6-alkyl-3-[3'-4'-dimethoxyphenyl] glutarimides," J. Indian Chem. Soc. I.III:1122-1125.
Dibbs et al., "Thalidomide and thalidomide analogs suppress TNFα secretion by myocytes," Abstract # 1284, *Circulation*, 1998.

(56) References Cited

OTHER PUBLICATIONS

Dimopoulos et al., "Results of thalidomide and IMIDs in multiple myeloma,", Abstract # P12.1.4, *International Multiple Myeloma Workshop*, May 23-27, 2003.

Dimopoulos et al., "Study of lenalidomide plus dexamethasone versus dexamethasone alone in relapsed or refractory multiple myeloma (MM): Results of a phase 3 Study (MM-010),", Abstract # 6, *American Society of Hematology*, Dec. 10-13, 2005.

Dimopoulos et al., "Treatment of plasma cell dyscrasias with thalidomide and its derivatives," *Journal of Clinical Oncology*, Dec. 1, 2003, 21 (23)4444-4454.

Dimopoulos et al., 2004, "Primary treatment with puilsed melphalan, dexamethasone, thalidomide (MDT) for symptomatic patients with multiple myeloma ≥75 years of age," Am. Soc. Hematol. 46th Ann. Meeting Dec. 4-7, 2004, San Diego, CA Abstract #1482.

Dimopoulos, et al., "Long-term follow-up on overall survival from the MM-009 and MM-010 phase III trials of lenalidomide plus dexamethasone in patients with relapsed or refractory multiple myeloma," *Leukemia*, 2009, 231:2147-2152.

Dimopoulos, M. et al., "Thalidomide and dexamethasone combination for refractory multiple myeloma," *Annals of Oncology*, 2001, 12:991-995.

Dipaolo, 1963, "In vitro Test Systems for Cancer Chemotherapy, II. Correlation of in vitro Inhibition of Dehydrogenase and Growth with in vivo Inhibition of Ehrlich Asoites Tumor," *Proceedings of the Society for Experimental Biology & Medicine*, 114:384-387.

Dipaolo, 1963, "Effect of Thalidomide on a Variety of Transplantable Tumors," *Cancer Chemotherapy Reports* No. 29, p. 99-102.

Dipaolo, 1964, "Thalidomide: Effects on Ehrlich Ascites Tumor Cells in vitro" Science 144:1583.

Dredge et al., A costimulatory thalidomide analog enhances the partial anti-tumor immunity of an autologous vaccination in a model of colorectal cancer, Abstract # 491, *American Association for Cancer Research*, Apr. 6-10, 2002.

Dredge et al., "Adjuvants and the promotion of Thl-type cytokines in tumour immunotherapy," *Cancer Immunol. Immunother.*, 2002, 51:521-531.

Dredge et al., "Angiogenesis inhibitors in cancer therapy," *Current Opinion in Investigational Drugs*, 2003, 4(6):667-674.

Dredge et al., "Immunological effects of thalidomide and its chemical and functional analogs," *Critical Reviews in Immunology*, 2002, 22 (5&6):425-437.

Dredge et al., "Protective antitumor immunity induced by a costimulatory thalidomide analog in conjunction with whole tumor cell vaccination is mediated by increased Thl-type immunity[1]," *The Journal of Immunology*, 2002, 168:4914-4919.

Dredge et al., "Recent developments in antiangiogenic therapy," *Expert Opin. Biol. Ther.*, 2002, 2 (8):953-966.

Dredge et al., "Thalidomide analogs as emerging anti-cancer drugs," *Anti-Cancer Drugs*, 2003, 14:331-335.

Dredge et al., 2002, "Novel thalidomide analogues display antiangiogenic activity independently of immunomodulatory effects," Br. J. Cancer 87(10):1166-1172.

Eisen et al., 2000, "Continuous low dose Thalidomide: a phase II study in advanced melanoma, renal cell, ovarian and breast cancer," Br. J. Cancer 82(4):812-817.

English translation of Japanese IP High Court decision in Japanese Application No. 2004-505051, dated Apr. 11, 2013.

Extracts from drug databases: retrieved from http://www.nextbio.com/b/search/ov/IMiD3%20cpd on Nov. 26, 2010 and http://pubchem.ncbi.nlm.nih.gov/summary/summary.cgi?cid=216326 on Nov. 26, 2010.

Fakhouri et al., 2004, "Thalidomide inpatients with multiple myeloma and renal failure," Br. J. Haematol. 125:90-102.

Fenk et al., 2005, "Single-agent thalidomide for treatment of first relapse following high-dose chemotherapy in patients with multiple myeloma," Leukemia 19(1):156-159.

Fernandes, P., "Anti-Cancer Drug Discovery and Development Summit," *IDrugs*, 2002, 5(8):757-764.

Fickentscher et al., "Stereochemical properties and teratogenic activity of some tetrahydrophthalimides," *Molecular Pharmacology*, 1976, 13:133-141.

Figg et al., "Inhibition of angiogenesis: treatment options for patients with metastatic prostate cancer," *Investigational New Drugs*, 2002, 20(2):183-194.

Folkman et al., 1983, "Angiogenesis inhibition and tumor regression caused by heparin or a heparin fragment in the presence of cortisone," Science 221(4612):719-725.

Galustian et al., "Thalidomide-derived immunomodulatory drugs as therapeutic agents," *Expert Opin. Biol. Ther.*, 2004, 4 (12):1-8.

Gandhi, A., et al., "Dexamethasone Synergizes with Lenalidomide to Inhibit Multiple Myeloma Tumor Growth, But Reduces Lenalidomide-Induced Immunomodulation of T and NK Cell Function," *Current Cancer Drug Targets*, 2010, 10(1):1-13.

Gay, F. et al., "Lenalidomide plus dexamethasone versus thalidomide plus dexamethasone in newly diagnosed multiple myeloma: a comparative analysis of 411 patients," *Blood*, 2010, 115(97):1343-1350.

Gershbein, 1991, "The thalidomide analog, EM 12, enhances 1,2-dimethylhydrazine-induction of rat colon adenocarcinomas," Cancer Letters 60: 129-133.

Glaspy et al., "The potential role of thalidomide and thalidomide analogs in melanoma," *Clinical Advances in Hematology & Oncology*, 2004, 1-7.

Goerner, et al., "Morbidity and mortality of chronic GVHD after hematopoietic stem cell transplantation from HLA-identical siblings for patients with aplastic or refractory anemias," *Biology of Blood and Marrow Transplantation* (Abstract only), 2002, 8(1):47-56.

Gollob, J.A.; Schinpper, C.P.; Orsini, E.; Murphy, E.; Daley, J.F.; Lazo, S.B.; Frank. D.A.; Characterization of a Novel Subset of CD8 T Cells That Expands in patients Receiving Interleukin-12, 02, Am. Soc. For Clin. Investigation, Inc., vol. 102, No. 3, Aug. 1998, pp. 561-575.

Grabstald et al., 1965, "Clinical experiences with thalidomide in patients with cancer," Clinical Pharmacology and Therapeutics 6:298-302.

Grosshans, E. and Illy, G., "Thalidomide Therapy for Inflammatory Dermatoses," *International Journal of Dermatology*, 1984, 23(9):598-602.

Gupta et al., 2001, "Adherence of multiple myeloma cells to bone marrow stromal cells upregulates vascular endothelial growth factor secretion: therapeutic applications," Leukemia 15(12):1950-1961.

Haslett et al., 2003, "Thalidomide and a thalidomide analogue drug costimulate virus-specific CD8+ T cells in vitro," J. Infect. Dis. 187(6):946-955.

Hayashi et al., "Mechanisms whereby immunomodulatory analogs of thalidomide augment autologous NK cell anti-myeloma immunity," *Blood*, Abstract #3219, Dec. 6-10, 2002, *American Society of Hematology*.

He, W., et al., 1993, Abstract of papers, 206th American Chemical Society, Chicago, IL; Med. Chem., paper 216.

Helm et al., "Comparative teratological investigation of compounds of structurally and pharmacologically related to thalidomide," *Arzneimittel Forschung/Drug Research*, 1981, 31 (1)941-949.

Hernandez-Illizalituri et al., "Addition of immunomodulatory drugs CC5013 or CC4047 to rituximab enhances anti-tumor activity in a severe combined immunodeficiency (SCID) mouse lymphoma model," Abstract # 235, *American Society of Hematology*, Dec. 6-9, 2003.

Hideshima et al., "Thalidomide (Thal) and its analogs overcome drug resistance of human multiple myeloma (MM) cells to conventional therapy," Abstract 1313, *American Society of Hematology*, Dec. 1-5, 2000.

Hideshima et al., 2000, "Thalidomide and its analogs overcome drug resistance of human multiple myeloma cells to conventional therapy," Blood 96(9):2943-2950.

Hideshima, T., Chauhan, D., Castro, A., Hayashi, T., Mitsiades, C., Mitsiades, N., Akiyama, M., Richardson, P.G., Schlossman, R.L., Adams, J., Anderson, K.C., NF-KB as a Therapeutic Target in Multiple Myeloma (MM). Abstract #1581. American Society of Hematology, Dec. 7-11, 2001.

(56) References Cited

OTHER PUBLICATIONS

Hideshima, T., et al., "A review of lenalidomide in combination with dexathasone for the treatment of multiple myeloma," *Therapeutics and Clinical Risk Management*, 2008, 4(1):129-136.
Hunt et al., "Markers of endothelial and haemostatic activation in the use of CC-4047, a structural analogue of thalidamide, in relapsed myeloma," *Blood*, Abstract # 3216, Dec. 6-10, 2002, *American Society of Hematology*.
Hussein et al., "Doxil (D), vincristine (V), reduced frequency dexamethasone (d) and Revlimid (DVd-R) a phase I/II trial in advanced relapsed/refractory multiple myeloma (Rmm) patients," *Blood*, Abstract #208, *American Society of Hematology*, Dec. 4-7, 2004.
Hwu et al., "Thalidomide and its analogues in the treatment of metastatic melanoma," *Chemotherapy Foundation Symposium*, Abstract #44, 2002.
Kast, R.E., "Evidence of a mechanism by which etanercept increased TNF-alpha in multiple myeloma: New insights into the biology of TNF-alpha giving new treatment opportunities—the role of burproion," *Leukemia Research*, 2005, 29:1459-1463.
Kon-Nichi No Chiryou Shishin, 1997 [Pocket Edition], Igaku Shoin, 1997, 513-514 (in Japanese).
Krenn, M. et al., "Improvements in Solubility and Stability of Thalidomide upon Complexation with Hydropropyl-β-Cyclodextrin," *Journal of Pharmaceutical Sciences*, 1992, 81(7):685-689.
Kumar, S. et al., "Thalidomide as an anti-cancer agent," *J. Cell. Mod. Med.*, 2002, 6(2):160-174.
Kurzrock, R., "Myelodysplastic syndrome overview," *Seminars in Hematology* (Abstract only), 2002, 39(3)(suppl. 2):18-25 Abstract only.
Kyle et al., "Multiple myeloma," *New England Journal of Medicine*, 2004, 351:1860-1873.
Kyle, "Current therapy of multiple myeloma," *Internal Medicine*, 2002, 41 (3)175-180.
Leblanc et al., "Immunomodulatory drug costimulates T cells via the B7-CD28 pathway," *Blood*, 2004, 103:1787-1790, *American Society of Hematology*.
Lentsch, S., Rogers, M., Leblanc, R., Birsner, A., Shah, J., Anderson K., D'Amato R., 3-Amino-Phthalimido-Glutarimide (S-3APG) Inhibits Angiogenesis and Growth in Drug Resistant Multiple Myeloma (MM) in vivo. Abstract #1976, American Society of Hematology, Dec. 7-11, 2001.
Lentzsch et al., "Immunomodulatory derivative of thalidomide (IMiD CC-4047) determine the lineage commitment of hematopoietic progenitors by down regulation of GATA-1 and modulation of cytokine secretion," Abstract # 3073, *American Society of Hematology*, Dec. 6-9, 2003.
Lentzsch et al., "Immunomodulatory derivative of thalidomide (IMiD CC-4047) down regulates CAAT/enhancer-binding protein $^β$(C/EBP$^β$) in multiple myeloma (MM)," Abstract # 3456, *American Society of Hematology*, Dec. 6-9, 2003.
Lentzsch et al., "In vivo activity of thalidomide and immunomodulatory drugs against multiple myeloma," *VIIIth International Myeloma Workshop*, Abstract #P225, May 4-8, 2001.
Lentzsch et al., 2002, "S-3-amino-phthalimido-glutarimide inhibits angiogenesis and growth of B-cell neoplasias in mice", Cancer Research 62:2300-2305.
Lentzsch et al., 2003, "Immunomodulatory analogs of thalidomide inhibit growth of Hs Sultan cells and angiogenesis in vivo," Leukemia 17(1):41-44.
List, A. et al., "High Erythropoietic Remitting Activity of the Immunomodulatory Thalidomide Analog, CC5013, in Patients with Myelodysplastic Syndrome (MDS)," Abstract #353, *Blood*, 2002, 100(11):96a.
List, A., "New Approaches to the Treatment of Myelodysplasia," *The Oncologist*, 2002, 7(suppl. 1):39-49.
Liu et al., "Phase I study of CC-5013 (Revimid), a thalidomide derivative, in patients with refractory metastatic cancer," *American Society of Clinical Oncology*, Abstract #927, 2003.

Luzzio et al., "Thalidomide analogues: derivatives of an orphan drug with diverse biological activity," *Expert Opin. Ther. Patents*, 2004, 14 (2):215-229.
Man et al., "α-Fluoro-substituted thalidomide analogues," *Bioorganic & Medicinal Chemistry Letters* 13, 2003, 3415-3417.
Marriott et al., "Thalidomide analogue CDC-501 is safe and well tolerated by patients with end stage cancer and shows evidence of clinical responses and extensive immune activation," *Br. J Cancer*, 2002, 86(Supp. 1):Abst 6.4.
Marriott et al., "A novel subclass of thalidomide analogue with anti-solid tumor activity in which caspase-dependent apoptosis is associated with altered expression of bcl-2 family proteins[1]," *Cancer Research*, 2003, 63:593-599.
Marriott et al., "Immunotherapeutic and antitumour potential of thalidomide analogues," *Expert Opin. Biol. Ther.*, 2001, 1 (4):1-8.
Marriott et al., "New thalidomide analogues; anti-cancer, anti-angiogenic and immunostimulatory," *British Journal of Cancer*, 85:25, Jul. 6, 2001.
Marriott et al., "Thalidomide and its analogues have distinct and opposing effects on TNF-α and TNFR2 during co-stimulation of both CD4[+] and CD8[+] T cells," *Clin. Exp. Immunol.*, 2002, 130:75-84.
Marriott et al., "Thalidomide derived immunomodulatory drugs (IMiDs) as potential therapeutic agents," *Current Drug Targets—Immune, Endocrine & Metabolic Disorders*, 2003, 3:181-186.
Masellis et al., "Changes in gene expression in bone marrow mesenchymal progenitor cells as a consequence of IMiD therapy in multiple myeloma patients," *Blood*, Abstract # 1548, Dec. 7-11, 2001, *American Society of Hematology*.
Mauad, 1963, "Clinical Improvements Obtained in Advanced Caner Patients with Treatment with Thalidomide Associated with Hormones," Anais *Paulistas de Medicina e Cirurgia* 86:13-40.
Mazucco, R. and Williams, L., "Immunotherapy, chemoprevention and angiogenesis," *IDrugs*, 2002, 5(5):408-411.
Mazucco, R., "Angiogenesis and Anti-angiogenesis Therapeutics," *IDrugs*, 2002, 5(4): 320-322.
McCarty, "Thalidomide may impede cell migration in primates by down-regulating integrin β-chains: potential therapeutic utility in solid malignancies, proliferative retinopathy, inflammatory disorders, neointimal hyperplasia, and osteoporosis," *Medical Hypotheses*, 1997, 49:123-131.
Merck Manual, 17th ed. Japanese version, 1999, 951-952.
Meregalli et al., "High-dose dexamethasone as first line therapy of multiple myeloma?", Recenti Progressi in Medicina, 1998, 89(1):18-20.
Mitsiades et al., "Apoptic signaling induced by immunomodulatory thalidomide analogs (Imids) in human multiple myeloma cells: therapeutic implications," Abstract # 3224, Dec. 7-11, 2001, *American Society of Hematology*.
Mitsiades et al., "Apoptic signaling induced by immunomodulatory thalidomide analogs in human multiple myeloma cells: therapeutic implications," *Blood*, 2002, 99:4525-4530, *American Society of Hematology*.
Mitsiades et al., "CC-5013 Celgene," *Current Opinion in Investigational Drugs*, 2004, 5 (6):635-647.
Miyachi et al., 1997, "Novel biological response modifiers: phthalimides with tumor necrosis factor-alpha production-regulating activity," J. Med. Chem. 40:2858-2865.
Moutouh et al., "Novel immunomodulatory drugs (IMiDs®): A potential, new therapy for β-hemoglobinopathies," Abstract # 3740, *American Society of Hematology*, Dec. 4-7, 2004.
Mufti, G. et al., "Myelodysplastic Syndrome," *American Society of Hematology*, 2003, pp. 176-199.
Muller et al., 1996, "Structural modifications of thalidomide produce analogs with enhanced tumor necrosis factor inhibitory activity," J. Med. Chem. 39(17):3238-3240.
Muller et al., 1998, "Thalidomide analogs and PDE4 inhibition," Bioorg. Med. Chem. Lett. 8(19):2669-2674.
Muller et al., 1999, "Amino-substituted thalidomide analogs: potent inhibitors of TNF-alpha production," Bioorg. Med. Chem. Lett. 9(11):1625-1630.
N. Ake Jonnson, 1972, "Chemical Structure and Teratogenic Properties," Acta Pharm., pp. 521-542.

(56) References Cited

OTHER PUBLICATIONS

Office Action dated Jun. 18, 2008, U.S. Appl. No. 11/325,954.
Offidani et al., 2003, Thalidomide plus oral melphalan for advanced multiple myeloma: a phase II study. Haematologica. Dec. 2003;88(12):1432-1433.
Okamoto, T., Kotsuzuiikeisei Shoukougun to Men-eki Ijo, Bessatsu Nihon Rinsho, Syndrome Series for each area, No. 22, Blood Syndromes III, Nihon Rinshou, 213-216 (in Japanese), Oct. 1998.
Olson et al., 1965, "Thalidomide (N-phthaloylglutamimide) in the treatment of advanced cancer," Clinical Pharmacology and Therapeutics 6(3):292-297.
Palumbo et al., 2004, "A prospective randomized trial of oral melphalan prednisone, thalidomide (MPT) vs. oral melphalan, prednisone (MP): An interim analysis," Am. Soc. Hematol. 46th Ann. Meeting Dec. 4-7, 2004, San Diego, CA Abstract #207.
Park, Y., Kim, S.A., Kim, C.J., Chung, J.H., Mechanism of the Effect of Thalidomide on Human Multiple Myeloma Cells. Abstract #2685. American Society of Clinical Oncology, May 12-17, 2001.
Patt, Yehuda A.; Hassan, Manal M.; Lozano, Richard D.; Ellis, Lee M.; Peterson, J. Andrew; Waugh, Kimberly A.; Durable Clinical Response of Refractory Hepatocellular Carcinoma to Orally Administered Thalidomide. American Journal of Clinical Oncology, 2000.
Patten et al., "The early use of the serum free light chain assay in patients with relapsed refractory myeloma receiving treatment with a thalidomide analogue (CC-4047)," Abstract # 1640, *American Society of Hematology*, Dec. 6-9, 2003.
Payvandi et al., "CC-5013 inhibits the expression of adhesion molecules ICAM-1 and CD44 and prevents metastasis of B16 F10 mouse melanoma cells in an animal model," *American Society of Clinical Oncology*, Abstract # 992, 2003.
Payvandi et al., "Effects of a thalidomide analog on binding activity of transcription factors and cell cycle progression of multiple myeloma cell lines," *Blood*, Abstract #2487, Dec. 1-5, 2000, *American Society of Hematology*.
Payvandi et al., "Immunomodulatory drugs inhibit expression of cyclooxygenase-2 from TNF-α, IL-1β, and LPS-stimulated human PBMC in a partially IL-10-dependent manner," *Cellular Immunology*, 2004, 81-88.
Payvandi et al., "Thalidomide and IMiDS inhibit microvessel formation from human arterial rings in the absence of human liver microsomes," *Blood*, Abstract # 5046, Dec. 6-10, 2002, *American Society of Hematology*.
Payvandi et al., "Thaliomide analogs IMiDs inhibit expression of cyclooxygenase-2 in multiple myeloma cell line and LPS stimulated PBMCs," *Blood*, Abstract # 2689, Dec. 7-11, 2001, *American Society of Hematology*.
Payvandi et al., "The thalidomide analogs IMiDs enhance expression of CD69 stimulatory receptor on natural killer cells," Abstract # 1793, American Association for Cancer Research, Mar. 24-28, 2001.
Penichet et al., 2001, "Antibody-cytokine fusion proteins for the therapy of cancer," J. Immunol. Methods 248(1-2):91-101.
*Physician's Desk Reference*, 2002, 56th ed., pp. 1755-1760.
Raje et al., "Combination of the mTOR inhibitor rapamycin and CC-5013 has synergistic activity in multiple myeloma," *Blood*, Dec. 15, 2004, 104 (13)4188-4193.
Raje et al., 1999, "Thalidomide—a revival story," N. Engl. J. Med. 341(21):1606-1609.
Raje, N. and Anderson, K., "Thalidomide and immunomodulatory drugs as cancer therapy," *Current Opinions in Oncology*, 2002, 14:635-640.
Rajkumar et al., "Combination therapy with thalidomide plus dexamethasone for newly diagnosed multiple myeloma," *American Society of Hematology*, 43rd Annual Meeting, Dec. 7-11, 2001, Abstract #3525.
Rajkumar et al., "Combination therapy with lenalidomide plus dexamethasone (Rev/Dex) for newly diagnosed myeloma," *Blood*, Dec. 15, 2005, 106 (13)4050-4053.
Rajkumar et al., 2000, "Prognostic value of bone marrow angiogenesis in multiple myeloma," Clin. Cancer Res. 6(8):3111-3116.
Rajkumar et al., 2004, "Thalidomide plus dexamethasone versus dexamethasone alone in newly diagnosed multiple myeloma (E1A00): Results of a phase III trial coordinated by the Eastern Cooperative Oncology Group," Am. Soc. Hematol. 46th Ann. Meeting Dec. 4-7, 2004, San Diego, CA Abstract #205.
Raza et al., 2001, "Thalidomide produces transfusion independence in long-standing refractory anemias of patients with myelodysplatic syndromes," Blood 98(4):958-965.
Ribatti et al., 1999, "Bone marrow angiogenesis and mast cell density increase simultaneously with progression of human multiple myeloma," Br. J. Cancer 79(3-4):451-455.
Richardson et al., "A multi-center, randomized, phase 2 study to evaluate the efficacy and safety of 2 CDC-5013 dose regimens when used alone or in combination with dexamethasone (Dex) for the treatment of relapsed or refractory multiple myeloma (MM)," *Blood*, Abstract # 825, *American Society of Hematology*, Dec. 6-9, 2003.
Richardson et al., "A multicenter, single-arm, open-label study to evaluate the efficacy and safety of single-agent lenalidomide in patients with relapsed and refractory multiple myeloma; preliminary results," 10th International Myeloma Workshop, Apr. 10-14, 2005.
Richardson et al., "A Phase 1 study of oral CC5013, an immunomodulatory thalidomide (Thal) derivative, in patients with relapsed and refractory multiple myeloma (MM)," *Blood*, Abstract #3225, Dec. 7-11, 2001, *American Society of Hematology*.
Richardson et al., "A phase 1 trial of lenalidomide (Revlimid®) with bortezomib (Velcade®) in relapsed and refractory multiple myeloma," *Blood*, Abstract # 365, *American Society of Hematology*, Dec. 10-13, 2005.
Richardson et al., "Immunomodulatory analogs of thalidomide: an emerging new therapy in myeloma," *Journal of Clinical Oncology*, 2004, 22(16) 3212-3214.
Richardson et al., "Immunomodulatory drug CC-5013 overcomes drug resistance and is well tolerated in patients with relapsed multiple myeloma," *Blood*, 2002 100:3063-3067, *American Society of Hematology*.
Richardson et al., "Novel biological therapies for the treatment of multiple myeloma," *Best Practice & Research Clinical Haematology*, 2005, 18 (4):619-634.
Richardson, P. et al., "Thalidomide in multiple myeloma," *Biomed Pharmacother*, 2002, 56:115-28.
Richardson, Paul; Hideshima, Teru; Anderson, Kenneth; Thalidomide: The Revival of a Drug with Therapeutic Promise in the Treatment of Cancer; Principles & Practice of Oncology, vol. 15, No. 2, 2001.
Richardson, Paul; Hideshima, Teru; Anderson, Kenneth; Thalidomide: Emerging Role in Cancer Medicine; Annual Review of Medicine, 2002.
Roe and Mitchley, 1963, "Thalidomide and Neoplasia" *Nature* 200:1016-1017.
Rubin et al, "Principles of Cancer Treatment-1", 12 ONCO IV May 1, 2003.
Samson, D. et al., "Infusion of Vincristine and Doxorubicin with Oral Dexamethasone as First-Line Therapy for Multiple Myeloma," *The Lancet*, 1989, 334(8668):882-885.
Schafer et al., "Enhancement of cytokine production and AP-1 transcriptional activity in T cells by thalidomide-related immunomodulatory drugs," *Journal of Pharmacology and Experimental Therapeutics*, 2003, 305(3)1222-1232.
Scheffler et al., "Safety and pharmacokinetics of CDC-501, a novel immunomodulatory-oncologic agent, after single then multiple, oral 100 mg twice daily doses," *American Society for Clinical Pharmacology and Therapeutics*, Mar. 24-27, 2002, Abstract #WPIII-63.
Schey et al., "A phase I study of an immunomodulatory thalidomide analog, CC-4047, in relapsed or refractory multiple myeloma," *Journal of Clinical Oncology*, 2004, 22 (16):1-8.

(56) References Cited

OTHER PUBLICATIONS

Schey et al., "A phase I study of an immunomodulatory thalidomide analogue (CC4047) in relapse/refractory multiple myeloma," *International Society for Experimental Hematology*, Abstract #248, 2002.
Schmahl, H. J. et al., "Pharmacokinetics of the Teratogenic and Nonteratogenic Thalidomide Analogs EM 12 and Supidimide in the Rat and Marmoset Monkey", in *Pharmacokinetics in Teratogenesis*, CRC Press, 1987, vol. I, Ch. 12, pp. 181-192.
Schumacher, H. et al., "The Teratogenic Activity of a Thalidomide Analogue, $EM_{12}$, in Rabbits, Rats, and Monkeys," *Teratology*, 1971, 5:233-240.
Shah et al., 1999, "Synthesis and enantiomeric separation of 2-phthalimidino-glutaric acid analogues: potent inhibitors of tumor metastasis," J. Med. Chem. 42:3014-3017.
Shaughnessy et al., "Global gene expression analysis shows loss of C-MYC and IL-6 receptor gene mRNA after exposure of myeloma to thalidomide and IMiD," Abstract # 2485, *The American Society of Hematology*, Dec. 1-5, 2000.
Sheskin, J. and Sagher, F., "Trials with Thalidomide Derivatives in Leprosy Reactions," *Leprosy Review*, 1968, 39(4):203-205.
Sheskin, J., "Study with Nine Thalidomide Derivatives in the Lepra Reaction," *Pharmacology and Therapeutics*, 1978, 17:82-84.
Shibata et al., 1995, "N-alkylphthalimides: structural requirement of thalidomidal action on 12-0-tetradecanoylphorbol-13-acetate-induced tumor necrosis factor a production by human leukemia HL-60 cells," Chem. Pharm. Bull. 43(1):177-179.
Shimazawa et al., 1999, "Antiangiogenic activity of tumor necrosis factor-alpha production regulators derived from thalidomide," Biol. Pharm. Bull. 22(2):224-226.
Shire et al., "TNF-α inhibitors and rheumatoid arthritis," *Exp. Opin. Ther. Patents*, 1998, 8 (5):531-544.
Singhal et al., 1999, Antitumor activity of thalidomide in refractory multiple myeloma, N. Engl. J. Med. 341(21):1565-1571.
Singhal, S. and Mehta, J., "Thalidomide in Cancer," *BioDrugs*, 2001, 15(3):163-172.
Smith, R. et al., "Studies on the Relationship Between the Chemical Structure and Embryotoxic Activity of Thalidomide and Related Compounds," in *A Symposium on Embryopathic Activity of Drugs*, J. & A. Churchill Ltd., 1965, Session 6, pp. 194-209.
Sorbera et al., "CC-5013. Treatment of multiple myeloma. Treatment of Melanoma. Treatment of myelodysplastic syndrome. Angiogenesis inhibitor. TNF-α production inhibitor," *Drugs of the Future*, 2003, 28(5):425-431.
Steins et al., 2002, "Efficacy and safety of thalidomide in patients with acute myeloid leukemia," Blood 99(3):834-839.
Stockdale, 1998, Medicine, Rubenstein and Federman, eds., vol. 3, Ch. 12, Sections IV and X.
Streetly et al., "An update of the use and outcomes of the new immunomodulatory agent CC-4047 (Actimid) in patients with relapsed/refractory myeloma," Abstract #829, *American Society of Hematology*, Dec. 6-9, 2003.
Streetly et al., "Changes in neutrophil phenotype following the administration of CC-4047 (Actimid) to patients with multiple myeloma," Abstract # 2543, *American Society of Hematology*, Dec. 6-9, 2003.
Streetly et al., "Thalidomide analogue CC-4047 is effective in the treatment of patients with relapsed and refractory multiple myeloma (MM) and induces T-cell activation and IL-12 production," Abstract # 367, *International Multiple Myeloma Workshop*, May 23-27, 2003.
Swartz, G. et al., "Pre-clinical evaluation of ENMD-0995: A thalidomide analog with activity against multiple myeloma and solid tumors," *Cell and Tumor Biology*, 2002, 43:181-182, Abstract# 910.
Teo et al., "A phase I, single-blind, placebo-controlled, ascending single oral dose, safety, tolerability and pharmacokinetic study of CDC-501, a novel immunomodulatory-oncologic agent, in healthy male subjects with a comparison of fed and fasted," *Clinical Pharmacology and Therapeutics*, 2002, 71 (2)93.
Teo et al., "Chiral inversion of the second generation IMiD™ CC-4047 (Actimid™) in human plasma and phosphate-buffered saline," *Chirality*, 2003, 15:348-351.
Teramura, M., Men-ekiyokusei Ryouhou, *Current Therapy*, 2000, 18(5):140-144 (in Japanese).
Thertulien et al., "Hybrid MEL/DT PACE autotransplant regimen for Multiple Myeloma (MM)-safety and efficacy data in pilot study of 15 patients," *Blood*, Abstract # 2869, *American Society of Hematology*, Dec. 7-11, 2001.
Thomas, D., "Pilot studies of Thalidomide in Acute Myelogenous Leukemia, Myelodysplastic Syndromes, and Myeloproliferative Disorders," *Seminars in Hematology*, 2000, 37(1)(suppl. 3):26-34.
Thomas, D.A., Aguayo, A., Estey, E., Albitar, M., O'Brien, S., Giles, F.J., Beran, M., Cortes, J., Zeldis, J., Keating, M.J., Barlogie, B., Kantarjian, H.M., Thalidomide as anti-angiogenesis therapy (rx) in refractory or relapsed leukemia. Abstract #2269, American Society of Hematology, Dec. 3-7, 1999.
Thomas, Melodie; Doss, Deborah, *Thalidomide Nursing Roundtable Update*, Monograph, Sep. 2002.
Tohnya et al., "A phase I study of oral CC-5013 (lenalidomide, Revlimid™), a thalidomide derivative, in patients with refractory metastatic cancer," *Clinical Prostate Cancer*, 2004, 2:241-243.
Treston, A. et al., "Pre-Clinical Evaluation of a Thalidomide Analog with Activity Against Multiple Myeloma and Solid Tumors—ENMD-0995 (S-(-)-3-(3-amino-phthalimido)-glutarimide)," *Blood*, 2002, 100(11):816a, Abstract #3225.
Tricot et al., "Angiochemotherapy (ACT) for multiple myloma (MM) with DT-PACE results in a high response rate, but in contrast to tandem transplants with melphalan does not affect durable disease control," *Blood*, Abstract # 3531, *American Society of Hematology*, Dec. 7-11, 2001.
Tsenova et al., "Use of IMiD3, a thalidomide analog, as an adjunct to therapy for experimental tuberculous meningitis," *Antimicrobial Agents and Chemotherapy*, 2002, 46 (6)1887-1895.
Tsimberidou, A. et al., "Pilot study of recombinant human soluble tumor necrosis factor (TNF) receptor (p75) fusion protein (TNFR:Fc;Enbrel) in patients with refractory multiple myeloma: increase in plasma TNFα levels during treatment," *Leukemia Research*, 2003, 27:375-380.
Vacca et al., 1999, "Bone marrow neovascularization, plasma cell angiogenic potential, and matrix metalloproteinase-2 secretion parallel progression of human multiple myeloma," Blood 93(9):3064-3073.
Wang, M., et al., "Lenalidomide plus dexamethasone is more effective than dexamethasone alone in patients with relapsed or refractory multiple myeloma regardless of prior thalidomide exposure," *Blood*, 2008, 112(12):4445-4451.
Weber et al., "A multicenter, randomized, parallel-group, double-blind, placebo-controlled study of lenalidomide plus dexamethasone versus dexamethasone alone in previously treated subjects with multiple myeloma," Abstract # PO.738, *International Multiple Myeloma Workshop*, Apr. 10-14, 2005.
Weber, "Lenalidomide (CC-5013, Revlimid™) and other ImiDs," Abstract # PL5.02, *International Multiple Myeloma Workshop*, Apr. 10-14, 2005.
Weber, "Thalidomide and Its Derivatives: New Promise for Multiple Myeloma," *Cancer Control*, vol. 10, No. 5, 375-383, 2003.
Wilen et al., 1977, Tetrahedron 33:2725.
Wilen, 1972, Tables of Resolving Agents and Optical Resolutions, E.L. Eliel, ed., Univ. of Notre Dame Press, Notre Dame, IN pp. 268.
Wohrer et al., 2004, "Effective treatment of primary plasma cell leukemia with thalidomide and dexamethasone—a case report," Hematol. J. 5(4):361-363.
Wolff ed., 1995, *Burger's Medicinal Chemistry and Drug Discovery*, $5^{th}$ ed., pp. 172-178, 949-982.
Worker, C., "JP Morgan Hambrecht & Quist—$20^{th}$ Annual Healthcare Conference," *IDrugs*, 2002, 5(2):113-116.
Ye et al., "Novel IMiD drugs enhance expansion and regulate differentiation of human cord blood CD34+ cells with cytokines," *Blood*, Abstract #4099, *American Society of Hematology*, Dec. 6-10, 2002.

(56) References Cited

OTHER PUBLICATIONS

Zangari et al., "Results of phase I study of CC-5013 for the treatment of multiple myeloma (MM) patients who relapse after high dose chemotherapy (HDCT)," *American Society of Hematology*, Abstract #3226, 2001.

Zangari et al., "Revimid 25 mg (REV 25) × 20 versus 50 mg (REV 50) × 10 q 28 days with bridging of 5 mg × 10 versus 10 mg × 5 as post-transplant salvage therapy for multiple myeloma (MM)," *Blood*, Abstract # 1642, *American Society of Hematology*, Dec. 6-9, 2003.

Zangari et al., "Risk factors for deep vein thrombosis (DVT) in a large group of myeloma patients (Pts) treated with thalidomide (Thal): The Arkansas Experience," *Blood*, Abstract # 681, *American Society of Hematology*,Dec. 7-11, 2001.

Zangari, M., et al., "Thrombogenic activity of doxorubicin in myeloma patients receiving thalidomide: implications for therapy," *Blood*, 2002, 100:1168-1171.

Zeldis et al., "Potential new therapeutics for Waldenstrom's macroglobulinemia," *Seminars in Oncology*, 2003, 30 (2):275-281.

Zeldis et al., "Update on the evolution of the IMiD™," *International Society for Biological Therapy of Cancer, Oral Abstract*, 2003.

Zhang et al., "CC-5079, a novel microtubule and TNF-a inhibitor with anti-angiogenic and antimetastasis activity," Abstract # B012, *International Conference on Molecular Targets and Cancer Therapeutics*, Nov. 17-21, 2003.

Zorat, F. et al., "The clinical and biological effects of thalidomide in patients with myelodysplastic syndromes," *British Journal of Haematology*, 2001, 115:881-894.

Antar et al., "Primary effusion lymphoma in an elderly patient effectively treated by lenalidomide: case report and review of literature," Blood Cancer J. 4:190e (2014).

Lee et al., "Alleviation of systemic manifestations of multicentric Castleman's disease by thalidomide," Am. J. Hematol. 73:48-53 (2003).

"Study of pomalidomide combined with modified DA-EPOCH and rituximab in KSHV-associated lymphomas," (2016).

* cited by examiner

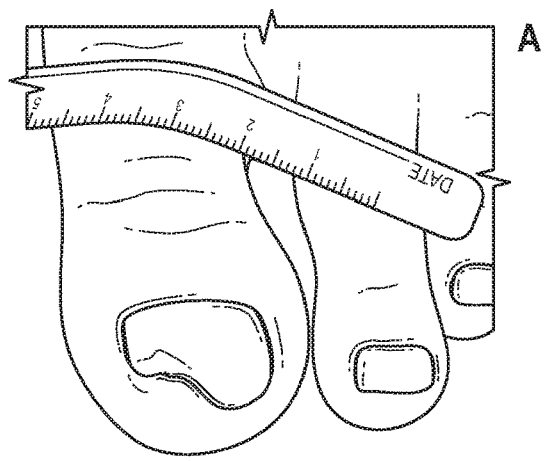
FIG. 10A  Baseline
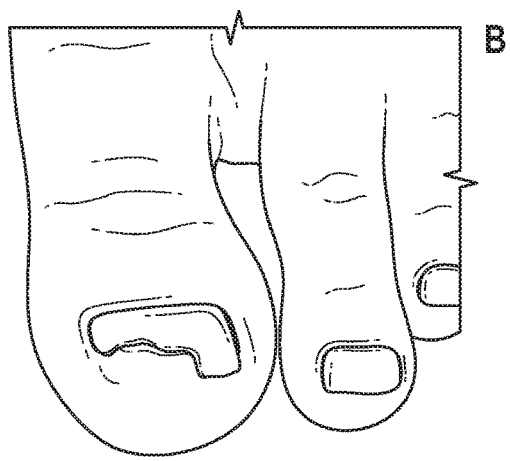
FIG. 10B  Week 4
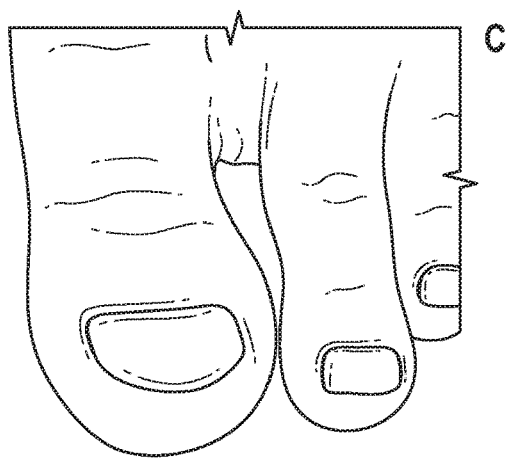
FIG. 10C  Week 24

METHODS FOR THE TREATMENT OF KAPOSI'S SARCOMA OR KSHV-INDUCED LYMPHOMA USING IMMUNOMODULATORY COMPOUNDS, AND USES OF BIOMARKERS

CLAIM OF PRIORITY

This application claims priority to U.S. Provisional Application No. 62/185,265, filed Jun. 26, 2015, the entirety of which is incorporated herein by reference and for all purposes.

STATEMENT OF GOVERNMENT INTEREST

The invention described herein was performed under a Cooperative Research and Development Agreement (CRADA) between U.S. Department of Health and Human Services, National Institutes of Health, National Cancer Institute and Celgene Corporation (CRADA No. 02719). The government has certain rights in the invention.

This invention was made with government support under grant No. HHSN261200800001E awarded by the National Cancer Institute, National Institutes of Health. The government has certain rights in the invention.

FIELD

Provided herein are uses of gene and protein biomarkers as a predictor of clinical sensitivity to Kaposi's sarcoma (KS) or Kaposi's sarcoma-associated herpesvirus (KSHV) induced lymphoma and patient response to treatment with immunomodulatory compounds (e.g., 4-amino-2-(2,6-dioxopiperidin-3-yl)isoindoline-1,3-dione, which is also known as pomalidomide). Also provided herein are methods of treating or managing KSHV induced lymphoma with an immunomodulatory compound (e.g., pomalidomide). Further provided herein are methods of treating or managing Kaposi's sarcoma (KS) with an immunomodulatory compound (e.g., pomalidomide) in combination with a second active agent (e.g., doxorubicin).

BACKGROUND

Kaposi's sarcoma (KS) is a tumor caused by infection with human herpesvirus 8 (HHV8), also known as Kaposi's sarcoma-associated herpesvirus (KSHV) or KS agent. It was originally described by Moritz Kaposi, a Hungarian dermatologist practicing at the University of Vienna in 1872. It became more widely known as one of the AIDS-defining illnesses in the 1980s. It is characterized by proliferation of KSHV-infected spindle cells and abnormal neo-vasculature. KS most frequently involves the skin but may also involve the oral mucosa, lymph nodes, and viscera.

Before the AIDS epidemic, KS was rare in the United States. At that time, only about 2 new cases of KS were found for every million people in the United States each year. Most often, the types of KS that occurred were classic and transplant-related. With the AIDS epidemic, the rate of KS in this country increased more than 20 times—peaking at about 47 cases per million people (per year) in the early 1990s. Early in the AIDS epidemic, patients infected with HIV in the United States were estimated to have a 1 in 2 chance of developing KS. With new treatments for AIDS, KS has become less common in the United States, and it now occurs at a rate of about 6 cases per million people each year. It is still seen most often in people infected with HIV. In the United States, KS is much more common in men than in women, and it is rarely seen in children. It is also more common in African Americans than in whites in the United States. Transplant recipients are another group that gets KS. About 1 in 200 transplant patients in the United States gets KS. In certain instances such patients were already infected with KSHV before the transplant, but due to a healthy immune system, the virus was kept it in check. Following transplant, immunosuppression drugs can allow KS to develop. In areas of the world (such as Africa) where KSHV and HIV infection rates are high, both endemic and HIV-associated KS are seen, and KS occurs in men, women, and children. American Cancer Society website; http://www-.cancer.org/cancer/kaposisarcoma/detailedguide/kaposi-sarcoma-what-is-key-statistics; information last revised Aug. 19, 2014.

The different types of KS are defined by the different populations it develops in, but the changes within the KS cells are very similar. Epidemic (AIDS-related) Kaposi sarcoma: The most common type of KS in the United States is epidemic or AIDS-related KS. This type of KS develops in people who are infected with HIV, the virus that causes AIDS. A person infected with HIV (that is, who is HIV-positive) does not necessarily have AIDS. The virus can be present in the body for a long time, often many years, before causing major illness. The disease known as AIDS begins when the virus has seriously damaged the immune system, which results in certain types of infections or other medical complications, including KS. When HIV damages the immune system, people who also are infected with a certain virus (the Kaposi sarcoma associated herpesvirus or KSHV) are more likely to develop KS. KS is considered an "AIDS defining" illness. This means that when KS occurs in someone infected with HIV, that person officially has AIDS (and is not just HIV-positive). In the United States, treating HIV infection with highly active antiretroviral therapy (HAART) has resulted in fewer cases of epidemic KS. Still, some patients develop symptoms of KS in the first few months of HAART treatment. For most patients with HIV, HAART can often keep advanced KS from developing. Still, KS can still occur in people whose HIV is well controlled with HAART. Once KS develops it is still important to continue HAART. In areas of the world where HAART is not easy to obtain, KS in AIDS patients can advance quickly.

Classic (Mediterranean) Kaposi sarcoma: Classic KS occurs mainly in older people of Mediterranean, Eastern European, and Middle Eastern heritage. Classic KS is more common in men than in women. Patients typically have one or more lesions on the legs, ankles, or the soles of the feet. Compared to other types of KS, the lesions in this type do not grow as quickly, and new lesions do not develop as often. The immune system of people with classic KS is not as weak as it is in those who have epidemic KS, but it may be weaker than normal. Getting older can naturally weaken the immune system a little. When this occurs, people who already have a KSHV (Kaposi sarcoma associated herpesvirus) infection are more likely to develop KS.

Endemic (African) Kaposi sarcoma: Endemic KS occurs in people living in Equatorial Africa and is sometimes called African KS. KSHV (Kaposi sarcoma associated herpesvirus) infection is much more common in Africa than in other parts of the world, so the risk of KS is higher. Other factors in Africa that weaken the immune system (such as malaria, other chronic infections, and malnutrition) also probably contribute to the development of KS, since the disease affects a broader group of people that includes children and women. Endemic KS tends to occur in younger people (usually under age 40). Rarely a more aggressive form of endemic KS is seen in children before puberty. This type usually affects the lymph nodes and other organs and can progress quickly. Endemic KS used to be the most common type of KS in Africa. Then, as AIDS became more common in Africa, the epidemic type became more common.

Iatrogenic (transplant-related) Kaposi sarcoma: When KS develops in people whose immune systems have been suppressed after an organ transplant, it is called iatrogenic, or transplant-related KS. Most transplant patients need to take drugs to keep their immune system from rejecting (attacking) the new organ. But by weakening the body's immune system, these drugs increase the chance that someone infected with KSHV (Kaposi sarcoma associated herpesvirus) will develop KS. Stopping the immune-suppressing drugs or lowering their dose often makes KS lesions go away or get smaller.

Kaposi sarcoma in HIV negative men who have sex with men: There have been reports of KS developing in men who have sex with men who are not infected with HIV. In this group, the cases of KS are often mild, similar to cases of classic KS.

For AIDS-related KS, most doctors use the AIDS Clinical Trials Group system. The AIDS Clinical Trials Group (ACTG) system for AIDS-related KS considers 3 factors: the extent of the tumor (T), the status of the immune system (I), as measured by the number of certain immune cells (CD4 cells) present in the blood, and the extent of involvement within the body or systemic illness (S). Under each major factor, there are 2 subgroups: either a 0 (good risk) or a 1 (poor risk).

T0 (good risk): Localized tumor. KS is only in the skin and/or the lymph nodes (bean-sized collections of immune cells throughout the body), and/or there is only a small amount of disease on the palate (roof of the mouth). The KS lesions in the mouth are flat rather than raised.

T1 (poor risk): The KS lesions are widespread. One or more of the following is present: edema (swelling) or ulceration (breaks in the skin) due to the tumor; extensive oral KS lesions that are nodular (raised) and/or lesions in areas of the mouth besides the palate (roof of the mouth); lesions of KS are in organs other than lymph nodes (such as the lungs, the intestine, the liver, etc.). Kaposi sarcoma in the lungs is a particularly bad sign.

I0 (good risk): CD4 cell count is 150 or more cells per cubic mm ($mm^3$).

I1 (poor risk): CD4 cell count is lower than 150 cells per $mm^3$.

S0 (good risk): No systemic illness present; all of the following are true: no history of opportunistic infections (infections that rarely cause problems in healthy people but affect people with suppressed immune systems) or thrush (a fungal infection in the mouth); no B symptoms lasting more than 2 weeks. B symptoms include: unexplained fever, night sweats (severe enough to soak the bed clothes), weight loss of more than 10% without dieting, diarrhea.

S1 (poor risk): Systemic illness present; one or more of the following is true: history of opportunistic infections or thrush; one or more B symptoms is present; KPS score is under 70; other HIV-related illness is present, such as neurological (nervous system) disease or lymphoma.

KSHV is also the causative agent of two B-cell lymphomas, primary effusion lymphoma (PEL) and multicentric Castleman's disease (MCD), commonly seen in AIDS patients. There is currently no standard of care treatment for PEL, which is often lethal within 2 years. PEL cells latently infected with KSHV have constitutive up-regulation of NFkB and IRF4 and this is considered important in cell proliferation and disease pathogenesis of PEL.

An important component of the immune system is the killing of cells by cytotoxic T cells. Cytotoxic T cells recognize antigens such as peptides that are expressed bound to major histocompatibility complex class I (MHC-1) molecules, and expression of MHC-1 molecules is essential for an effective cytotoxic T cell response. This response is particularly important in the destruction of cells that produce abnormal proteins, including cells infected by viruses or bacteria, or tumor cells. Various viruses, including Kaposi sarcoma associated herpesvirus (KSHV), have evolved mechanisms to suppress expression of MHC-1, and this can enable them to evade killing by cytotoxic T cells. In addition, suppression of MHC-1 expression by tumors caused by KSHV or other viruses can blunt the immune response to the tumors, allowing them to develop and then facilitating their growth. In the case of KSHV, much of the suppressing of MHC-1 is the result of two lytic KSHV genes, K3 and K5, that act as ubiquitin ligases.

Despite antiretroviral therapy (ART), people with HIV continue to exhibit immune deficits including failure to fully reconstitute CD4 T-cell numbers and function, resulting in increased risks of tumors and infections and reduced response to vaccination. There still exists an unmet need for agents for the treatment of KS and other KSHV-induced cancers which are deliverable orally, accessible in resource-limiting settings, and/or work long term for relapsing diseases.

Pomalidomide is an immunomodulatory compound that has a number of actions, including an anti-tumor effect in multiple myeloma and an increase in T cell responsiveness. Lenalidomide is another immunomodulatory compound that is approved for use in multiple myeloma and also has been shown to be active in certain lymphomas. It has been found that one basis for the activity of immunomodulatory compounds is their binding to cereblon, a component of the U3 ubiquitin ligase. See Ishido et al., J. Virol. 2000, 74:5300-9; Paulson et al., Virology 2001, 288:369-78; Horst et al., Current opinion in immunology 2011, 23:96-103. Pomalidomide augments T cells responsiveness and proliferation by several mechanisms, leading to increased production of IL-2 and interferon-γ (IFN-γ). It enhances CD4- and CD8-positive T cell co-stimulation, associated with increased tyrosine phosphorylation of CD28 on T cells and activation of the PI3-K signaling pathway, and enhances transcriptional activity of activated protein-1 (AP-1), a driver of IL-2. This T cell reprogramming is mediated at least in part by induction of the transcription factor T-bet. In addition, T regulatory (Treg) cell expansion and FOXP3 expression on Tregs are inhibited without affecting survival or apoptosis, or Treg expression of IL-10 or TGF-β. Th1 cytokine production is also enhanced There is a substantial unmet need for novel KS therapies. There is a lack of effective oral agents; chronic administration of cytotoxic agents is poorly tolerated, in part due to hematotoxicity; and cumulative anthracyclines increase cardiotoxicity risk. The latter considerations are significant as KS commonly recurs and patients often require treatment, at least intermittently, for years. Also, with the exception of ART, no treatment is readily deliverable in resource-limited areas such as sub-Saharan Africa where KS burden is greatest. Accordingly, provided herein is a solution to these and other problems in the art.

SUMMARY

A method of treating or managing Kaposi's sarcoma-associated herpesvirus (KSHV) induced lymphoma or lymphoproliferative disease, comprising:

(i) identifying a patient having KSHV-induced lymphoma sensitive to treatment with a compound of the formula:

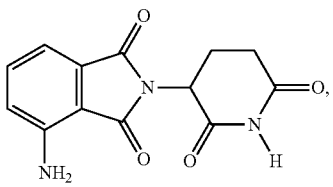

or a pharmaceutically acceptable salt, solvate or stereoisomer thereof; and (ii) administering to the patient a therapeutically effective amount of the compound.

A method of treating or managing Kaposi's sarcoma-associated herpesvirus (KSHV) induced lymphoma, comprising:

(i) identifying a patient having KSHV-induced lymphoma sensitive to treatment with a compound of the formula:

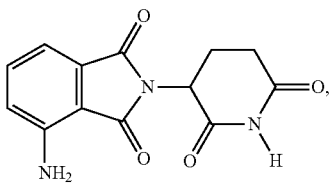

or a pharmaceutically acceptable salt, solvate or stereoisomer thereof; and (ii) administering to the patient a therapeutically effective amount of the compound.

A method for predicting response to treatment in a patient having KSHV-induced lymphoma or lymphoproliferative disease, comprising:

(i) obtaining a biological sample from the patient;

(ii) measuring the level of MHC-1 in the biological sample; and (iii) comparing the level of MHC-1 in the biological sample to that of a biological sample from a subject not infected with KSHV;

wherein a decreased level of MHC-1 in the biological sample from the patient relative to that from the subject not infected with KSHV indicates a likelihood of an effective response to the treatment with a compound of the formula:

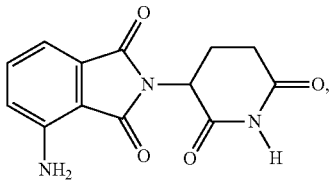 [SMILES: Nc1cccc2c1C(=O)N(C1CCC(=O)NC1=O)C2=O]

or a pharmaceutically acceptable salt, solvate or stereoisomer thereof.

A method for predicting response to treatment in a patient having KSHV-induced lymphoma, comprising:

(i) obtaining a biological sample from the patient;

(ii) measuring the level of MHC-1 in the biological sample; and (iii) comparing the level of MHC-1 in the biological sample to that of a biological sample from a subject not infected with KSHV;

wherein a decreased level of MHC-1 in the biological sample from the patient relative to that from the subject not infected with KSHV indicates a likelihood of an effective response to the treatment with a compound of the formula:

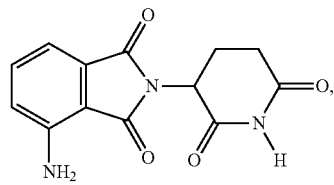

or a pharmaceutically acceptable salt, solvate or stereoisomer thereof.

A method for monitoring response to treatment in a patient having KSHV-induced lymphoma or lymphoproliferative disease, comprising:

(i) obtaining a first biological sample from the patient;

(ii) measuring the level of MHC-1 in the first biological sample;

(iii) administering to the patient a therapeutically effective amount of a compound of the formula:

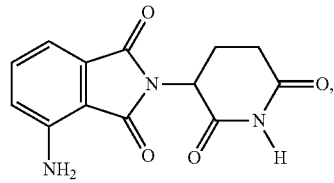

or a pharmaceutically acceptable salt, solvate or stereoisomer thereof;

(iv) obtaining a second biological sample from the patient;

(v) measuring the level of MHC-1 in the second biological sample; and (vi) comparing the level of MHC-1 in the first biological sample to that in the second biological sample;

wherein an increased level of MHC-1 in the second biological sample relative to the first biological sample indicates a likelihood of an effective response.

A method for monitoring response to treatment in a patient having KSHV-induced lymphoma, comprising:

(i) obtaining a first biological sample from the patient;

(ii) measuring the level of MHC-1 in the first biological sample;

(iii) administering to the patient a therapeutically effective amount of a compound of the formula:

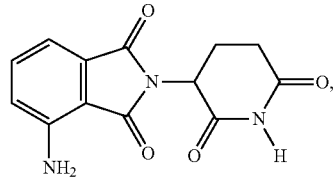 [SMILES: Nc1cccc2c1C(=O)N(C1CCC(=O)NC1=O)C2=O]

or a pharmaceutically acceptable salt, solvate or stereoisomer thereof;
(iv) obtaining a second biological sample from the patient;
(v) measuring the level of MHC-1 in the second biological sample; and
(vi) comparing the level of MHC-1 in the first biological sample to that in the second biological sample;
wherein an increased level of MHC-1 in the second biological sample relative to the first biological sample indicates a likelihood of an effective response.

A method for monitoring patient compliance with treatment with a compound of the formula:

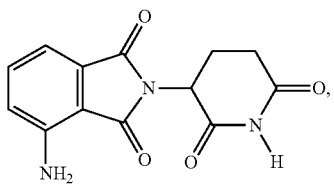

or a pharmaceutically acceptable salt, solvate or stereoisomer thereof, in a patient having KSHV-induced lymphoma or lymphoproliferative disease, comprising:
(i) obtaining a biological sample from the patient;
(ii) measuring the level of MHC-1 in the biological sample; and
(iii) comparing the level of MHC-1 in the biological sample to a control untreated sample;
wherein an increased level of MHC-1 in the biological sample relative to the control untreated sample indicates patient compliance with the treatment.

A method for monitoring patient compliance with treatment with a compound of the formula:

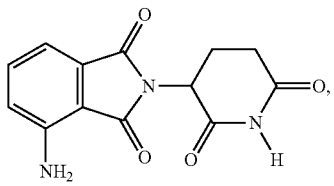

or a pharmaceutically acceptable salt, solvate or stereoisomer thereof, in a patient having KSHV-induced lymphoma, comprising:
(i) obtaining a biological sample from the patient;
(ii) measuring the level of MHC-1 in the biological sample; and
(iii) comparing the level of MHC-1 in the biological sample to a control untreated sample;
wherein an increased level of MHC-1 in the biological sample relative to the control untreated sample indicates patient compliance with the treatment.

A method for monitoring response to treatment in a patient having Kaposi's sarcoma, comprising:
(i) obtaining a first biological sample from the patient;
(ii) measuring the level of MHC-1 in the first biological sample;
(iii) administering to the patient a therapeutically effective amount of a compound of the formula:

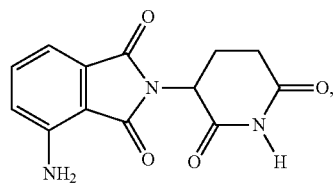 [SMILES: Nc1cccc2c1C(=O)N(C1CCC(=O)NC1=O)C2=O]

or a pharmaceutically acceptable salt, solvate or stereoisomer thereof;
(iv) obtaining a second biological sample from the patient;
(v) measuring the level of MHC-1 in the second biological sample; and
(vi) comparing the level of MHC-1 in the first biological sample to that in the second biological sample;
wherein an increased level of MHC-1 in the second biological sample relative to the first biological sample indicates a likelihood of an effective response.

A method for predicting response to treatment in a patient having Kaposi's sarcoma, comprising:
(i) obtaining a biological sample from the patient;
(ii) measuring the level of MHC-1 in the biological sample; and
(iii) comparing the level of MHC-1 in the biological sample to that of a biological sample from a subject not infected with KSHV;
wherein a decreased level of MHC-1 in the biological sample from the patient relative to that from the subject not infected with KSHV indicates a likelihood of an effective response to the treatment with a compound of the formula:

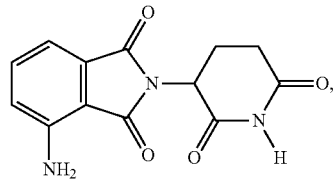 [SMILES: Nc1cccc2c1C(=O)N(C1CCC(=O)NC1=O)C2=O]

or a pharmaceutically acceptable salt, solvate or stereoisomer thereof.

A method for monitoring response to treatment in a patient having Kaposi's sarcoma, comprising:
(i) obtaining a first biological sample from the patient;
(ii) measuring the level of MHC-1 in the first biological sample;
(iii) administering to the patient a therapeutically effective amount of a compound of the formula:

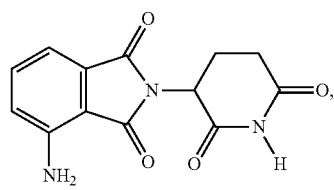 [SMILES: Nc1cccc2c1C(=O)N(C1CCC(=O)NC1=O)C2=O]

or a pharmaceutically acceptable salt, solvate or stereoisomer thereof;
(iv) obtaining a second biological sample from the patient;

(v) measuring the level of MHC-1 in the second biological sample; and (vi) comparing the level of MHC-1 in the first biological sample to that in the second biological sample;

wherein an increased level of MHC-1 in the second biological sample relative to the first biological sample indicates a likelihood of an effective response.

A method for monitoring patient compliance with treatment with a compound of the formula:

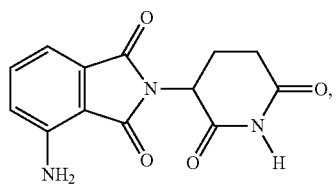

or a pharmaceutically acceptable salt, solvate or stereoisomer thereof, in a patient having Kaposi's sarcoma, comprising:

(i) obtaining a biological sample from the patient;

(ii) measuring the level of MHC-1 in the biological sample; and (iii) comparing the level of MHC-1 in the biological sample to a control untreated sample;

wherein an increased level of MHC-1 in the biological sample relative to the control untreated sample indicates patient compliance with the treatment.

A method of treating or managing Kaposi's sarcoma-associated herpesvirus (KSHV) induced lymphoma or lymphoproliferative disease, which comprises administering to a patient having KSHV-induced lymphoma or lymphoproliferative disease from about 1 mg to about 5 mg per day of a compound having the formula:

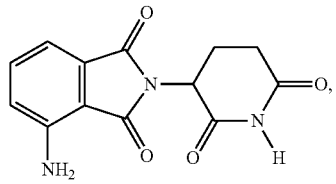

or a pharmaceutically acceptable salt, solvate or stereoisomer thereof, wherein the compound is administered in one or more cycles, each of which comprises administering the compound for a period of time followed by a period of rest.

A method of treating or managing Kaposi's sarcoma-associated herpesvirus (KSHV) induced lymphoma, which comprises administering to a patient having KSHV-induced lymphoma from about 1 mg to about 5 mg per day of a compound having the formula:

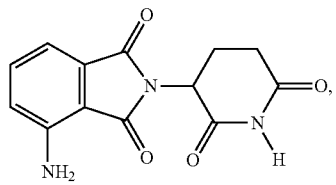

or a pharmaceutically acceptable salt, solvate or stereoisomer thereof, wherein the compound is administered in one or more cycles, each of which comprises administering the compound for a period of time followed by a period of rest.

A method of treating or managing primary effusion lymphoma (PEL), comprising:

(i) identifying a patient having PEL sensitive to treatment with a compound of the formula:

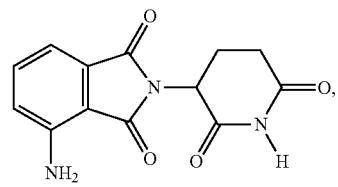

or a pharmaceutically acceptable salt, solvate or stereoisomer thereof; and (ii) administering to the patient a therapeutically effective amount of the compound.

A method of treating or managing Kaposi's sarcoma, which comprises administering to a patient having Kaposi's sarcoma from about 1 mg to about 5 mg per day of a compound having the formula:

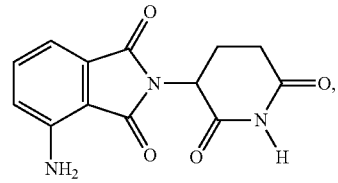 [SMILES: Nc1cccc2c1C(=O)N(C1CCC(=O)NC1=O)C2=O]

or a pharmaceutically acceptable salt, solvate or stereoisomer thereof, in combination with a therapeutically effective amount of doxorubicin, wherein the compound is administered in one or more cycles, each of which comprises administering the compound for a period of time followed by a period of rest.

A method of treating or managing Kaposi's sarcoma-associated herpesvirus (KSHV) induced lymphoma or lymphoproliferative disease, comprising:

(i) identifying a patient having KSHV-induced lymphoma sensitive to treatment with a compound of the formula:

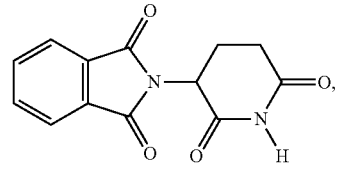 [SMILES: O=C1CCC(N2C(=O)c3ccccc3C2=O)C(=O)N1]

or a pharmaceutically acceptable salt, solvate or stereoisomer thereof; and (ii) administering to the patient a therapeutically effective amount of the compound.

A method of treating or managing Kaposi's sarcoma-associated herpesvirus (KSHV) induced lymphoma or lymphoproliferative disease, comprising:

(i) identifying a patient having KSHV-induced lymphoma sensitive to treatment with a compound of the formula:

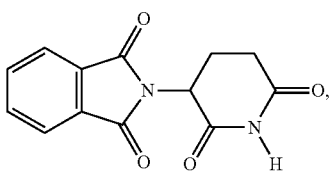

or a pharmaceutically acceptable salt, solvate or stereoisomer thereof; and (ii) administering to the patient a therapeutically effective amount of the compound.

A method of treating or managing Kaposi's sarcoma-associated herpesvirus (KSHV) induced lymphoma or lymphoproliferative disease, comprising:

(i) identifying a patient having KSHV-induced lymphoma or lymphoproliferative disease sensitive to treatment with a compound of the formula:

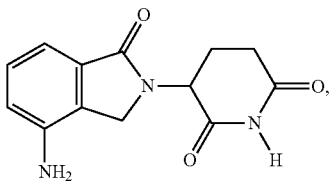 [SMILES: Nc1cccc2c1CN(C1CCC(=O)NC1=O)C2=O]

or a pharmaceutically acceptable salt, solvate or stereoisomer thereof; and (ii) administering to the patient a therapeutically effective amount of the compound.

A method of treating or managing Kaposi's sarcoma-associated herpesvirus (KSHV) induced lymphoma or lymphoproliferative disease, comprising:

(i) identifying a patient having KSHV-induced lymphoma or lymphoproliferative disease sensitive to treatment with a compound of the formula:

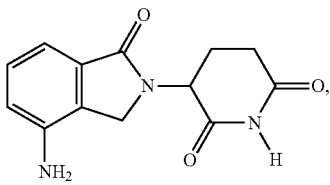 [SMILES: Nc1cccc2c1CN(C1CCC(=O)NC1=O)C2=O]

or a pharmaceutically acceptable salt, solvate or stereoisomer thereof; and (ii) administering to the patient a therapeutically effective amount of the compound.

BRIEF DESCRIPTION OF THE FIGURES

FIG. 10A shows a representative response of a left great toe lesion (one of a number present on this subject) at baseline and prior to pomalidomide therapy.

FIG. 10B shows a representative response of the left great toe lesion of the same patient in FIG. 10A to pomalidomide treatment after 4 weeks showing complete flattening of the lesion.

FIG. 10C shows a representative response of the left great toe lesion of the same patient in FIG. 10A to pomalidomide treatment 24 weeks showing complete resolution of the lesion and a complete pathological response.

DETAILED DESCRIPTION

Figure 1A:
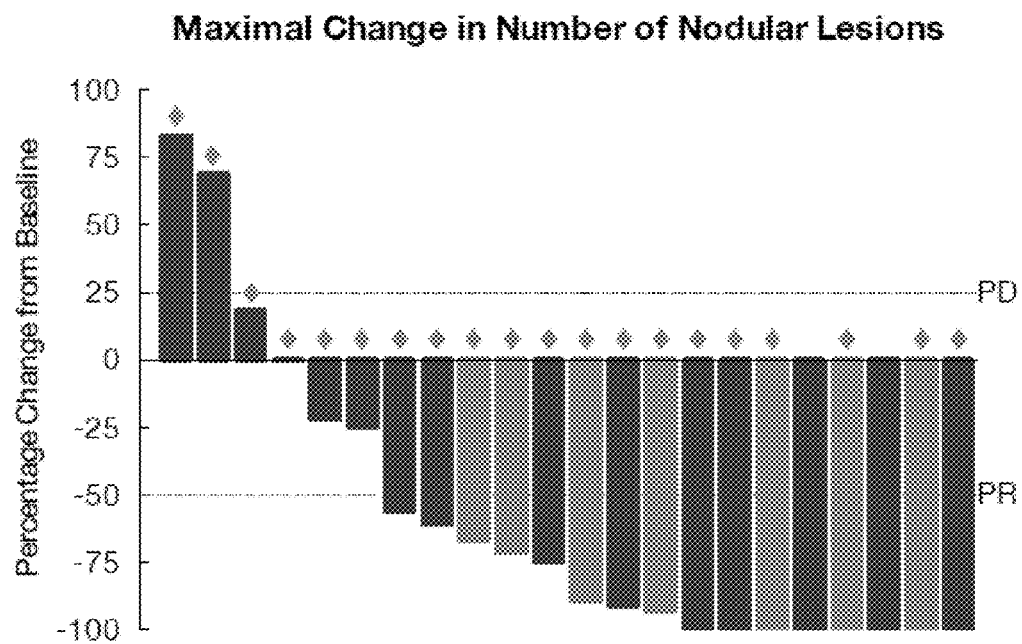
FIG. 1A shows individual responses (maximal change in number of nodular lesions) from Kaposi's sarcoma patients after treatment with pomalidomide.

To facilitate understanding of the disclosure set forth herein, a number of terms are defined below. Generally, the nomenclature used herein and the laboratory procedures in skin care, dermatology, pathology, organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

As used herein, the compound 4-amino-2-(2,6-dioxopiperidin-3-yl)isoindoline-1,3-dione, also known as pomalidomide, has the following structure:

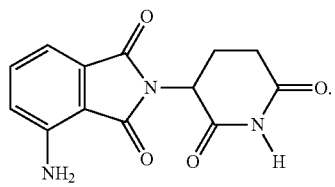

As used herein, the compound 3-(4-amino-1-oxo 1,3-dihydro-2H-isoindol-2-yl) piperidine-2,6-dione, also known as lenalidomide, has the following structure:

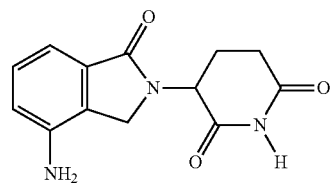 [SMILES: Nc1cccc2c1CN(C1CCC(=O)NC1=O)C2=O]

As used herein, the compound 2-(2,6-dioxopiperidin-3-yl)-1H-isoindole-1,3(2H)-dione, also known as thalidomide, has the following structure:

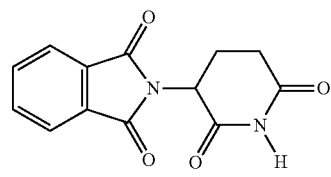 [SMILES: O=C1CCC(N2C(=O)c3ccccc3C2=O)C(=O)N1]

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a condition, or one or more of the symptoms associated with the condition; or alleviating or eradicating the cause(s) of the condition itself.

The terms "manage," "managing," and "management" encompass preventing the recurrence of the specified disease, disorder, or condition in a patient who has already suffered from the disease, disorder, or condition, and/or lengthening the time that a patient who has suffered from the disease, disorder, or condition remains in remission. The terms encompass modulating the threshold, development and/or duration of the disease, disorder, or condition, or changing the way that a patient responds to the disease, disorder, or condition.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "sensitivity" and "sensitive" when made in reference to treatment with compound is a relative term which refers to the degree of effectiveness of the compound in lessening or decreasing the progress of the disease, disorder, or condition being treated. For example, the terms "increased sensitivity" or "sensitive to treatment" when used in reference to treatment of a disease, disorder, or condition in connection with a compound refers to an increase of at least 3%, in particular at least 5%, or more, in the effectiveness of the treatment.

As used herein, and unless otherwise specified, the term "therapeutically effective amount" of a compound is an amount sufficient to provide a therapeutic benefit in the treatment or management of a disease, disorder, or condition, or to delay or minimize one or more symptoms associated with the presence of the disease, disorder, or condition. A therapeutically effective amount of a compound means an amount of therapeutic agent, alone or in combination with other therapies, which provides a therapeutic benefit in the treatment or management of the disease, disorder, or condition. The term "therapeutically effective amount" can encompass an amount that improves overall therapy, reduces or avoids symptoms or causes of the disease, disorder, or condition, or enhances the therapeutic efficacy of another therapeutic agent.

As used herein, an "effective patient response" refers to any increase in the therapeutic benefit to the patient. An "effective patient response" can be, for example, a 5%, 7.5%, 10%, 15%, 20%, 25%, 30%, 35%, 40%, 45%, 50%, 60%, 70%, 75%, 80%, 90%, or 100% decrease in the rate of progress of the disease, disorder, or condition. An "effective patient response" can be, for example, a 5%, 7.5%, 10%, 15%, 20%, 25%, 30%, 35%, 40%, 45%, 50%, 60%, 70%, 75%, 80%, 90%, or 100% decrease in the physical symptoms of a disease, disorder, or condition. An "effective patient response" can also be, for example, a 5%, 7.5%, 10%, 15%, 20%, 25%, 30%, 35%, 40%, 45%, 50%, 60%, 70%, 75%, 80%, 90%, 100%, 120%, 140%, 150%, 170%, 180%, 190%, 200%, or more increase in the response of the patient, as measured by any suitable means, such as gene expression, cell counts, assay results, etc.

An improvement in the disease, disorder, or condition can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable disease, disorder, or condition burden (i.e., the number of malignant cells present in the subject, or the measured bulk of tumor masses or the quantity of abnormal monoclonal protein) in the absence of new lesions. The term "treatment" contemplates both a complete and a partial response.

The term "refractory or resistant" refers to a circumstance where patients, even after intensive treatment, do not respond to treatment. For example, patients may have residual cancer cells (e.g., leukemia or lymphoma cells) in their lymphatic system, blood and/or blood forming tissues (e.g., marrow).

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

The terms "isolated" and "purified" refer to isolation of a substance (such as mRNA or protein) such that the substance comprises a substantial portion of the sample in which it resides, i.e. greater than the substance is typically found in its natural or un-isolated state. Typically, a substantial portion of the sample comprises, e.g., greater than 1%, greater than 2%, greater than 5%, greater than 10%, greater than 15%, greater than 20%, greater than 25%, greater than 30%, greater than 40%, greater than 50%, or more, usually up to about 90%-100% of the sample. For example, a sample of isolated mRNA can typically comprise at least about 1% total mRNA. Techniques for purifying polynucleotides are well known in the art and include, for example, gel electrophoresis, ion-exchange chromatography, affinity chromatography, flow sorting, and sedimentation according to density.

The term "sample" as used herein relates to a material or mixture of materials, typically, although not necessarily, in fluid form, containing one or more components of interest.

"Biological sample" as used herein refers to a sample obtained from a biological subject, including sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Biological samples include but are not limited to whole blood, partially purified blood, PBMCs, tissue biopsies, and the like.

As used herein, and unless otherwise indicated, the term "optically pure" means a composition that comprises one optical isomer of a compound and is substantially free of other isomers of that compound. For example, an optically pure composition of a compound having one chiral center will be substantially free of the opposite enantiomer of the compound. An optically pure composition of a compound having two chiral centers will be substantially free of other diastereomers of the compound. A typical optically pure compound comprises greater than about 80% by weight of one enantiomer of the compound and less than about 20% by weight of other enantiomers of the compound, or greater than about 90% by weight of one enantiomer of the compound and less than about 10% by weight of the other enantiomers of the compound, or greater than about 95% by weight of one enantiomer of the compound and less than about 5% by weight of the other enantiomers of the compound, or greater than about 97% by weight of one enantiomer of the compound and less than about 3% by weight of the other enantiomers of the compound, or greater than about 99% by weight of one enantiomer of the compound and less than about 1% by weight of the other enantiomers of the compound.

The term "pharmaceutically acceptable" is used in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 22nd ed.; Pharmaceutical Press: 2012; *Handbook of Pharmaceutical Excipients,* 7th ed.; Rowe et al., Eds.; The Pharmaceutical Press: 2012; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

The term "pharmaceutically acceptable prodrug or salt" is used throughout the specification to describe any pharmaceutically acceptable form (such as an ester, phosphate ester, salt of an ester or a related group) of a compound which, upon administration to a patient, provides the active compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the active compound. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein and unless otherwise indicated, the term "solvate" means a compound provided herein or a salt thereof, that further includes a stoichiometric or non-stoichiometric amount of solvent bound by non-covalent intermolecular forces. Where the solvent is water, the solvate is a hydrate.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, or greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, or greater than about 70% by weight, or greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

Immunomodulatory Compounds

Compounds for the methods provided herein include, but are not limited to, the immunomodulatory compounds, including compounds known as "IMiDs®" (Celgene Corporation), a group of compounds that can be useful to treat several types of human diseases, including certain cancers.

As used herein and unless otherwise indicated, the term "immunomodulatory compound" can encompass certain small organic molecules that inhibit LPS induced monocyte TNF-α, IL-1β, IL-12, IL-6, MIP-1α, MCP-1, GM-CSF, G-CSF, and COX-2 production. These compounds can be prepared synthetically, or can be obtained commercially.

Exemplary immunomodulating compounds include but are not limited to N-{[2-(2,6-dioxo(3-piperidyl)-1,3-dioxoisoindolin-4-yl]methyl}cyclopropyl-carboxamide; 3-[2-(2,6-dioxo-piperidin-3-yl)-1,3-dioxo-2,3-dihydro-1H-isoindol-4-ylmethyl]-1,1-dimethyl-urea; (−)-3-(3,4-Dimethoxy-phenyl)-3-(1-oxo-1,3-dihydro-isoindol-2-yl)-propionamide; (+)-3-(3,4-Dimethoxy-phenyl)-3-(1-oxo-1,3-dihydro-isoindol-2-yl)-propionamide; (−)-{2-[1-(3-ethoxy-4-methoxy-phenyl)-2-methylsulfonylethyl]-4-acetylaminoisoindoline-1,3-dione}; (+)-{2-[1(3-ethoxy-4-methoxyphenyl)-2-methylsulfonylethyl]-4-acetylaminoisoindoline-1,3-dione}; Difluoro-methoxy SelCIDs; 1-phthalimido-1-(3,4-diethoxy-phenyl)ethane; dimethoxyphenyl)-3-(3,5-dimethoxyphenyl) acrylo nitrile; 1-oxo-2-(2,6-dioxopiperidin-3-yl)-4-aminoisoindoline; 1,3-dioxo-2-(2,6-dioxopiperidin-3-yl)-4-aminoisoindoline; 4-amino-2-(3-methyl-2,6-dioxo-piperidine-3-yl)-isoindole-1,3-dione; 3-(3-acetoamidophthalimido)-3-(3-ethoxy-4-methoxyphenyl)-N-hydroxypropionamide; 1-oxo-2-(2,6-dioxopiperidin-3-yl)-4-methylisoindoline; Cyclopropyl-N-{2-[(15)-1-(3-ethoxy-4-methoxyphenyl)-2-(methylsulfonyl)ethyl]-3-oxoisoindoline-4-yl}carboxamide; Substituted 2-(3-hydroxy-2,6-dioxopiperidin-5-yl) isoindoline; N-[2-(2,6-Dioxo-piperidin-3-yl)-1,3-dioxo-2,3-dihydro-1H-isoindol-5-ylmethyl]-4-trifluoromethoxybenzamide; (S)-4-chloro-N-((2-(3-methyl-2,6-dioxopiperidin-3-yl)-1,3-dioxoisoindolin-5-yl)methyl)benzamide; Pyridine-2-carboxylic acid [2-[(3 S)-3-methyl-2,6-dioxo-piperidin-3-yl]-1,3-dioxo-2,3-dihydro-1H-isoindol-5-ylmethyl]-amide; (S)—N-((2-(3-methyl-2,6-dioxopiperidin-3-yl)-1,3-dioxoisoindolin-5-yl)methyl)-4-(trifluoromethyl)benzamide; 3-(2,5-dimethyl-4-oxo-4H-quinazolin-3-yl)-piperidine-2,6-dione, and the like.

The inflammatory cytokine TNF-α, which is produced by macrophages and monocytes during acute inflammation, causes a diverse range of signaling events within cells. Without being limited by a particular theory, one of the biological effects exerted by the immunomodulatory compounds disclosed herein is the reduction of myeloid cell TNF-α production. Immunomodulatory compounds disclosed herein may enhance the degradation of TNF-α mRNA.

Further, without being limited by theory, immunomodulatory compounds disclosed herein may also be potent co-stimulators of T cells and increase cell proliferation dramatically in a dose dependent manner. Immunomodulatory compounds disclosed herein may also have a greater co-stimulatory effect on the CD8+ T cell subset than on the CD4+ T cell subset. In addition, the compounds may have anti-inflammatory properties against myeloid cell responses, yet efficiently co-stimulate T cells to produce greater amounts of IL-2, IFN-γ, and to enhance T cell proliferation and CD8+ T cell cytotoxic activity. Further, without being limited by a particular theory, immunomodulatory compounds disclosed herein may be capable of acting both indirectly through cytokine activation and directly on Natural Killer ("NK") cells and Natural Killer T ("NKT") cells, and increase the NK cells' ability to produce beneficial cytokines such as, but not limited to, IFN-γ, and to enhance NK and NKT cell cytotoxic activity.

Specific examples of immunomodulatory compounds include cyano and carboxy derivatives of substituted styrenes such as those disclosed in U.S. Pat. No. 5,929,117; 1-oxo-2-(2,6-dioxo-3-fluoropiperidin-3yl) isoindolines and 1,3-dioxo-2-(2,6-dioxo-3-fluoropiperidine-3-yl) isoindolines such as those described in U.S. Pat. Nos. 5,874,448 and 5,955,476; the tetra substituted 2-(2,6-dioxopiperdin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide), substituted 2-(2,6-dioxopiperidin-3-yl) phthalimides and substituted 2-(2,6-dioxopiperidin-3-yl)-1-oxoisoindoles including, but not limited to, those disclosed in U.S. Pat. Nos. 5,635,517, 6,281,230, 6,316,471, 6,403,613, 6,476,052 and 6,555,554; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; and isoindole-imide compounds such as those described in U.S. Publication No. 2003/0045552 published on Mar. 6, 2003, U.S. Publication No. 2003/0096841 published on May 22, 2003, and International Application No. PCT/US01/50401 (International Publication No. WO 02/059106). U.S. Publication No. 2006/0205787 describes 4-amino-2-(3-methyl-2,6-dioxopiperidin-3-yl)-isoindole-1,3-dione compositions. U.S. Publication No. 2007/0049618 describes isoindole-imide compounds. The entireties of each of the patents and patent applications identified herein are incorporated by reference. In one embodiment, immunomodulatory compounds do not include thalidomide.

Various immunomodulatory compounds disclosed herein contain one or more chiral centers, and can exist as racemic mixtures of enantiomers or mixtures of diastereomers. Thus, also provided herein is the use of stereomerically pure forms of such compounds, as well as the use of mixtures of those forms. For example, mixtures comprising equal or unequal amounts of the enantiomers of a particular immunomodulatory compounds may be used. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

Immunomodulatory compounds provided herein include, but are not limited to, 1-oxo- and 1,3 dioxo-2-(2,6-dioxopiperidin-3-yl) isoindolines substituted with amino in the benzo ring as described in U.S. Pat. No. 5,635,517 which is incorporated herein by reference.

These compounds have the structure I:

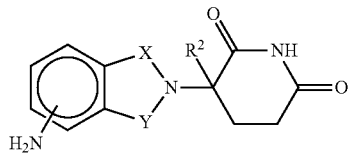

I in which one of X and Y is C=O the other of X and Y is C=O or CH$_2$, and R$^2$ is hydrogen or lower alkyl, in particular methyl. Specific immunomodulatory compounds include, but are not limited to:

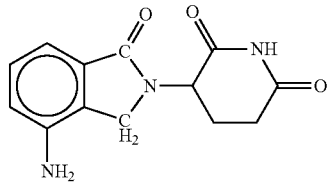

1-oxo-2-(2,6-dioxopiperidin-3-yl)-4-aminoisoindoline;

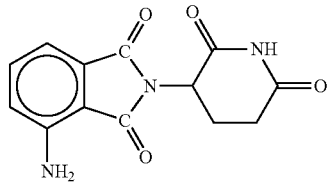

1,3-dioxo-2-(2,6-dioxopiperidin-3-yl)-4-aminoisoindoline; and

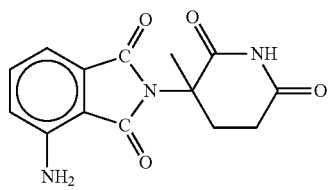

1,3-dioxo-2-(3-methyl-2,6-dioxopiperidin-3-yl)-4-aminoisoindole, and optically pure isomers thereof. Other immunomodulatory compounds useful in the methods described herein include thalidomide, lenalidomide, and pomalidomide. In one embodiment, the immunomodulatory compound is thalidomide. In one embodiment, the immunomodulatory compound is lenalidomide. In one embodiment, the immunomodulatory compound is pomalidomide.

The compounds can be obtained via standard, synthetic methods (see e.g., U.S. Pat. No. 5,635,517, incorporated herein by reference). The compounds are also available from Celgene Corporation, Warren, N.J.

Other specific immunomodulatory compounds belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Representative compounds are of formula:

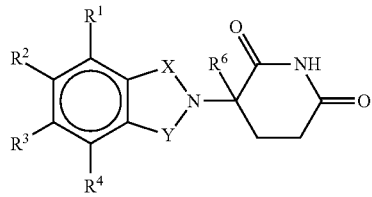

in which:

one of X and Y is C=O and the other of X and Y is C=O or CH$_2$;

(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;

R$^5$ is hydrogen or alkyl of 1 to 8 carbon atoms;

R$^6$ is hydrogen, alkyl of 1 to 8 carbon atoms, benzyl, or halo;

provided that R$^6$ is other than hydrogen if X and Y are C=O and (i) each of R$^1$, R$^2$, R$^3$, and R$^4$ is fluoro or (ii) one of R$^1$, R$^2$, R$^3$, or R$^4$ is amino.

Compounds representative of this class are of the formulas:

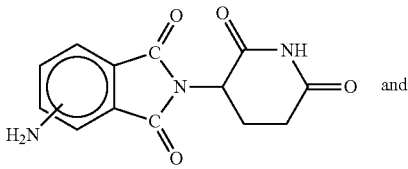 and

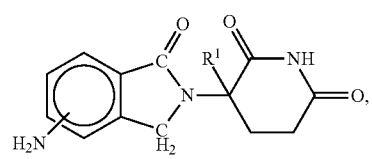

wherein R$^1$ is hydrogen or methyl. In a separate embodiment, provided herein is the use of enantiomerically pure forms (e.g. optically pure (R) or (S) enantiomers) of these compounds.

Still other specific immunomodulatory compounds disclosed herein belong to a class of isoindole-imides disclosed in U.S. Pat. No. 7,091,353, U.S. Patent Publication No. 2003/0045552, and International Application No. PCT/US01/50401 (International Publication No. WO 02/059106), each of which are incorporated herein by reference. Representative compounds are of formula II:

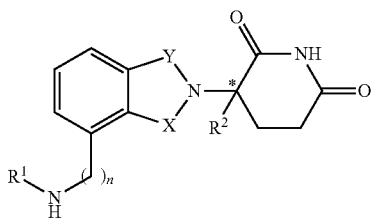

and pharmaceutically acceptable salts, hydrates, solvates, clathrates, enantiomers, diastereomers, racemates, and mixtures of stereoisomers thereof, wherein:
one of X and Y is C=O and the other is $CH_2$ or C=O;
$R^1$ is H, (C)alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(S)R^3$, $C(O)OR^4$, $(C_1-C_8)$alkyl-$N(R^6)2$, $(C_1-C_8)$alkyl-$OR^5$, $(C_1-C_8)$alkyl-$C(O)OR^5$, $C(O)NHR^3$, $C(S)NHR^3$, $C(O)NR^3R^3$, $C(S)NR^3R^{3'}$ or $(C_1-C_8)$alkyl-$O(CO)R^5$;
$R^2$ is H, F, benzyl, $(C_1-C_8)$alkyl, $(C_2-C_8)$alkenyl, or $(C_2-C_8)$alkynyl;
$R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_0-C_8)$alkyl-$N(R^6)2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;
$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$(C_1-C_6)$heterocycloalkyl, or $(C_0-C_4)$alkyl-$(C_2-C_5)$heteroaryl;
$R^5$ is $(C_1-C_8)$alkyl, $(C_2-C_8)$alkenyl, $(C_2-C_8)$alkynyl, benzyl, aryl, or $(C_2-C_5)$heteroaryl;
each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-$C(O)O-R^5$ or the $R^6$ groups can join to form a heterocycloalkyl group;
n is 0 or 1; and
* represents a chiral-carbon center.

In specific compounds of formula II, when n is 0 then $R^1$ is $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(S)NHR^3$, or $(C_1-C_8)$alkyl-$O(CO)R^5$;
$R^2$ is H or $(C_1-C_8)$alkyl; and
$R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_5-C_8)$alkyl-$N(R^6)2$; $(C_0-C_8)$alkyl-NH—$C(O)O—R^5$; $(C_1-C_8)$alkyl-$OR^5$, $(C_1-C_8)$alkyl-$C(O)OR^5$, $(C_1-C_8)$alkyl-$O(CO)R^5$, or $C(O)OR^5$; and the other variables have the same definitions.

In other specific compounds of formula II, $R^2$ is H or $(C_1-C_4)$alkyl.

In other specific compounds of formula II, le is $(C_1-C_8)$ alkyl or benzyl.

In other specific compounds of formula II, $R^1$ is H, $(C_1-C_8)$alkyl, benzyl, $CH_2OCH_3$, $CH_2CH_2OCH_3$, or

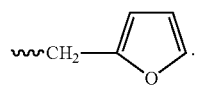

In another embodiment of the compounds of formula II, $R^1$ is

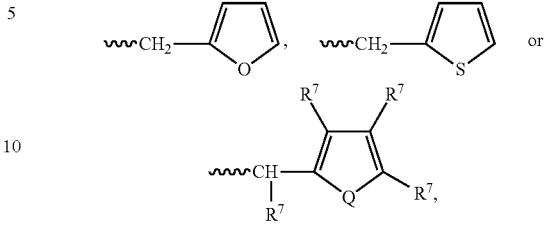

wherein Q is O or S, and each occurrence of $R^1$ is independently H, $(C_1-C_8)$alkyl, $(C_3-C_7)$cycloalkyl, $(C_2-C_8)$alkenyl, $(C_2-C_8)$alkynyl, benzyl, aryl, halogen, $(C_0-C_4)$alkyl-$(C_1-C_6)$ heterocycloalkyl, $(C_0-C_4)$alkyl-$(C_2-C_5)$heteroaryl, $(C_0-C_8)$ alkyl-$N(R^6)2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$, or adjacent occurrences of $R^1$ can be taken together to form a bicyclic alkyl or aryl ring.

In other specific compounds of formula II, $R^1$ is $C(O)R^3$.

In other specific compounds of formula II, $R^3$ is $(C_0-C_4)$ alkyl-$(C_2-C_5)$heteroaryl, $(C_1-C_8)$alkyl, aryl, or $(C_0-C_4)$alkyl-$OR^5$.

In other specific compounds of formula II, heteroaryl is pyridyl, furyl, or thienyl.

In other specific compounds of formula II, le is $C(O)OR^4$.

In other specific compounds of formula II, the H of C(O)NHC(O) can be replaced with $(C_1-C_4)$alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl) methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl) carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl] methyl}(octylamino)carboxamide; and N-{[2-(2,6-dioxo(3-piperidyl))-1,3-dioxoisoindolin-4-yl]methyl}(benzylamino) carboxamide.

Still other specific immunomodulatory compounds disclosed herein belong to a class of isoindole-imides disclosed in U.S. Patent Application Publication Nos. 2002/0045643, International Publication No. WO 98/54170, and U.S. Pat.

No. 6,395,754, each of which is incorporated herein by reference. Representative compounds are of formula III:

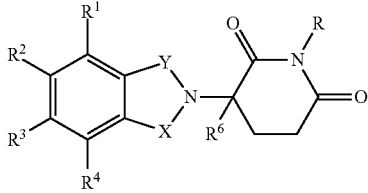

and pharmaceutically acceptable salts, hydrates, solvates, clathrates, enantiomers, diastereomers, racemates, and mixtures of stereoisomers thereof, wherein:
one of X and Y is C=O and the other is $CH_2$ or C=O;
R is H or $CH_2OCOR'$;
(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —$NHR^5$ and the remaining of $R^1$, $R^2$, $R^3$, or $R^4$ are hydrogen;
$R^5$ is hydrogen or alkyl of 1 to 8 carbons
$R^6$ hydrogen, alkyl of 1 to 8 carbon atoms, benzo, chloro, or fluoro;
R' is $R^7$—$CHR^{10}$—$N(R^8R^9)$;
$R^7$ is m-phenylene or p-phenylene or —$(CnH2n)$- in which n has a value of 0 to 4; each of $R^8$ and $R^9$ taken independently of the other is hydrogen or alkyl of 1 to 8 carbon atoms, or $R^8$ and $R^9$ taken together are tetramethylene, pentamethylene, hexamethylene,
or —$CH_2CH_2X^1CH_2CH_2$— in which $X^1$ is —O—, —S—, or —NH—;
$R^{10}$ is hydrogen, alkyl of to 8 carbon atoms, or phenyl; and
* represents a chiral-carbon center.
Other representative compounds are of formula:

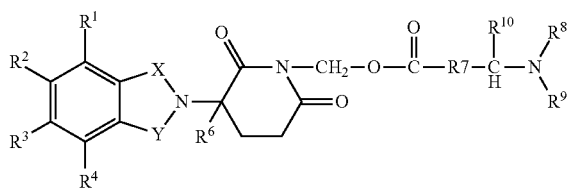

wherein:
one of X and Y is C=O and the other of X and Y is C=O or $CH_2$;
(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;
$R^5$ is hydrogen or alkyl of 1 to 8 carbon atoms;
$R^6$ is hydrogen, alkyl of 1 to 8 carbon atoms, benzo, chloro, or fluoro;
$R^7$ is m-phenylene or p-phenylene or —$(CnH2n)$- in which n has a value of 0 to 4;
each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X^1CH_2CH_2$— in which $X^1$ is —O—, —S—, or —NH—; and
$R^{10}$ is hydrogen, alkyl of to 8 carbon atoms, or phenyl.
Other representative compounds are of formula:

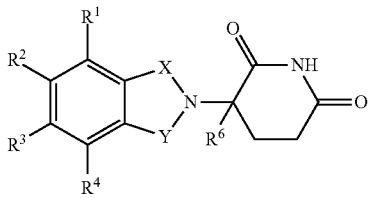

in which
one of X and Y is C=O and the other of X and Y is C=O or $CH_2$;
each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is nitro or protected amino and the remaining of $R^1$, $R^2$, $R^3$, and $R^4$ are hydrogen; and
$R^6$ is hydrogen, alkyl of 1 to 8 carbon atoms, benzo, chloro, or fluoro.
Other representative compounds are of formula:

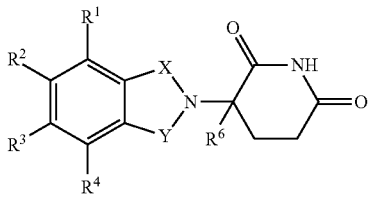

in which:
one of X and Y is C=O and the other of X and Y is C=O or $CH_2$;
(i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;
$R^5$ is hydrogen, alkyl of 1 to 8 carbon atoms, or CO—$R^7$—$CH(R^{10})NR^8R^9$ in which each of $R^7$, $R^8$, $R^9$, and $R^{10}$ is as herein defined; and
$R^6$ is alkyl of 1 to 8 carbon atoms, benzo, chloro, or fluoro.
Specific examples of the compounds are of formula:

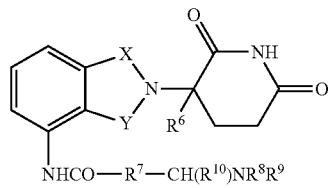

in which:
one of X and Y is C=O and the other of X and Y is C=O or $CH_2$;
$R^6$ is hydrogen, alkyl of 1 to 8 carbon atoms, benzyl, chloro, or fluoro;
$R^7$ is m-phenylene, p-phenylene or —$(CnH2n)$- in which n has a value of 0 to 4;
each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X^1CH_2CH_2$— in which $X^1$ is —O—, —S— or —NH—; and
$R^{10}$ is hydrogen, alkyl of 1 to 8 carbon atoms, or phenyl.

Other specific immunomodulatory compounds are 1-oxo-2-(2,6-dioxo-3-fluoropiperidin-3yl) isoindolines and 1,3-dioxo-2-(2,6-dioxo-3-fluoropiperidine-3-yl) isoindolines such as those described in U.S. Pat. Nos. 5,874,448 and 5,955,476, each of which is incorporated herein by reference. Representative compounds are of formula:

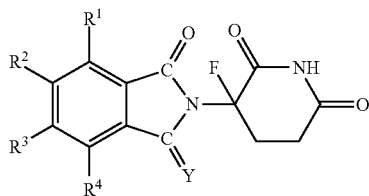

wherein:
Y is oxygen or $H_2$ and
each of $R^1$, $R^2$, $R^3$, and $R^4$, independently of the others, is hydrogen, halo, alkyl of 1 to 4 carbon atoms, alkoxy of 1 to 4 carbon atoms, or amino.

Other specific immunomodulatory compounds are the tetra substituted 2-(2,6-dioxopiperdin-3-yl)-1-oxoisoindolines described in U.S. Pat. No. 5,798,368, which is incorporated herein by reference. Representative compounds are of formula:

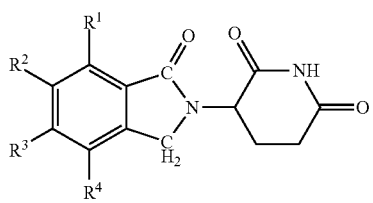

wherein each of $R^1$, $R^2$, $R^3$, and $R^4$, independently of the others, is halo, alkyl of 1 to 4 carbon atoms, or alkoxy of 1 to 4 carbon atoms.

Other specific immunomodulatory compounds are 1-oxo and 1,3-dioxo-2-(2,6-dioxopiperidin-3-yl) isoindolines disclosed in U.S. Pat. No. 6,403,613, which is incorporated herein by reference. Representative compounds are of formula:

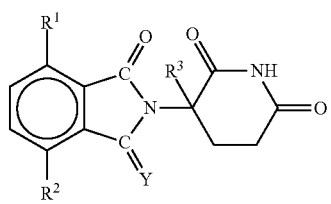

in which
Y is oxygen or $H_z$,
a first of $R^1$ and $R^2$ is halo, alkyl, alkoxy, alkylamino, dialkylamino, cyano, or carbamoyl, the second of $R^1$ and $R^2$, independently of the first, is hydrogen, halo, alkyl, alkoxy, alkylamino, dialkylamino, cyano, or carbamoyl, and
$R^3$ is hydrogen, alkyl, or benzyl.

Specific examples of the compounds are of formula:

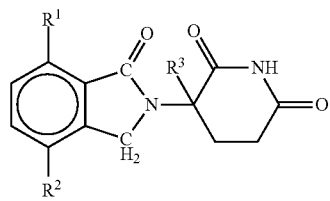

wherein
a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl; the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and
$R^3$ is hydrogen, alkyl of from 1 to 4 carbon atoms, or benzyl. Specific examples include, but are not limited to, 1-oxo-2-(2,6-dioxopiperidin-3-yl)-4-methylisoindoline.

Other representative compounds are of formula:

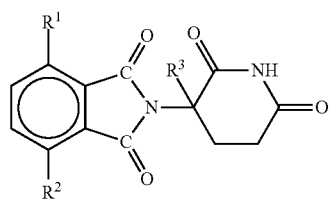

wherein:
a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl; the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and
$R^3$ is hydrogen, alkyl of from 1 to 4 carbon atoms, or benzyl.

Other specific immunomodulatory compounds disclosed herein are 1-oxo and 1,3-dioxoisoindolines substituted in the 4- or 5-position of the indoline ring described in U.S. Pat. No. 6,380,239 and U.S. Pat. No. 7,244,759, both of which are incorporated herein by reference. Representative compounds are of formula:

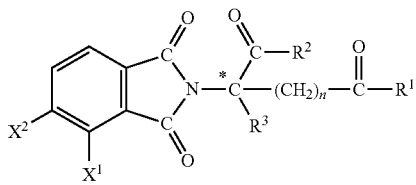

in which the carbon atom designated C* constitutes a center of chirality (when n is not zero and $R^1$ is not the same as $R^2$); one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if $X^1$ is amino, and n is 1 or 2, then $R^1$ and $R^2$ are not both hydroxy; and the salts thereof.

Further representative compounds are of formula:

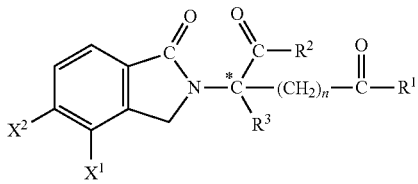

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl or an alkyl or acyl of one to six carbons; and n has a value of 0, 1, or 2.

Specific examples include, but are not limited to, 2-(4-amino-1-oxo-1,3-dihydro-isoindol-2-yl)-4-carbamoyl-butyric acid and 4-(4-amino-1-oxo-1,3-dihydro-isoindol-2-yl)-4-carbamoyl-butyric acid, which have the following structures, respectively, and pharmaceutically acceptable salts, solvates, prodrugs, and stereoisomers thereof:

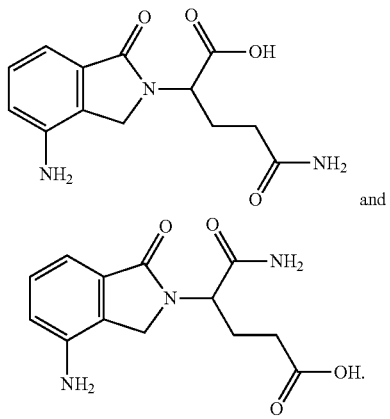

Other representative compounds are of formula:

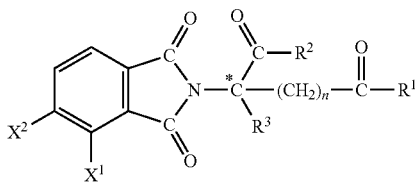

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl or acyl of one to six carbons; and n has a value of 0, 1, or 2; and the salts thereof.

Specific examples include, but are not limited to, 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptable salts, solvate, prodrugs, and stereoisomers thereof:

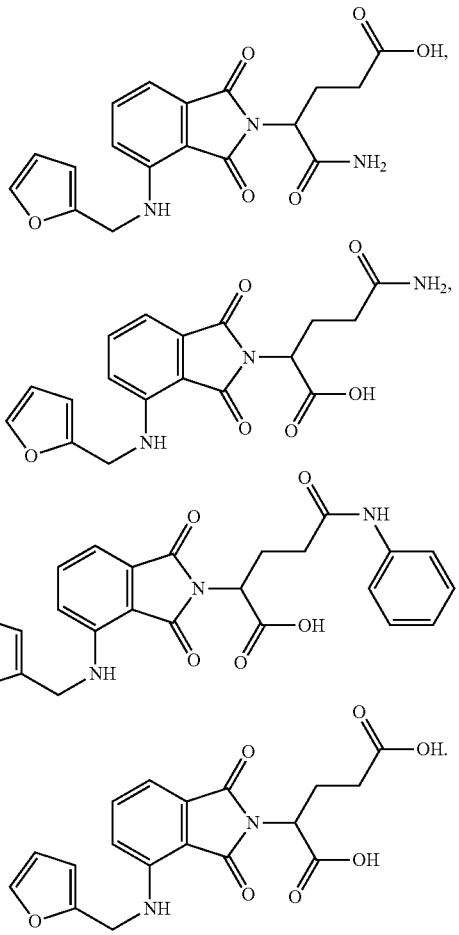

Other specific examples of the compounds are of formula:

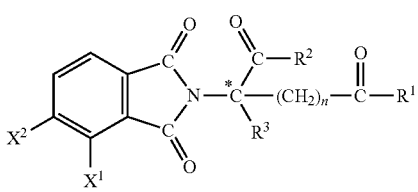

wherein:
one of $X^1$ and $X^2$ is nitro, or NH—Z, and the other of $X^1$ or $X^2$ is hydrogen;

each of $R^1$ and $R^2$, independent of the other, is hydroxy or NH—Z;

$R^3$ is alkyl of one to six carbons, halo, or hydrogen;

Z is hydrogen, phenyl, an acyl of one to six carbons, or an alkyl of one to six carbons; and n has a value of 0, 1, or 2; and if —$COR^2$ and —$(CH_2)_nCOR^1$ are different, the carbon atom designated C* constitutes a center of chirality.

Other representative compounds are of formula:

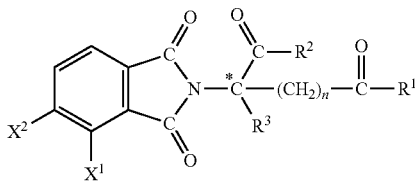

wherein:

one of $X^1$ and $X^2$ is alkyl of one to six carbons;

each of $R^1$ and $R^2$, independent of the other, is hydroxy or NH—Z;

$R^3$ is alkyl of one to six carbons, halo, or hydrogen;

Z is hydrogen, phenyl, an acyl of one to six carbons, or an alkyl of one to six carbons; and n has a value of 0, 1, or 2; and if —$COR^2$ and —$(CH_2)_nCOR^1$ are different, the carbon atom designated C* constitutes a center of chirality.

Still other specific immunomodulatory compounds are isoindoline-1-one and isoindoline-1,3-dione substituted in the 2-position with 2,6-dioxo-3-hydroxypiperidin-5-yl described in U.S. Pat. No. 6,458,810, which is incorporated herein by reference. Representative compounds are of formula:

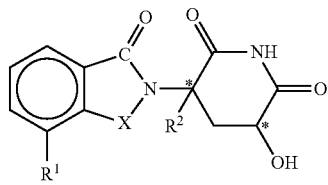

wherein:

the carbon atoms designated * constitute centers of chirality;

X is —C(O)— or —$CH_2$—;

$R^1$ is alkyl of 1 to 8 carbon atoms or —$NHR^3$;

$R^2$ is hydrogen, alkyl of 1 to 8 carbon atoms, or halogen; and $R^3$ is hydrogen, alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms, phenyl, unsubstituted or substituted with alkyl of 1 to 8 carbon atoms, alkoxy of 1 to 8 carbon atoms, halo, amino, or alkylamino of 1 to 4 carbon atoms, benzyl, unsubstituted or substituted with alkyl of 1 to 8 carbon atoms, alkoxy of 1 to 8 carbon atoms, halo, amino, or alkylamino of 1 to 4 carbon atoms, or —$COR^4$ in which $R^4$ is hydrogen, alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms, phenyl, unsubstituted or substituted with alkyl of 1 to 8 carbon atoms, alkoxy of 1 to 8 carbon atoms, halo, amino, or alkylamino of 1 to 4 carbon atoms, or benzyl, unsubstituted or substituted with alkyl of 1 to 8 carbon atoms, alkoxy of 1 to 8 carbon atoms, halo, amino, or alkylamino of 1 to 4 carbon atoms.

Other specific compounds provided herein are of formula:

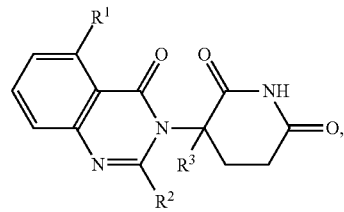

and pharmaceutically acceptable salts, solvates, and stereoisomers thereof, wherein:

$R^1$ is: hydrogen; halo; —($CH_2$)—OH; ($C_1$-$C_6$)alkyl, optionally substituted with one or more halo;

($C_1$-$C_6$)alkoxy, optionally substituted with one or more halo; or

—$(CH_2)_nNHR^a$, wherein $R^a$ is:

hydrogen;

($C_1$-$C_6$)alkyl, optionally substituted with one or more halo;

—$(CH_2)_n$-(6 to 10 membered aryl);

—C(O)—$(CH_2)_n$-(6 to 10 membered aryl) or —C(O)—$(CH_2)_n$-(6 to 10 membered heteroaryl), wherein the aryl or heteroaryl is optionally substituted with one or more of: halo; —$SCF_3$; ($C_1$-$C_6$)alkyl, itself optionally substituted with one or more halo; or ($C_1$-$C_6$)alkoxy, itself optionally substituted with one or more halo;

—C(O)—($C_1$-$C_8$)alkyl, wherein the alkyl is optionally substituted with one or more halo;

—C(O)—$(CH_2)_n$($C_3$-$C_{10}$-cycloalkyl);

—C(O)—$(CH_2)_n$—$NR^bR^c$, wherein $R^b$ and $R^c$ are each independently:

hydrogen;

($C_1$-$C_6$)alkyl, optionally substituted with one or more halo;

($C_1$-$C_6$)alkoxy, optionally substituted with one or more halo; or 6 to 10 membered aryl, optionally substituted with one or more of: halo; ($C_1$-$C_6$)alkyl, itself optionally substituted with one or more halo; or ($C_1$-$C_6$)alkoxy, itself optionally substituted with one or more halo;

—C(O)—$(CH_2)_n$—O—($C_1$-$C_6$)alkyl; or

—C(O)—$(CH_2)_n$—O—$(CH_2)_n$-(6 to 10 membered aryl);

$R^2$ is: hydrogen; —$(CH_2)_n$OH; phenyl; —O—($C_1$-$C_6$)alkyl; or ($C_1$-$C_6$)alkyl, optionally substituted with one or more halo;

$R^3$ is: hydrogen; or ($C_1$-$C_6$)alkyl, optionally substituted with one or more halo; and n is 0, 1, or 2.

Specific examples include, but are not limited to, 3-(5-amino-2-methyl-4-oxo-4H-quinazolin-3-yl)-piperidine-2,6-dione ("Compound A"), which has the following structure:

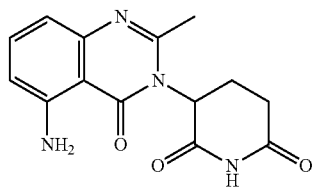

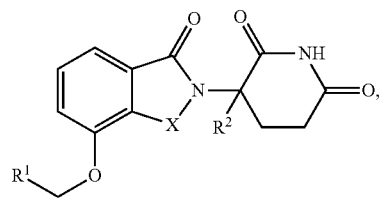

or an enantiomer or a mixture of enantiomers thereof; or a pharmaceutically acceptable salt, solvate, hydrate, co-crystal, clathrate, or polymorph thereof.

Compound A can be prepared as described in U.S. Pat. No. 7,635,700, the disclosure of which is incorporated herein by reference in its entirety. The compound can be also synthesized according to other methods apparent to those of skill in the art based upon the teaching herein. In certain embodiments, Compound A is in a crystalline form described in U.S. Provisional Pat. App. No. 61/451,806, filed Mar. 11, 2011, which is incorporated herein by reference in its entirety. In some embodiments, the hydrochloride salt of Compound A is used in the methods provided herein. Methods of treating, preventing and/or managing cancers and other diseases using Compound A are described in U.S. Provisional Pat. App. No. 61/451,995, filed Mar. 11, 2011, which is incorporated herein by reference in its entirety.

Specific examples include, but are not limited to pomalidomide, which has the following structure:

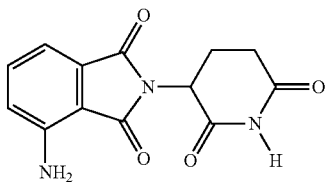 [SMILES: Nc1cccc2c1C(=O)N(C1CCC(=O)NC1=O)C2=O]

or an enantiomer or a mixture of enantiomers thereof; or a pharmaceutically acceptable salt, solvate, hydrate, co-crystal, clathrate, or polymorph thereof.

Pomalidomide can be obtained via standard, synthetic methods (see e.g., U.S. Pat. No. 5,635,517, incorporated herein by reference).

Specific examples include, but are not limited to lenalidomide, which has the following structure:

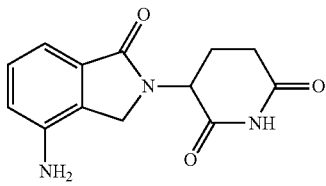 [SMILES: Nc1cccc2c1CN(C1CCC(=O)NC1=O)C2=O]

or an enantiomer or a mixture of enantiomers thereof; or a pharmaceutically acceptable salt, solvate, hydrate, co-crystal, clathrate, or polymorph thereof.

Lenalidomide can be prepared as described in WO2012/149299, the disclosure of which is incorporated herein by reference in its entirety. The compound can be also synthesized according to other methods apparent to those of skill in the art based upon the teaching herein.

Other specific compounds provided herein are of formula:

or a pharmaceutically acceptable salt, solvate or stereoisomer thereof, wherein:
X is C=O or $CH_2$;
$R^1$ is —Y—$R^3$;
$R^2$ is H or ($C_1$-$C_6$)alkyl;
Y is: 6 to 10 membered aryl, heteroaryl or heterocycle, each of which may be optionally substituted with one or more halogen; or a bond;
$R^3$ is: —$(CH_2)_n$-aryl, —O—$(CH_2)_n$-aryl or —$(CH_2)_n$—O-aryl, wherein the aryl is optionally substituted with one or more: ($C_1$-$C_6$)alkyl, itself optionally substituted with one or more halogen; ($C_1$-$C_6$)alkoxy, itself substituted with one or more halogen; oxo; amino; carboxyl; cyano; hydroxyl; halogen; deuterium; 6 to 10 membered aryl or heteroaryl, optionally substituted with one or more ($C_1$-$C_6$)alkyl, ($C_1$-$C_6$)alkoxy or halogen; —$CONH_2$; or —COO—($C_1$-$C_6$)alkyl, wherein the alkyl may be optionally substituted with one or more halogen;
—$(CH_2)_n$-heterocycle, —O—$(CH_2)_n$-heterocycle or —$(CH_2)_n$—O-heterocycle, wherein the heterocycle is optionally substituted with one or more: ($C_1$-$C_6$)alkyl, itself optionally substituted with one or more halogen; ($C_1$-$C_6$)alkoxy, itself substituted with one or more halogen; oxo; amino; carboxyl; cyano; hydroxyl; halogen; deuterium; 6 to 10 membered aryl or heteroaryl, optionally substituted with one or more ($C_1$-$C_6$)alkyl, ($C_1$-$C_6$)alkoxy or halogen; —$CONH_2$; or —COO—($C_1$-$C_6$)alkyl, wherein the alkyl may be optionally substituted with one or more halogen; or
—$(CH_2)_n$-heteroaryl, —O—$(CH_2)_n$-heteroaryl or —$(CH_2)_n$—O-heteroaryl, wherein the heteroaryl is optionally substituted with one or more: ($C_1$-$C_6$)alkyl, itself optionally substituted with one or more halogen; ($C_1$-$C_6$)alkoxy, itself substituted with one or more halogen; oxo; amino; carboxyl; cyano; hydroxyl; halogen; deuterium; 6 to 10 membered aryl or heteroaryl, optionally substituted with one or more ($C_1$-$C_6$)alkyl, ($C_1$-$C_6$)alkoxy or halogen; —$CONH_2$; or —COO—($C_1$-$C_6$)alkyl, wherein the alkyl may be optionally substituted with one or more halogen; and
n is 0, 1, 2 or 3.

All of the compounds described can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques. Additional information on immunomodulatory compounds, their preparation, and use can be found, for example, in U.S. Patent Application Publication Nos. 2006/0188475, 2006/0205787, and 2007/0049618, each of which is incorporated by reference herein in its entirety.

The compounds may be small organic molecules having a molecular weight less than about 1,000 g/mol, and are not proteins, peptides, oligonucleotides, oligosaccharides or other macromolecules.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

Methods of Treatment or Management

KSHV-Induced Lymphoma

Provided here is a method of treating or managing Kaposi's sarcoma-associated herpesvirus (KSHV) induced lymphoma, comprising identifying a patient having KSHV-induced lymphoma sensitive to treatment with an immunomodulatory compound; and administering to the patient a therapeutically effective amount of the compound. Provided here is a method of treating or managing Kaposi's sarcoma-associated herpesvirus (KSHV) induced lymphoma or lymphoproliferative disease, comprising identifying a patient having KSHV-induced lymphoma or lymphoproliferative disease sensitive to treatment with an immunomodulatory compound; and administering to the patient a therapeutically effective amount of the compound. In one embodiment, the immunomodulatory compound is 4-amino-2-(2,6-dioxopiperidin-3-yl)isoindoline-1,3-dione (pomalidomide). In another embodiment, the immunomodulatory compound is 3-(4-amino-1-oxo-1,3-dihydro-isoindol-2-yl)-piperidine-2,6-dione (lenalidomide). In another embodiment, the immunomodulatory compound is thalidomide.

In one embodiment provided herein is a method of treating or managing Kaposi's sarcoma-associated herpesvirus (KSHV) induced lymphoma (or lymphoproliferative disease), comprising: identifying a patient having KSHV-induced lymphoma sensitive to treatment pomalidomide, or a pharmaceutically acceptable salt, solvate or stereoisomer thereof; and administering to the patient a therapeutically effective amount of the compound.

In one embodiment provided herein is a method of treating or managing Kaposi's sarcoma-associated herpesvirus (KSHV) induced lymphoma, comprising: identifying a patient having KSHV-induced lymphoma sensitive to treatment lenalidomide or thalidomide, or a pharmaceutically acceptable salt, solvate or stereoisomer thereof; and administering to the patient a therapeutically effective amount of the compound. In one embodiment provided herein is a method of treating or managing Kaposi's sarcoma-associated herpesvirus (KSHV) induced lymphoma or lymphoproliferative disease, comprising: identifying a patient having KSHV-induced lymphoma or lymphoproliferative disease sensitive to treatment lenalidomide or thalidomide, or a pharmaceutically acceptable salt, solvate or stereoisomer thereof; and administering to the patient a therapeutically effective amount of the compound.

In one embodiment, the KSHV-induced lymphoma is a B-cell lymphoma. In one embodiment, the B-cell lymphoma is primary effusion lymphoma (PEL). In another embodiment, the B-cell lymphoma or lymphoproliferative disease is multicentric Castleman's disease (MCD).

In another aspect provided herein is a method of treating or managing Kaposi's sarcoma-associated herpesvirus (KSHV) induced lymphoma, comprising:
(i) identifying a patient having KSHV-induced lymphoma sensitive to treatment with pomalidomide or a pharmaceutically acceptable salt, solvate or stereoisomer thereof and
(ii) administering to the patient a therapeutically effective amount of the compound.

In another aspect provided herein is a method of treating or managing Kaposi's sarcoma-associated herpesvirus (KSHV) induced lymphoma or lymphoproliferative disease, comprising:
(i) identifying a patient having KSHV-induced lymphoma or lymphoproliferative disease sensitive to treatment with pomalidomide or a pharmaceutically acceptable salt, solvate or stereoisomer thereof; and
(ii) administering to the patient a therapeutically effective amount of the compound.

In one embodiment, the patient further has an immunodeficiency disease or disorder. In one embodiment, the patient is human immunodeficiency virus (HIV) positive. In another embodiment, the patient is human immunodeficiency virus (HIV) negative.

In one embodiment, the KSHV-induced lymphoma (or lymphoproliferative disease) is newly diagnosed, relapsed, refractory, or relapsed and refractory. In one embodiment, the patient has received previous therapy for KSHV-induced lymphoma (or lymphoproliferative disease). In one embodiment, the patient has received previous therapy for KSHV-induced lymphoma (or lymphoproliferative disease) and demonstrated progression on the previous therapy. In one embodiment, the previous therapy is treatment with cytotoxic chemotherapy, treatment with radiation therapy, treatment with an immunomodulatory compound, treatment with interferon, or treatment with local therapy. In one embodiment, the previous therapy is treatment with thalidomide, lenalidomide, or a combination thereof.

In one embodiment, identifying a patient having KSHV-induced lymphoma (or lymphoproliferative disease) sensitive to treatment with the compound comprises obtaining a biological sample from the patient. As used hereinbelow "the compound" refers to pomalidomide, lenalidomide, or thalidomide in the respective embodiments described herein.

In one embodiment, identifying a patient having KSHV-induced lymphoma (or lymphoproliferative disease) sensitive to treatment with the compound comprises measuring the level of a biomarker in a biological sample obtained from the patient. Such measuring can be performed using techniques known in the art.

In one embodiment, the biomarker is major histocompatibility complex class I (MHC-1). In one embodiment, a decreased level of MHC-1 relative to a control sample indicates a likelihood that the patient is sensitive to treatment with the compound. In one embodiment, the control sample is from a subject not infected with KSHV. In another embodiment, the control sample is a sample taken from the subject before administration of a compound described herein.

In one embodiment, the biomarker is p21.

In one embodiment, the biomarker is IRF4 or NF-κB.

In one embodiment, the gene expression level of the biomarker is measured. In one embodiment, the mRNA level of the biomarker is measured. In one embodiment, the DNA level of the biomarker is measured. Polynucleotides described herein can be measured using techniques known in the art. In another embodiment, the protein level of the biomarker is measured. Protein levels can be measured using techniques known in the art.

In one embodiment, the biological sample is a lymph node biopsy, a bone marrow biopsy, or a sample of peripheral blood tumor cells.

In one embodiment, pomalidomide is administered in an amount of from about 1 mg per day to about 5 mg per day. In one embodiment, pomalidomide is administered in an amount of about 1, 2, 3, 4, or 5 mg per day. In one embodiment, pomalidomide is administered in an amount of about 1 mg per day. In one embodiment, pomalidomide is administered in an amount of about 2 mg per day. In one embodiment, pomalidomide is administered in an amount of about 3 mg per day. In one embodiment, pomalidomide is administered in an amount of about 4 mg per day. In one embodiment, pomalidomide is administered in an amount of about 5 mg per day.

In one embodiment, pomalidomide is administered as a free base.

In one embodiment, pomalidomide is administered orally. In one embodiment, the compound is administered in a capsule or tablet.

In one embodiment, pomalidomide is administered for 21 consecutive days followed by seven consecutive days of rest in a 28 day cycle. In one embodiment, the 28 day cycle can be repeated as described herein, for example, 1, 2, 3, 4, 5, 6, 7, 8, 9, 10, 11, 12, or more times.

In one embodiment, lenalidomide is administered in an amount of from about 2.5 mg per day to about 25 mg per day. In one embodiment, lenalidomide is administered in an amount of about 2.5, 5 10, 15, or 25 mg per day.

In one embodiment, lenalidomide is administered orally. In one embodiment, the compound is administered in a capsule or tablet.

In one embodiment, lenalidomide is administered for 21 consecutive days followed by seven consecutive days of rest in a 28 day cycle. In one embodiment, the 28 day cycle can be repeated as described herein, for example, 1, 2, 3, 4, 5, 6, 7, 8, 9, 10, 11, 12, or more times.

Further provided herein is a method for predicting response to treatment in a patient having KSHV-induced lymphoma, comprising:
  (i) obtaining a biological sample from the patient;
  (ii) measuring the level of MHC-1 in the biological sample; and
  (iii) comparing the level of MHC-1 in the biological sample to that of a biological sample from a subject not infected with KSHV;
  wherein a decreased level of MHC-1 in the biological sample from the patient relative to that from the subject not infected with KSHV indicates a likelihood of an effective response to the treatment with pomalidomide or a pharmaceutically acceptable salt, solvate or stereoisomer thereof.

Further provided herein is a method for predicting response to treatment in a patient having KSHV-induced lymphoma or lymphoproliferative disease, comprising:
  (i) obtaining a biological sample from the patient;
  (ii) measuring the level of MHC-1 in the biological sample; and
  (iii) comparing the level of MHC-1 in the biological sample to that of a biological sample from a subject not infected with KSHV;
  wherein a decreased level of MHC-1 in the biological sample from the patient relative to that from the subject not infected with KSHV indicates a likelihood of an effective response to the treatment with pomalidomide or a pharmaceutically acceptable salt, solvate or stereoisomer thereof.

Further provided herein is a method for predicting response to treatment in a patient having KSHV-induced lymphoma or lymphoproliferative disease, comprising:
  (i) obtaining a biological sample from the patient;
  (ii) measuring the level of MHC-1 in the biological sample; and
  (iii) comparing the level of MHC-1 in the biological sample to that of a biological sample from a subject not infected with KSHV;
  wherein a decreased level of MHC-1 in the biological sample from the patient relative to that from the subject not infected with KSHV indicates a likelihood of an effective response to the treatment with lenalidomide or thalidomide, or a pharmaceutically acceptable salt, solvate or stereoisomer thereof.

Further provided herein is a method for predicting response to treatment in a patient having KSHV-induced lymphoma, comprising:
  (i) obtaining a biological sample from the patient;
  (ii) measuring the level of MHC-1 in the biological sample; and
  (iii) comparing the level of MHC-1 in the biological sample to that of a biological sample from a subject not infected with KSHV;
  wherein a decreased level of MHC-1 in the biological sample from the patient relative to that from the subject not infected with KSHV indicates a likelihood of an effective response to the treatment with lenalidomide or thalidomide, or a pharmaceutically acceptable salt, solvate or stereoisomer thereof.

Further provided herein is a method for predicting response to treatment in a patient having PEL, comprising:
  (i) obtaining a biological sample from the patient;
  (ii) measuring the level of MHC-1 in the biological sample; and
  (iii) comparing the level of MHC-1 in the biological sample a control sample;
  wherein a decreased level of MHC-1 in the biological sample from the patient relative to the control sample indicates a likelihood of an effective response to the treatment with pomalidomide, lenalidomide or thalidomide, or a pharmaceutically acceptable salt, solvate or stereoisomer thereof. In one embodiment, the method comprises treatment with pomalidomide. In one embodiment, the method comprises treatment with lenalidomide.

In another aspect provided herein is a method for monitoring response to treatment in a patient having KSHV-induced lymphoma, comprising:
  (i) obtaining a first biological sample from the patient;
  (ii) measuring the level of MHC-1 in the first biological sample;
  (iii) administering to the patient a therapeutically effective amount of pomalidomide or a pharmaceutically acceptable salt, solvate or stereoisomer thereof;
  (iv) obtaining a second biological sample from the patient;
  (v) measuring the level of MHC-1 in the second biological sample; and
  (vi) comparing the level of MHC-1 in the first biological sample to that in the second biological sample; and
  wherein an increased level of MHC-1 in the second biological sample relative to the first biological sample indicates a likelihood of an effective response.

In another aspect provided herein is a method for monitoring response to treatment in a patient having KSHV-induced lymphoma or lymphoproliferative disease, comprising:
  (i) obtaining a first biological sample from the patient;
  (ii) measuring the level of MHC-1 in the first biological sample;
  (iii) administering to the patient a therapeutically effective amount of pomalidomide or a pharmaceutically acceptable salt, solvate or stereoisomer thereof;
  (iv) obtaining a second biological sample from the patient;

(v) measuring the level of MHC-1 in the second biological sample; and (vi) comparing the level of MHC-1 in the first biological sample to that in the second biological sample; and wherein an increased level of MHC-1 in the second biological sample relative to the first biological sample indicates a likelihood of an effective response.

In another aspect provided herein is a method for monitoring response to treatment in a patient having KSHV-induced lymphoma, comprising:

(i) obtaining a first biological sample from the patient;

(ii) measuring the level of MHC-1 in the first biological sample;

(iii) administering to the patient a therapeutically effective amount of a lenalidomide or thalidomide, or a pharmaceutically acceptable salt, solvate or stereoisomer thereof;

(iv) obtaining a second biological sample from the patient;

(v) measuring the level of MHC-1 in the second biological sample; and (vi) comparing the level of MHC-1 in the first biological sample to that in the second biological sample; and wherein an increased level of MHC-1 in the second biological sample relative to the first biological sample indicates a likelihood of an effective response.

In another aspect provided herein is a method for monitoring response to treatment in a patient having KSHV-induced lymphoma or lymphoproliferative disease, comprising:

(i) obtaining a first biological sample from the patient;

(ii) measuring the level of MHC-1 in the first biological sample;

(iii) administering to the patient a therapeutically effective amount of a lenalidomide or thalidomide, or a pharmaceutically acceptable salt, solvate or stereoisomer thereof;

(iv) obtaining a second biological sample from the patient;

(v) measuring the level of MHC-1 in the second biological sample; and (vi) comparing the level of MHC-1 in the first biological sample to that in the second biological sample; and wherein an increased level of MHC-1 in the second biological sample relative to the first biological sample indicates a likelihood of an effective response.

In another aspect provided herein is a method for monitoring patient compliance with treatment with pomalidomide or a pharmaceutically acceptable salt, solvate or stereoisomer thereof, in a patient having KSHV-induced lymphoma, comprising:

(i) obtaining a biological sample from the patient;

(ii) measuring the level of MHC-1 in the biological sample; and (iii) comparing the level of MHC-1 in the biological sample to a control untreated sample;

wherein an increased level of MHC-1 in the biological sample relative to the control untreated sample indicates patient compliance with the treatment.

In another aspect provided herein is a method for monitoring patient compliance with treatment with pomalidomide or a pharmaceutically acceptable salt, solvate or stereoisomer thereof, in a patient having KSHV-induced lymphoma or lymphoproliferative disease, comprising:

(i) obtaining a biological sample from the patient;

(ii) measuring the level of MHC-1 in the biological sample; and (iii) comparing the level of MHC-1 in the biological sample to a control untreated sample;

wherein an increased level of MHC-1 in the biological sample relative to the control untreated sample indicates patient compliance with the treatment.

In certain embodiments, the method is a method for monitoring patient compliance with treatment with lenalidomide or thalidomide, or a pharmaceutically acceptable salt, solvate or stereoisomer thereof, in a patient having KSHV-induced lymphoma, comprising:

(i) obtaining a biological sample from the patient;

(ii) measuring the level of MHC-1 in the biological sample; and (iii) comparing the level of MHC-1 in the biological sample to a control untreated sample;

wherein an increased level of MHC-1 in the biological sample relative to the control untreated sample indicates patient compliance with the treatment.

In certain embodiments, the method is a method for monitoring patient compliance with treatment with lenalidomide or thalidomide, or a pharmaceutically acceptable salt, solvate or stereoisomer thereof, in a patient having KSHV-induced lymphoma or lymphoproliferative disease, comprising:

(i) obtaining a biological sample from the patient;

(ii) measuring the level of MHC-1 in the biological sample; and (iii) comparing the level of MHC-1 in the biological sample to a control untreated sample;

wherein an increased level of MHC-1 in the biological sample relative to the control untreated sample indicates patient compliance with the treatment.

Also provided herein are methods of treating or managing KSHV-induced lymphoma (or lymphoproliferative disease) with an immunomodulatory compound provided herein or elsewhere. Also provided herein are methods of preventing KSHV-induced lymphoma (or lymphoproliferative disease) with an immunomodulatory compound provided herein or elsewhere. In one embodiment, the immunomodulatory compound is pomalidomide. In another embodiment, the immunomodulatory compound is lenalidomide.

In one embodiment, provided herein is a method of treating or managing KSHV-induced lymphoma (or lymphoproliferative disease) in a patient having KSHV-induced lymphoma (or lymphoproliferative disease), comprising administering to the patient a therapeutically effective amount of 4-amino-2-(2,6-dioxopiperidin-3-yl)isoindoline-1,3-dione.

In one embodiment, provided herein is a method of treating or managing KSHV-induced lymphoma (or lymphoproliferative disease) in a patient having KSHV-induced lymphoma, comprising administering to the patient a therapeutically effective amount of lenalidomide.

In one embodiment, provided herein is a method of treating or managing KSHV-induced lymphoma (or lymphoproliferative disease) in a patient having KSHV-induced lymphoma, comprising administering to the patient a therapeutically effective amount of thalidomide.

In one embodiment, provided herein is a method of treating or managing KSHV-induced lymphoma (or lymphoproliferative disease) in a patient having KSHV-induced lymphoma, comprising administering to the patient a therapeutically effective amount of 4-amino-2-(2,6-dioxopiperidin-3-yl)isoindoline-1,3-dione, wherein the patient further has an immunodeficiency disease or disorder, e.g., the patient is human immunodeficiency virus (HIV) positive.

In one embodiment, provided herein is a method of treating or managing KSHV-induced lymphoma (or lymphoproliferative disease) in a patient having KSHV-induced lymphoma (or lymphoproliferative disease), comprising administering to the patient a therapeutically effective amount of lenalidomide, wherein the patient further has an immunodeficiency disease or disorder, e.g., the patient is human immunodeficiency virus (HIV) positive.

In one embodiment, provided herein is a method of treating or managing KSHV-induced lymphoma (or lymphoproliferative disease) in a patient having KSHV-induced lymphoma, comprising administering to the patient a therapeutically effective amount of thalidomide, wherein the patient further has an immunodeficiency disease or disorder, e.g., the patient is human immunodeficiency virus (HIV) positive.

In one embodiment, provided herein is a method of treating or managing KSHV-induced lymphoma (or lymphoproliferative disease), which comprises administering to a patient having KSHV-induced lymphoma (or lymphoproliferative disease) from about 1 mg to about 5 mg per day of pomalidomide or a pharmaceutically acceptable salt, solvate or stereoisomer thereof, wherein pomalidomide is administered in one or more cycles, each of which comprises administering pomalidomide for a period of time followed by a period of rest.

In one embodiment, provided herein is a method of treating or managing KSHV-induced lymphoma (or lymphoproliferative disease), which comprises administering to a patient having KSHV-induced lymphoma from about 2.5 mg to about 25 mg per day of lenalidomide or a pharmaceutically acceptable salt, solvate or stereoisomer thereof, wherein lenalidomide is administered in one or more cycles, each of which comprises administering lenalidomide for a period of time followed by a period of rest.

In one embodiment, the patient further has an immunodeficiency disease or disorder. In one embodiment, the patient is human immunodeficiency virus (HIV) positive. In another embodiment, the patient is human immunodeficiency virus (HIV) negative.

In one embodiment, the KSHV-induced lymphoma is a B-cell lymphoma. In one embodiment, the B-cell lymphoma is primary effusion lymphoma (PEL). In another embodiment, the B-cell lymphoma or lymphoproliferative disease is multicentric Castleman's disease (MCD).

In one embodiment, the KSHV-induced lymphoma or lymphoproliferative disease is an advanced KSHV-induced lymphoma or lymphoproliferative disease.

In one embodiment, the KSHV-induced lymphoma or lymphoproliferative disease is newly diagnosed, relapsed, refractory, or relapsed and refractory.

In one embodiment, the patient has received previous therapy for KSHV-induced lymphoma or lymphoproliferative disease. In one embodiment, the patient has received previous therapy for KSHV-induced lymphoma or lymphoproliferative disease and demonstrated progression on the previous therapy. In one embodiment, the previous therapy is treatment with cytotoxic chemotherapy, treatment with radiation therapy, treatment with an immunomodulatory compound, treatment with interferon, or treatment with local therapy. In one embodiment, the previous therapy is treatment with thalidomide, lenalidomide, or a combination thereof.

In one embodiment, pomalidomide is administered in an amount of about 5 mg per day. In one embodiment, pomalidomide is administered in an amount of about 4 mg per day. In one embodiment, pomalidomide is administered in an amount of about 3 mg per day. In one embodiment, pomalidomide is administered in an amount of about 2 mg per day. In one embodiment, pomalidomide is administered in an amount of about 1 mg per day.

In one embodiment, pomalidomide is administered as a free base.

In one embodiment, pomalidomide is administered orally.

In one embodiment, pomalidomide is administered in a capsule. In one embodiment, the capsule comprises pomalidomide, mannitol, and pre-gelatinized starch. In one embodiment, the capsule comprises an amount of about 1 mg, 2 mg, 3 mg, 4 mg, or 5 mg of the compound.

In one embodiment, pomalidomide is administered in a tablet.

In one embodiment, lenalidomide is administered in an amount of from about 2.5 mg per day to about 25 mg per day. In one embodiment, lenalidomide is administered in an amount of about 2.5, 5 10, 15, or 25 mg per day.

In one embodiment, lenalidomide is administered orally. In one embodiment, the compound is administered in a capsule or tablet.

In one embodiment, lenalidomide is administered for 21 consecutive days followed by seven consecutive days of rest in a 28 day cycle. In one embodiment, the 28 day cycle can be repeated as described herein, for example, 1, 2, 3, 4, 5, 6, 7, 8, 9, 10, 11, 12, or more times.

In one embodiment, one cycle comprises three to six weeks.

In one embodiment, pomalidomide is administered for 21 consecutive days followed by seven consecutive days of rest in a 28 day cycle. In one embodiment, pomalidomide is orally administered in an amount of 5 mg per day for 21 consecutive days followed by seven consecutive days of rest in a 28 day cycle.

In one embodiment, pomalidomide is administered for 14 consecutive days followed by seven consecutive days of rest in a 21 day cycle. In one embodiment, pomalidomide is orally administered in an amount of 5 mg per day for 14 consecutive days followed by seven consecutive days of rest in a 21 day cycle.

Without being limited by a particular theory, administration of pomalidomide to a patient having KSHV-induced lymphoma or lymphoproliferative disease augments immune responsiveness in the patient. In one embodiment, provided herein is a method of improving immune responsiveness in a patient having KSHV-induced lymphoma, comprising administering to the patient a therapeutically effective amount of pomalidomide.

In one embodiment, provided herein is a method of increasing numbers of peripheral T-cells in a patient having KSHV-induced lymphoma (or lymphoproliferative disease), comprising administering to the patient a therapeutically effective amount of pomalidomide.

In one embodiment, provided herein is a method of increasing numbers of peripheral T-cells in a patient having KSHV-induced lymphoma (or lymphoproliferative disease), comprising administering to the patient a therapeutically effective amount of lenalidomide or thalidomide.

In one embodiment, provided herein is a method of increasing numbers of CD4 or CD8 T-cells in a patient having KSHV-induced lymphoma (or lymphoproliferative disease), comprising administering to the patient a therapeutically effective amount of pomalidomide.

In one embodiment, provided herein is a method of increasing numbers of CD4 or CD8 T-cells in a patient having KSHV-induced lymphoma (or lymphoproliferative disease), comprising administering to the patient a therapeutically effective amount of lenalidomide or thalidomide.

In one embodiment, the CD4 or CD8 T-cells are peripheral CD4 or CD8 T-cells.

In one embodiment, provided herein is a method of increasing the proportion of activated T-cells in a patient having KSHV-induced lymphoma (or lymphoproliferative disease), comprising administering to the patient a therapeutically effective amount of pomalidomide.

In one embodiment, provided herein is a method of increasing the proportion of activated T-cells in a patient having KSHV-induced lymphoma (or lymphoproliferative disease), comprising administering to the patient a therapeutically effective amount of lenalidomide or thalidomide.

In one embodiment, the activated T-cells are characterized with one or more of CD38+, HLADR+ and DR+/38+. In one embodiment, the increase in the proportion of central memory phenotypes T-cells is assessed by the number of RO+27+ cells.

In one embodiment, provided herein is a method of decreasing the number of senescent T cells in a patient having KSHV-induced lymphoma (or lymphoproliferative disease), comprising administering to the patient a therapeutically effective amount of pomalidomide.

In one embodiment, provided herein is a method of decreasing the number of senescent T cells in a patient having KSHV-induced lymphoma (or lymphoproliferative disease), comprising administering to the patient a therapeutically effective amount of lenalidomide or thalidomide.

In one embodiment, the decrease in the number of senescent T cells is assessed by the number of CD57+ cells. In one embodiment, provided herein is a method of increasing the proportion of central memory phenotypes T-cells in a patient having KSHV-induced lymphoma (or lymphoproliferative disease), comprising administering to the patient a therapeutically effective amount of pomalidomide.

In one embodiment, the increase in the proportion of central memory phenotypes T-cells is assessed by the number of RO+27+ cells.

In one embodiment, provided herein is a method of decreasing the proportion of naive T-cells in a patient having KSHV-induced lymphoma (or lymphoproliferative disease), comprising administering to the patient a therapeutically effective amount of pomalidomide. In one embodiment, the decrease in the proportion of naive T-cells is assessed by the number of RO-27+ cells. In one embodiment, the patient is human immunodeficiency virus (HIV) positive. In another embodiment, the patient is human immunodeficiency virus (HIV) negative.

In one embodiment, provided herein is a method of treating or managing a disorder or condition where augmentation of T cell responses would be of benefit, comprising administering to the patient a therapeutically effective amount of pomalidomide. The disorders or conditions include, but are not limited to, Kaposi sarcoma, other cancers (both caused by viruses and not caused by viruses); pre-malignancies; acute and chronic viral diseases including HIV infection; other infectious diseases; or immunodeficiencies. Augmentation of T cell responses includes augmenting responses to vaccines.

Also provided herein is a method of treating or managing an acute or chronic viral disease or viral induced tumor, the method comprising administering to the patient a therapeutically effective amount of pomalidomide. In one embodiment, is a method of treating or managing an acute or chronic viral disease or viral induced tumor, the method comprising administering to the patient a therapeutically effective amount of lenalidomide or thalidomide. In one embodiment, the viral disease is an HIV infection.

In one embodiment, without being limited by a particular theory, administration of pomalidomide to a patient having KSHV-induced lymphoma (or lymphoproliferative disease) results in an increased level of MHC-1 in the patient relative to a control untreated sample. In one embodiment, without being limited by a particular theory, administration of pomalidomide to a patient having KSHV-induced lymphoma (or lymphoproliferative disease) results in reduction of down-regulation of MHC-1 caused by KSHV in the patient relative to a control untreated sample.

Without being limited by a particular theory, administration of pomalidomide to a patient having KSHV-induced lymphoma (or lymphoproliferative disease) prevents the suppression of surface MHC-1 that is caused by KSHV. In one embodiment, provided herein is a method of preventing the suppression of surface MHC-1 that is caused by KSHV in a patient having KSHV-induced lymphoma (or lymphoproliferative disease), comprising administering to the patient a therapeutically effective amount of pomalidomide.

In one embodiment, provided herein is a method of treating or managing a disorder or condition where enhancement of MHC-1 expression, or reversal of its suppression by a virus (e.g., KSHV), would be beneficial. The disorders or conditions include, but are not limited to, tumors caused by oncogenic viruses; acute or chronic viral infections; intracellular bacterial infections; tumors in which there is decreased expression of MHC-1, or immunodeficiency diseases in which there is decreased expression of MHC-1 or in which increased expression would be beneficial.

In one embodiment, without being limited by a particular theory, administration of pomalidomide to a patient having KSHV-induced lymphoma results in an increased p21 level in the patient relative to a control untreated sample.

In one embodiment, without being limited by a particular theory, administration of pomalidomide to a patient having KSHV-induced lymphoma results in a decreased IRF4 or NF-κB level in the patient relative to a control untreated sample.

In certain embodiments, methods provided herein further comprise administering a therapeutically effective amount of an additional active agent.

In one embodiment, the additional active agent is doxorubicin. In one embodiment, the doxorubicin is liposomal doxorubicin.

In one embodiment, doxorubicin is administered intravenously. In one embodiment, from about 10 mg/m$^2$ to about 25 mg/m$^2$ doxorubicin is administered. In one embodiment, about 15 mg/m$^2$ doxorubicin is administered. In another embodiment, about 20 mg/m$^2$ doxorubicin is administered.

In one embodiment, doxorubicin is administered once on day 1 of a 21 day cycle.

In one embodiment, doxorubicin is administered intravenously once on day 1 and the compound is administered orally once per day on days 1 through 14 of a 21-day cycle.

In one embodiment, pomalidomide is administered orally in an amount of 2 mg per day for 14 consecutive days followed by seven consecutive days of rest in a 21 day cycle and doxorubicin is administered intravenously in an amount of 15 mg/m$^2$ once on day 1 of a 21 day cycle.

In one embodiment, pomalidomide is administered orally in an amount of 2 mg per day for 14 consecutive days followed by seven consecutive days of rest in a 21 day cycle and doxorubicin is administered intravenously in an amount of 20 mg/m$^2$ once on day 1 of a 21 day cycle.

In one embodiment, pomalidomide is administered orally in an amount of 3 mg per day for 14 consecutive days followed by seven consecutive days of rest in a 21 day cycle and doxorubicin is administered intravenously in an amount of 20 mg/m² once on day 1 of a 21 day cycle.

In one embodiment, pomalidomide is administered orally in an amount of 5 mg per day for 14 consecutive days followed by seven consecutive days of rest in a 21 day cycle and doxorubicin is administered intravenously in an amount of 20 mg/m² once on day 1 of a 21 day cycle.

In one embodiment, lenalidomide is administered orally in an amount of 2.5 mg per day for 21 consecutive days followed by seven consecutive days of rest in a 28 day cycle and a second active agent is administered as described herein. In one embodiment, the second active agent is administered in accordance with a package insert. The term "package insert" refers to instructions customarily comprised in commercial packages of medicaments approved by the FDA or a similar regulatory agency of a country other than the USA, which contains information about, for example, the usage, dosage, administration, contraindications, and/or warnings concerning the use of such medicaments.

In one embodiment, lenalidomide is administered orally in an amount of 5 mg per day for 21 consecutive days followed by seven consecutive days of rest in a 28 day cycle and a second active agent is administered as described herein. In one embodiment, the second active agent is administered in accordance with a package insert.

In one embodiment, lenalidomide is administered orally in an amount of 10 mg day for 21 consecutive days followed by seven consecutive days of rest in a 28 day cycle and a second active agent is administered as described herein. In one embodiment, the second active agent is administered in accordance with a package insert.

In one embodiment, lenalidomide is administered orally in an amount of 15 mg day for 21 consecutive days followed by seven consecutive days of rest in a 28 day cycle and a second active agent is administered as described herein. In one embodiment, the second active agent is administered in accordance with a package insert.

In one embodiment, lenalidomide is administered orally in an amount of 25 mg per day for 21 consecutive days followed by seven consecutive days of rest in a 28 day cycle and a second active agent is administered as described herein. In one embodiment, the second active agent is administered in accordance with a package insert.

In one embodiment, the additional active agent is PD-1 inhibitor. A "PD-1 inhibitor" refers to a moiety (e.g., compound, nucleic acid, polypeptide, antibody) that decreases, inhibits, blocks, abrogates or interferes with the activity or expression of PD-1 (e.g., Programmed Cell Death Protein 1; PD-1 (CD279); GI: 145559515), including variants, isoforms, species homologs of human PD-1 (e.g., mouse). A PD-1 inhibitor includes molecules and macromolecules such as, for example, compounds, nucleic acids, polypeptides, antibodies, peptibodies, diabodies, minibodies, nanobodies, single-chain variable fragments (ScFv), and functional fragments or variants thereof. A PD-1 inhibitor as used herein can refer to any moiety that antagonizes PD-1 activity or expression. In one embodiment, a PD-1 inhibitor is a monoclonal antibody.

In one embodiment, the PD-1 inhibitor is selected from the group consisting of nivolumab, pembrolizumab, pidilizumab, REGN2810, PDR 001, AMP-224, and MEDI0680.

In one embodiment, the PD-1 inhibitor is administered in an amount of about 0.1 mg/kg to about 10 mg/kg. In one embodiment, the PD-1 inhibitor is administered in an amount of about 0.5 mg/kg to about 5 mg/kg. In one embodiment, the PD-1 inhibitor is administered in an amount of about: 1 mg/kg, 2 mg/kg, 3 mg/kg, or 5 mg/kg.

In one embodiment, the additional active agent is a PD-L1 inhibitor. A "PD-L1 inhibitor" refers to a moiety (e.g., compound, nucleic acid, polypeptide, antibody) that decreases, inhibits, blocks, abrogates or interferes with the activity or binding of PD-L1 to its receptor, PD-1, or expression of PD-L1 (e.g., Programmed Cell Death 1 Ligand; PD-L1 (CD274); GI: 30088843), including variants, isoforms, species homologs of human PD-L1 (e.g., mouse). A PD-L1 inhibitor includes molecules and macromolecules such as, for example, compounds (small molecule compounds), nucleic acids, polypeptides, antibodies, peptibodies, diabodies, minibodies, single-domain antibodies or nanobodies, single-chain variable fragments (ScFv), and fragments or variants thereof. A PD-L1 inhibitor as used herein can refer to any moiety that antagonizes PD-L1 activity, its binding to PD-1, or its expression. In one embodiment, a PD-L1 inhibitor is a monoclonal antibody.

In one embodiment, the PD-L1 inhibitor is selected from the group consisting of durvalumab, avelumab, atezolizumab, and BMS-936559.

In one embodiment, the PD-L1 inhibitor is administered an amount of about 0.1 mg/kg to about 30 mg/kg. In one embodiment, the PD-L1 inhibitor is administered an amount of about 0.5 mg/kg to about 15 mg/kg. In one embodiment, the PD-L1 inhibitor is administered an amount of about: 0.1 mg/kg, 0.3 mg/kg, 1 mg/kg, 2 mg/kg, 3 mg/kg, 5 mg/kg, 10 mg/kg, or 20 mg/kg.

Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties. Further non-limiting examples include agents known in the art such as "nivolumab," "pembrolizumab," "pidilizumab," "AMP-224," "REGN2810," "PDR 001," "MEDI0680," "durvalumab," "avelumab," "atezolizumab," "BMS-936559," "STI-A1010," "STI-A1011," "STI-A1012," "STI-A1013," "STI-A1014," and "STI-A1015" which are herein used in accordance with their plain and ordinary meaning as understood in the art.

In one embodiment the additional active agent is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 inhibitor is tremelimumab (also known as ticilimumab or CP-675,206). In another embodiment, the anti-CTLA-4 inhibitor is ipilimumab (also known as MDX-010 or MDX-101). Ipilimumab is a fully human monoclonal IgG antibody that binds to CTLA-4. Ipilimumab is marketed under the trade name Yervoy™.

Kaposi's Sarcoma

Provided here is a method of treating or managing Kaposi's sarcoma, comprising identifying a patient having Kaposi's sarcoma sensitive to treatment with an immunomodulatory compound; and administering to the patient a therapeutically effective amount of the compound. In one embodiment, the immunomodulatory compound is 4-amino-2-(2,6-dioxopiperidin-3-yl)isoindoline-1,3-dione (pomalidomide). In another embodiment, the immunomodulatory compound is 3-(4-amino-1-oxo-1,3-dihydro-isoindol- 2-yl)-piperidine-2,6-dione (lenalidomide). In another embodiment, the immunomodulatory compound is thalidomide.

KS can be found in individuals with altered cellular immunity, including those with HIV, transplant recipients, and the elderly. A decreasing CD4 count can be associated with increasing risk of KS in patients with or without HIV, and treatment of HIV with antiretroviral therapy (ART) can decrease the risk of KS. Patients with KS can have decreased KSHV-specific T-cell responses when compared to KSHV-infected individuals without KS. Increases in KSHV-specific T-cell responses can be found in patients with HIV-associated KS treated with ART. Increases in KSHV-specific T-cell responses can be found in patients with HIV-associated KS in transplant recipients whose KS regressed with reduced immunosuppression.

In patients with HIV-associated KS, ART is the foundation of therapy. HIV control can allow restoration of KSHV-directed cellular immunity. For patients with HIV-associated KS whose response to ART is incomplete, liposomal anthracycline and/or paclitaxel can be administered. Therapy in HIV-uninfected subjects can include cytotoxic agents.

In one embodiment, provided here is a method of treating or managing Kaposi's sarcoma, comprising:

(i) identifying a patient having Kaposi's sarcoma sensitive to treatment with pomalidomide or a pharmaceutically acceptable salt, solvate or stereoisomer thereof; and (ii) administering to the patient a therapeutically effective amount of pomalidomide.

In one embodiment, provided here is a method of treating or managing Kaposi's sarcoma, comprising: identifying a patient having Kaposi's sarcoma sensitive to treatment with a lenalidomide or thalidomide, or a pharmaceutically acceptable salt, solvate or stereoisomer thereof; and administering to the patient a therapeutically effective amount of lenalidomide or thalidomide.

In one embodiment, the patient further has an immunodeficiency disease or disorder. In one embodiment, the patient is human immunodeficiency virus (HIV) positive. In another embodiment, the patient is human immunodeficiency virus (HIV) negative.

In one embodiment, the patient further has KSHV-associated multicentric Castleman's disease (MCD) or KSHV Inflammatory Cytokine Syndrome (KICS).

In one embodiment, the Kaposi's sarcoma is an advanced Kaposi's sarcoma.

In one embodiment, the Kaposi's sarcoma is newly diagnosed, relapsed, refractory, or relapsed and refractory. In one embodiment, the patient has received previous therapy for Kaposi's sarcoma. In one embodiment, the patient has received previous therapy for Kaposi's sarcoma and demonstrated progression on the previous therapy. In one embodiment, the previous therapy is treatment with cytotoxic chemotherapy, treatment with radiation therapy, treatment with an immunomodulatory compound, treatment with interferon, or treatment with local therapy. In one embodiment, the previous therapy is treatment with thalidomide, lenalidomide, or a combination thereof.

In one embodiment, identifying a patient having Kaposi's sarcoma sensitive to treatment with pomalidomide comprises obtaining a biological sample from the patient.

In one embodiment, identifying a patient having Kaposi's sarcoma sensitive to treatment with pomalidomide comprises measuring the level of a biomarker in a biological sample obtained from the patient.

In one embodiment, the biomarker is major histocompatibility complex class I (MHC-1). In one embodiment, a decreased level of MHC-1 relative to a control sample indicates a likelihood that the patient is sensitive to treatment with the compound. In one embodiment, the control sample is from a subject not infected with KSHV.

In one embodiment, the biomarker is p21.

In one embodiment, the biomarker is IRF4 or NF-κB.

In one embodiment, the gene expression level of the biomarker is measured. In one embodiment, the mRNA level of the biomarker is measured. In one embodiment, the DNA level of the biomarker is measured. In another embodiment, the protein level of the biomarker is measured.

In one embodiment, the biological sample is a lymph node biopsy, a bone marrow biopsy, or a sample of peripheral blood tumor cells.

In one embodiment, pomalidomide is administered in an amount of from about 1 mg per day to about 5 mg per day. In one embodiment, pomalidomide is administered in an amount of about 1, 2, 3, 4, or 5 mg per day.

In one embodiment, pomalidomide is administered as a free base.

In one embodiment, pomalidomide is administered orally. In one embodiment, the compound is administered in a capsule or tablet.

In one embodiment, pomalidomide is administered for 21 consecutive days followed by seven consecutive days of rest in a 28 day cycle.

In one embodiment, provided herein is a method for predicting response to treatment in a patient having Kaposi's sarcoma, comprising:

(i) obtaining a biological sample from the patient;

(ii) measuring the level of MHC-1 in the biological sample; and (iii) comparing the level of MHC-1 in the biological sample to that of a biological sample from a subject not infected with KSHV;

wherein a decreased level of MHC-1 in the biological sample from the patient relative to that from the subject not infected with KSHV indicates a likelihood of an effective response to the treatment with pomalidomide or a pharmaceutically acceptable salt, solvate or stereoisomer thereof.

In one embodiment, provided herein is a method for monitoring response to treatment in a patient having Kaposi's sarcoma, comprising:

(i) obtaining a first biological sample from the patient;

(ii) measuring the level of MHC-1 in the first biological sample;

(iii) administering to the patient a therapeutically effective amount of pomalidomide, or a pharmaceutically acceptable salt, solvate or stereoisomer thereof;

(iv) obtaining a second biological sample from the patient;

(v) measuring the level of MHC-1 in the second biological sample; and (vi) comparing the level of MHC-1 in the first biological sample to that in the second biological sample;

wherein an increased level of MHC-1 in the second biological sample relative to the first biological sample indicates a likelihood of an effective response.

In one embodiment, provided herein is a method for monitoring response to treatment in a patient having Kaposi's sarcoma, comprising:

(i) obtaining a first biological sample from the patient;

(ii) measuring the level of MHC-1 in the first biological sample;

(iii) administering to the patient a therapeutically effective amount of lenalidomide or thalidomide, or a pharmaceutically acceptable salt, solvate or stereoisomer thereof;

(iv) obtaining a second biological sample from the patient;

(v) measuring the level of MHC-1 in the second biological sample; and (vi) comparing the level of MHC-1 in the first biological sample to that in the second biological sample;

wherein an increased level of MHC-1 in the second biological sample relative to the first biological sample indicates a likelihood of an effective response.

In one embodiment, provided herein is a method for monitoring patient compliance with treatment with pomalidomide or a pharmaceutically acceptable salt, solvate or stereoisomer thereof, in a patient having Kaposi's sarcoma, comprising:

(i) obtaining a biological sample from the patient;

(ii) measuring the level of MHC-1 in the biological sample; and (iii) comparing the level of MHC-1 in the biological sample to a control untreated sample;

wherein an increased level of MHC-1 in the biological sample relative to the control untreated sample indicates patient compliance with the treatment.

In one embodiment, provided herein is a method for monitoring patient compliance with treatment with lenalidomide or thalidomide or a pharmaceutically acceptable salt, solvate or stereoisomer thereof, in a patient having Kaposi's sarcoma, comprising:

(i) obtaining a biological sample from the patient;

(ii) measuring the level of MHC-1 in the biological sample; and (iii) comparing the level of MHC-1 in the biological sample to a control untreated sample;

wherein an increased level of MHC-1 in the biological sample relative to the control untreated sample indicates patient compliance with the treatment.

Provided herein are methods of treating or managing Kaposi's sarcoma with an immunomodulatory compound provided herein or elsewhere. Also provided herein are methods of preventing Kaposi's sarcoma with an immunomodulatory compound provided herein or elsewhere. In one embodiment, the immunomodulatory compound is pomalidomide. In another embodiment, the immunomodulatory compound is lenalidomide. In another embodiment, the immunomodulatory compound is thalidomide.

In one embodiment, provided herein is a method of treating or managing Kaposi's sarcoma, which comprises administering to a patient having Kaposi's sarcoma from about 1 mg to about 5 mg per day of pomalidomide or a pharmaceutically acceptable salt, solvate or stereoisomer thereof, wherein pomalidomide is administered in one or more cycles, each of which comprises administering pomalidomide for a period of time followed by a period of rest.

In one embodiment, provided herein is a method of treating or managing Kaposi's sarcoma, which comprises administering to a patient having Kaposi's sarcoma from about 2.5 mg to about 25 mg per day of lenalidomide or a pharmaceutically acceptable salt, solvate or stereoisomer thereof, wherein lenalidomide is administered in one or more cycles, each of which comprises administering lenalidomide for a period of time followed by a period of rest.

In one embodiment, the patient further has an immunodeficiency disease or disorder. In one embodiment, the patient is human immunodeficiency virus (HIV) positive. In another embodiment, the patient is human immunodeficiency virus (HIV) negative.

In one embodiment, pomalidomide is administered in an amount of about 5 mg per day. In one embodiment, pomalidomide is administered in an amount of about 4 mg per day. In one embodiment, pomalidomide is administered in an amount of about 3 mg per day. In one embodiment, pomalidomide is administered in an amount of about 2 mg per day. In one embodiment, pomalidomide is administered in an amount of about 1 mg per day.

In one embodiment, pomalidomide is administered as a free base.

In one embodiment, pomalidomide is administered orally.

In one embodiment, pomalidomide is administered in a capsule. In one embodiment, the capsule comprises pomalidomide, mannitol, and pre-gelatinized starch. In one embodiment, the capsule comprises an amount of about 1 mg, 2 mg, 3 mg, 4 mg, or 5 mg of the compound.

In one embodiment, pomalidomide is administered in a tablet.

In one embodiment, one cycle comprises three to six weeks.

In one embodiment, pomalidomide is administered for 21 consecutive days followed by seven consecutive days of rest in a 28 day cycle. In one embodiment, pomalidomide is orally administered in an amount of 5 mg per day for 21 consecutive days followed by seven consecutive days of rest in a 28 day cycle.

In one embodiment, pomalidomide is administered for 14 consecutive days followed by seven consecutive days of rest in a 21 day cycle. In one embodiment, pomalidomide is orally administered in an amount of 5 mg per day for 14 consecutive days followed by seven consecutive days of rest in a 21 day cycle.

In one embodiment, lenalidomide is administered in an amount of from about 2.5 mg per day to about 25 mg per day. In one embodiment, lenalidomide is administered in an amount of about 2.5, 5 10, 15, or 25 mg per day.

In one embodiment, lenalidomide is administered orally. In one embodiment, the compound is administered in a capsule or tablet.

In one embodiment, lenalidomide is administered for 21 consecutive days followed by seven consecutive days of rest in a 28 day cycle. In one embodiment, the 28 day cycle can be repeated as described herein, for example, 1, 2, 3, 4, 5, 6, 7, 8, 9, 10, 11, 12, or more times.

In one embodiment, lenalidomide is administered orally in an amount of 2.5 mg per day for 21 consecutive days followed by seven consecutive days of rest in a 28 day cycle and a second active agent is administered as described herein. In one embodiment, the second active agent is administered in accordance with a package insert. The term package insert refers to instructions customarily comprised in commercial packages of medicaments approved by the FDA or a similar regulatory agency of a country other than the USA, which contains information about, for example, the usage, dosage, administration, contraindications, and/or warnings concerning the use of such medicaments.

In one embodiment, lenalidomide is administered orally in an amount of 5 mg per day for 21 consecutive days followed by seven consecutive days of rest in a 28 day cycle and a second active agent is administered as described herein. In one embodiment, the second active agent is administered in accordance with a package insert.

In one embodiment, lenalidomide is administered orally in an amount of 10 mg day for 21 consecutive days followed by seven consecutive days of rest in a 28 day cycle and a second active agent is administered as described herein. In one embodiment, the second active agent is administered in accordance with a package insert.

In one embodiment, lenalidomide is administered orally in an amount of 15 mg day for 21 consecutive days followed by seven consecutive days of rest in a 28 day cycle and a second active agent is administered as described herein. In one embodiment, the second active agent is administered in accordance with a package insert.

In one embodiment, lenalidomide is administered orally in an amount of 25 mg per day for 21 consecutive days followed by seven consecutive days of rest in a 28 day cycle and a second active agent is administered as described herein. In one embodiment, the second active agent is administered in accordance with a package insert.

Without being limited by a particular theory, administration of pomalidomide to a patient having Kaposi's sarcoma arguments immune responsiveness in the patient. In one embodiment, provided herein is a method of improving immune responsiveness in a patient having Kaposi's sarcoma, comprising administering to the patient a therapeutically effective amount of pomalidomide.

In one embodiment, provided herein is a method of increasing numbers of peripheral T-cells in a patient having Kaposi's sarcoma, comprising administering to the patient a therapeutically effective amount of pomalidomide.

In one embodiment, provided herein is a method of increasing numbers of CD4 or CD8 T-cells in a patient having Kaposi's sarcoma, comprising administering to the patient a therapeutically effective amount of pomalidomide. In one embodiment, the CD4 or CD8 T-cells are peripheral CD4 or CD8 T-cells.

In one embodiment, provided herein is a method of increasing the proportion of activated T-cells in a patient having Kaposi's sarcoma, comprising administering to the patient a therapeutically effective amount of pomalidomide. In one embodiment, the activated T-cells are characterized with one or more of CD38+, HLADR+ and DR+/38+.

In one embodiment, provided herein is a method of decreasing the number of senescent T cells in a patient having Kaposi's sarcoma, comprising administering to the patient a therapeutically effective amount of pomalidomide. In one embodiment, the decrease in the number of senescent T cells is assessed by the number of CD57+ cells.

In one embodiment, provided herein is a method of increasing the proportion of central memory phenotypes T-cells in a patient having Kaposi's sarcoma, comprising administering to the patient a therapeutically effective amount of pomalidomide. In one embodiment, the increase in the proportion of central memory phenotypes T-cells is assessed by the number of RO+27+ cells.

In one embodiment, provided herein is a method of decreasing the proportion of naive T-cells in a patient having Kaposi's sarcoma, comprising administering to the patient a therapeutically effective amount of pomalidomide. In one embodiment, the decrease in the proportion of naive T-cells is assessed by the number of RO−27+ cells. In one embodiment, the patient is human immunodeficiency virus (HIV) positive. In another embodiment, the patient is human immunodeficiency virus (HIV) negative.

In one embodiment, provided herein is a method of improving immune responsiveness in a patient having Kaposi's sarcoma, comprising administering to the patient a therapeutically effective amount of lenalidomide.

In one embodiment, provided herein is a method of increasing numbers of peripheral T-cells in a patient having Kaposi's sarcoma, comprising administering to the patient a therapeutically effective amount of lenalidomide.

In one embodiment, provided herein is a method of increasing numbers of CD4 or CD8 T-cells in a patient having Kaposi's sarcoma, comprising administering to the patient a therapeutically effective amount of lenalidomide. In one embodiment, the CD4 or CD8 T-cells are peripheral CD4 or CD8 T-cells.

In one embodiment, provided herein is a method of increasing the proportion of activated T-cells in a patient having Kaposi's sarcoma, comprising administering to the patient a therapeutically effective amount of lenalidomide. In one embodiment, the activated T-cells are characterized with one or more of CD38+, HLADR+ and DR+/38+.

In one embodiment, provided herein is a method of decreasing the number of senescent T cells in a patient having Kaposi's sarcoma, comprising administering to the patient a therapeutically effective amount of lenalidomide. In one embodiment, the decrease in the number of senescent T cells is assessed by the number of CD57+ cells.

In one embodiment, provided herein is a method of increasing the proportion of central memory phenotypes T-cells in a patient having Kaposi's sarcoma, comprising administering to the patient a therapeutically effective amount of lenalidomide. In one embodiment, the increase in the proportion of central memory phenotypes T-cells is assessed by the number of RO+27+ cells.

In one embodiment, provided herein is a method of decreasing the proportion of naive T-cells in a patient having Kaposi's sarcoma, comprising administering to the patient a therapeutically effective amount of lenalidomide. In one embodiment, the decrease in the proportion of naive T-cells is assessed by the number of RO−27+ cells. In one embodiment, the patient is human immunodeficiency virus (HIV) positive. In another embodiment, the patient is human immunodeficiency virus (HIV) negative.

In one embodiment, method provided herein further comprises administering a therapeutically effective amount of an additional active agent.

In one embodiment, the additional active agent is doxorubicin. In one embodiment, the doxorubicin is liposomal doxorubicin.

In one embodiment, doxorubicin is administered intravenously. In one embodiment, from about 10 mg/m$^2$ to about 25 mg/m$^2$ doxorubicin is administered. In one embodiment, about 15 mg/m$^2$ doxorubicin is administered. In another embodiment, about 20 mg/m$^2$ doxorubicin is administered.

In one embodiment, doxorubicin is administered once on day 1 of a 21 day cycle.

In one embodiment, doxorubicin is administered intravenously once on day 1 and the compound is administered orally once per day on days 1 through 14 of a 21-day cycle.

In one embodiment, the additional active agent is a PD-1 inhibitor. In one embodiment, the PD-1 inhibitor is selected from the group consisting of nivolumab, pembrolizumab, pidilizumab, REGN2810, PDR 001, AMP-224, and MEDI0680.

In one embodiment, the PD-1 inhibitor is administered in an amount of about 0.1 mg/kg to about 10 mg/kg. In one embodiment, the PD-1 inhibitor is administered in an amount of about 0.5 mg/kg to about 5 mg/kg. In one embodiment, the PD-1 inhibitor is administered in an amount of about: 1 mg/kg, 2 mg/kg, 3 mg/kg, or 5 mg/kg. In one embodiment, the PD-1 inhibitor is administered in accordance with a package insert.

In one embodiment, the additional active agent is a PD-L1 inhibitor. In one embodiment, the PD-L1 inhibitor is selected from the group consisting of durvalumab, avelumab, atezolizumab, and BMS-936559.

In one embodiment, the PD-L1 inhibitor is administered an amount of about 0.1 mg/kg to about 30 mg/kg. In one embodiment, the PD-L1 inhibitor is administered an amount of about 0.5 mg/kg to about 15 mg/kg. In one embodiment, the PD-L1 inhibitor is administered an amount of about: 0.1 mg/kg, 0.3 mg/kg, 1 mg/kg, 2 mg/kg, 3 mg/kg, 5 mg/kg, 10 mg/kg, or 20 mg/kg. In one embodiment, the PD-L1 inhibitor is administered in accordance with a package insert.

Further provided herein are methods of treating or managing Kaposi's sarcoma with an immunomodulatory compound provided herein or elsewhere in combination with doxorubicin. Also provided herein are methods of preventing Kaposi's sarcoma with an immunomodulatory compound provided herein or elsewhere in combination with doxorubicin. In one embodiment, the immunomodulatory compound is 4-amino-2-(2,6-dioxopiperidin-3-yl)isoindoline-1,3-dione (pomalidomide). In another embodiment, the immunomodulatory compound is lenalidomide.

In one embodiment, provided herein is a method of treating or managing Kaposi's sarcoma in a patient having Kaposi's sarcoma, comprising administering to the patient a therapeutically effective amount of 4-amino-2-(2,6-dioxopiperidin-3-yl)isoindoline-1,3-dione (pomalidomide) in combination with a therapeutically effective amount of doxorubicin.

In one embodiment, provided herein is a method of treating or managing Kaposi's sarcoma, which comprises administering to a patient having Kaposi's sarcoma from about 1 mg to about 5 mg per day of pomalidomide or a pharmaceutically acceptable salt, solvate or stereoisomer thereof, in combination with a therapeutically effective amount of doxorubicin, wherein the compound is administered in one or more cycles, each of which comprises administering the compound for a period of time followed by a period of rest.

In one embodiment, provided herein is a method of treating or managing Kaposi's sarcoma, which comprises administering to a patient having Kaposi's sarcoma a therapeutically effective amount of pomalidomide, or a pharmaceutically acceptable salt, solvate or stereoisomer thereof, in combination with a therapeutically effective amount of doxorubicin, wherein the compound is administered for 14 consecutive days followed by seven consecutive days of rest in a 21 day cycle and doxorubicin is administered once on day 1 of a 21 day cycle.

In one embodiment, pomalidomide is administered in an amount of from about 1 mg to about 5 mg per day for 14 consecutive days followed by seven consecutive days of rest in a 21 day cycle. In one embodiment, pomalidomide is orally administered in an amount of 5 mg per day for 14 consecutive days followed by seven consecutive days of rest in a 21 day cycle.

In one embodiment, the doxorubicin is liposomal doxorubicin.

In one embodiment, doxorubicin is administered intravenously. In one embodiment, from about 10 mg/m$^2$ to about 25 mg/m$^2$ doxorubicin is administered. In one embodiment, about 15 mg/m$^2$ doxorubicin is administered. In another embodiment, about 20 mg/m$^2$ doxorubicin is administered.

In one embodiment, pomalidomide is administered orally in an amount of 2 mg per day for 14 consecutive days followed by seven consecutive days of rest in a 21 day cycle and doxorubicin is administered intravenously in an amount of 15 mg/m$^2$ once on day 1 of a 21 day cycle.

In one embodiment, pomalidomide is administered orally in an amount of 2 mg per day for 14 consecutive days followed by seven consecutive days of rest in a 21 day cycle and doxorubicin is administered intravenously in an amount of 20 mg/m$^2$ once on day 1 of a 21 day cycle.

In one embodiment, pomalidomide is administered orally in an amount of 3 mg per day for 14 consecutive days followed by seven consecutive days of rest in a 21 day cycle and doxorubicin is administered intravenously in an amount of 20 mg/m$^2$ once on day 1 of a 21 day cycle.

In one embodiment, pomalidomide is administered orally in an amount of 5 mg per day for 14 consecutive days followed by seven consecutive days of rest in a 21 day cycle and doxorubicin is administered intravenously in an amount of 20 mg/m$^2$ once on day 1 of a 21 day cycle.

In one embodiment, the additional active agent is a PD-1 inhibitor. In one embodiment, the PD-1 inhibitor is selected from the group consisting of nivolumab, pembrolizumab, pidilizumab, REGN2810, PDR 001, AMP-224, and MEDI0680.

In one embodiment, the PD-1 inhibitor is administered in an amount of about 0.1 mg/kg to about 10 mg/kg. In one embodiment, the PD-1 inhibitor is administered in an amount of about 0.5 mg/kg to about 5 mg/kg. In one embodiment, the PD-1 inhibitor is administered in an amount of about: 1 mg/kg, 2 mg/kg, 3 mg/kg, or 5 mg/kg.

In one embodiment, the additional active agent is a PD-L1 inhibitor. In one embodiment, the PD-L1 inhibitor is selected from the group consisting of durvalumab, avelumab, atezolizumab, and BMS-936559.

In one embodiment, the PD-L1 inhibitor is administered an amount of about 0.1 mg/kg to about 30 mg/kg. In one embodiment, the PD-L1 inhibitor is administered an amount of about 0.5 mg/kg to about 15 mg/kg. In one embodiment, the PD-L1 inhibitor is administered an amount of about: 0.1 mg/kg, 0.3 mg/kg, 1 mg/kg, 2 mg/kg, 3 mg/kg, 5 mg/kg, 10 mg/kg, or 20 mg/kg.

Combination Therapy

One or more second active ingredients can be used in the methods and compositions provided herein together with an immunomodulatory compound provided herein. Specific second active agents can stimulate the division and differentiation of committed erythroid progenitors in cells in vitro or in vivo. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions provided herein include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

The use of native, naturally occurring, and recombinant proteins are provided herein. This disclosure further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Large molecule active agents may be administered in the form of anti-cancer vaccines. For example, vaccines that secrete, or cause the secretion of, cytokines such as IL-2, G-CSF, and GM-CSF can be used in the methods, pharmaceutical compositions, and kits provided herein. See, e.g., Emens, L. A., et al., *Curr. Opinion Mol. Ther.* 3(1):77-84 (2001).

In one embodiment, the large molecule active agent reduces, eliminates, or prevents an adverse effect associated with the administration of an immunomodulatory compound. Depending on the particular immunomodulatory compound and the disease or disorder begin treated, adverse effects can include, but are not limited to, drowsiness and somnolence, dizziness and orthostatic hypotension, neutropenia, infections that result from neutropenia, increased HIV-viral load, bradycardia, Stevens-Johnson Syndrome and toxic epidermal necrolysis, and seizures (e.g., grand mal convulsions). A specific adverse effect is neutropenia.

Antibodies that can be used in combination with oral formulations disclosed herein include monoclonal and polyclonal antibodies. Examples of antibodies include, but are not limited to, trastuzumab (Herceptin®), rituximab (Rituxan®), bevacizumab (Avastin™) pertuzumab (Omnitarg™), tositumomab (Bexxar®), edrecolomab (Panorex®), G250, elotuzumab, and daratumumab. Oral formulations disclosed herein can also comprise, be combined with, or used in combination with anti-TNF-α antibodies.

Second active agents that are small molecules can also be used to alleviate adverse effects associated with the administration of an immunomodulatory compound. However, like some large molecules, many are believed to be capable of providing a synergistic effect when administered with (e.g., before, after or simultaneously) an immunomodulatory compound. Examples of small molecule second active agents include, but are not limited to, anti-cancer agents, antibiotics, immunosuppressive agents, and steroids.

Examples of anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A;

bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®), O$^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors (e.g., bortezomib, carfilzomib, and ixazomib); protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, azacitidine, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Iressa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin)(Doxil®), paclitaxel, ganciclovir, adriamycin, estramustine sodium phosphate (Emcyt®), sulindac, and etoposide.

In one embodiment, the second active agent is doxorubicin (Adriamycin). In a specific embodiment, the second active agent is liposomal form of doxorubicin, or pegylated liposomal form of doxorubicin (Doxil®). In one embodiment, the second active agent is dexamethasone (Decadron®). In one embodiment, the second active agent is nivolumab (Opdivo®). In one embodiment, the second active agent is pembrolizumab (Keytruda). In one embodiment, the second active agent is pidilizumab. In one embodiment, the second active agent is durvalumab. In one embodiment, the second active agent is avelumab. In one embodiment, the second active agent is atezolizumab (Tecentriq®).

Administration of the immunomodulatory compounds and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for an immunomodulatory compound is orally. Preferred routes of administration for the second active agents or ingredients provided herein are known to those of ordinary skill in the art. See, e.g., *Physicians' Desk Reference*, 1755-1760 (56$^{th}$ ed., 2002).

The second active agent can be administered orally, intravenously or subcutaneously and once or twice daily in an amount of from about 1 to about 1500 mg, from about 5 to about 500 mg, from about 10 to about 350 mg, or from about 50 to about 200 mg. In other embodiments, the second active agent can be administered intravenously in an amount of from about 0.1 mg/kg to about 50 mg/kg, from about 0.1 mg/kg to about 30 mg/kg, from about 0.5 to about 15 mg/kg from about 1 to about 50 mg/kg, from about 1 to about 30 mg/kg, from about 1 to about 20 mg/kg, from about 1 to about 10 mg/kg or from about 5 to about 30 mg/kg. In one embodiment, the second active agent is administered intravenously in an amount of about 0.1 mg/kg, 0.3 mg/kg, 1 mg/kg, 2 mg/kg, 3 mg/kg, 5 mg/kg, 10 mg/kg, 15 mg/kg, 20 mg/kg, 30 mg/kg, or 50 mg/kg. The specific amount of the second active agent will depend on the specific agent used, the type of disease being treated or managed, the severity and stage of disease, and the amount(s) of immunomodulatory compounds provided herein and any optional additional active agents concurrently administered to the patient.

Provided herein is a method of increasing the dosage of a drug or agent that can be safely and effectively administered to a patient, which comprises administering to a patient (e.g., a human) an immunomodulatory compound, or a pharmaceutically acceptable derivative, salt, solvate, clathrate, hydrate, or prodrug thereof. Patients that can benefit by this method are those likely to suffer from an adverse effect associated with anti-cancer drugs for treating KS. The administration of an immunomodulatory compound alleviates or reduces adverse effects which are of such severity that it would otherwise limit the amount of anti-cancer drug.

In one embodiment, an immunomodulatory compound can be administered orally and daily in an amount of from about 0.1 to about 150 mg, and from about 1 to about 50 mg, or from about 2 to about 25 mg prior to, during, or after the occurrence of the adverse effect associated with the administration of an anti-cancer drug to a patient. In a particular embodiment, an immunomodulatory compound provided herein is administered further in combination with specific agents such as heparin, aspirin, coumadin, or G-CSF to avoid adverse effects that are associated with anti-cancer drugs such as but not limited to neutropenia or thrombocytopenia.

In one embodiment, an immunomodulatory compound can be administered to patients with KS in combination with additional active ingredients including but not limited to anti-cancer drugs, anti-inflammatories, antihistamines, antibiotics, and steroids.

In another embodiment, a method of treating, or managing KS, which comprises administering an immunomodulatory compound, or a pharmaceutically acceptable salt, solvate, hydrate, stereoisomer, clathrate, or prodrug thereof, in conjunction with (e.g. before, during, or after) conventional therapy including, but not limited to, surgery, immunotherapy, biological therapy, radiation therapy, or other non-drug based therapy presently used to treat or manage KS. The combined use of the immunomodulatory compound and conventional therapy may provide a unique treatment regimen that is unexpectedly effective in certain patients. Without being limited by theory, it is believed that immunomodulatory compounds may provide additive or synergistic effects when given concurrently with conventional therapy.

As discussed elsewhere herein, a method of reducing, treating and/or preventing adverse or undesired effects associated with conventional therapy including, but not limited to, surgery, chemotherapy, radiation therapy, hormonal therapy, biological therapy and immunotherapy. One or more immunomodulatory compounds and, optionally, second active ingredient can be administered to a patient prior to, during, or after the occurrence of the adverse effect associated with conventional therapy.

In one embodiment, an immunomodulatory compound can be administered in an amount of from about 0.1 to about 150 mg, or from about 1 to about 50 mg, or from about 2 to about 25 mg orally and daily, prior to, during, or after the use of conventional therapy.

Use with Transplantation Therapy

In one embodiment, is a method of treating or managing KS, which comprises administering the immunomodulatory compound, or a pharmaceutically acceptable salt, solvate, hydrate, stereoisomer, clathrate, or prodrug thereof, in conjunction with transplantation therapy.

As those of ordinary skill in the art are aware, the treatment of KS is often based on the stages and mechanism of the disease. For example, as inevitable leukemic transformation develops in certain stages of KS, transplantation of peripheral blood stem cells, hematopoietic stem cell preparation or bone marrow may be necessary. The combined use of the immunomodulatory compound and transplantation therapy provides a unique and unexpected synergism. In particular, an immunomodulatory compound exhibits immunomodulatory activity that may provide additive or synergistic effects when given concurrently with transplantation therapy in patients with KS.

In one embodiment, a method of treating or managing KS which comprises administering to a patient (e.g., a human) an immunomodulatory compound, or a pharmaceutically acceptable salt, solvate, hydrate, stereoisomer, clathrate, or prodrug thereof, before, during, or after the transplantation of umbilical cord blood, placental blood, peripheral blood stem cell, hematopoietic stem cell preparation or bone marrow. Examples of stem cells suitable for use in the methods provided herein are disclosed in U.S. Pat. No. 7,498,171 by R. Hariri et al., the entirety of which is incorporated herein by reference.

In one embodiment of this method, an immunomodulatory compound is administered before, during, or after the transplantation of autologous peripheral blood progenitor cell. In one embodiment, the immunomodulatory compound is pomalidomide, lenalidomide, or thalidomide. In one embodiment, the immunomodulatory compound is pomalidomide.

Cycling Therapy

In certain embodiments, the immunomodulatory compound provided herein is cyclically administered to a patient with KS. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one specific embodiment provided herein, an immunomodulatory compound is administered daily in a single or divided doses in a four to six week cycle with a rest period of about a week or two weeks. One embodiment further allows the frequency, number, and length of dosing cycles to be increased. Another specific embodiment provided herein encompasses the administration of an immunomodulatory compound provided herein for more cycles than are typical when it is administered alone. In yet another specific embodiment provided herein, an immunomodulatory compound provided herein is administered for a greater number of cycles that would typically cause dose-limiting toxicity in a patient to whom a second active ingredient is not also being administered.

In one embodiment, an immunomodulatory compound described herein is administered daily and continuously for three or four weeks at a dose of from about 0.1 to about 150 mg/day followed by a break of one or two weeks. In a particular embodiment, lenalidomide is administered in an amount of about 2.5, 5, 7.5, 10, 15, 20 or 25 mg/day, or in an amount of about 10 mg/day or 25 mg/day for three to four weeks, followed by one week or two weeks of rest in a four or six week cycle. In another particular embodiment, pomalidomide is administered in an amount of about 1, 2, 3, 4, 5, 6, 7, 8, 9, or 10 mg/day, or in an amount of about 1, 2, 3, 4, or 5 mg/day for three to four weeks, followed by one week or two weeks of rest in a four or six week cycle. In another particular embodiment, pomalidomide is administered in an amount of about 1, 2, 3, 4, 5, 6, 7, 8, 9, or 10 mg/day, or in an amount of about 1, 2, 3, 4, or 5 mg/day for two weeks, followed by one week of rest in a three week cycle.

In one embodiment provided herein, an immunomodulatory compound and a second active ingredient are administered orally, with administration of an immunomodulatory compound provided herein occurring 30 to 60 minutes prior to a second active ingredient, during a cycle of four to six weeks. In another embodiment provided herein, the combination of an immunomodulatory compound and a second active ingredient is administered by intravenous infusion over about 90 minutes every cycle. In a specific embodiment, one cycle comprises the administration of from about 2.5 to about 25 mg/day of lenalidomide and from about 10 to about 25 mg/m$^2$/day of a second active ingredient daily for three to four weeks and then one or two weeks of rest. In another specific embodiment, one cycle comprises the administration of from about 2.5 to about 25 mg/day of lenalidomide and from about 10 to about 25 mg/m$^2$/day of a second active ingredient daily for two to three weeks and then one or two weeks of rest. In another specific embodiment, one cycle comprises the administration of from about 2.5 to about 25 mg/day of lenalidomide for 14 consecutive days followed by seven consecutive days of rest in a 21 day cycle and from about 10 to about 25 mg/m$^2$/day of doxorubicin once on day 1 of the 21 day cycle. In a specific embodiment, one cycle comprises the administration of from about 1 to about 10 mg/day of pomalidomide and from about 10 to about 25 mg/m$^2$/day of a second active ingredient daily for three to four weeks and then one or two weeks of rest.

In another specific embodiment, one cycle comprises the administration of from about 1 to about 10 mg/day of pomalidomide and from about 10 to about 25 mg/m$^2$/day of a second active ingredient daily for two to three weeks and then one or two weeks of rest. In another specific embodiment, one cycle comprises the administration of from about 1 to about 10 mg/day of pomalidomide for 14 consecutive days followed by seven consecutive days of rest in a 21 day cycle and from about 10 to about 25 mg/m$^2$/day of doxorubicin once on day 1 of the 21 day cycle. Typically, the number of cycles during which the combinatorial treatment is administered to a patient will be from about one to about 24 cycles, more typically from about two to about 16 cycles, and even more typically from about four to about eight cycles.

Pharmaceutical Compositions and Dosage Forms

Pharmaceutical compositions can be used in the preparation of individual, single unit dosage forms. Pharmaceutical compositions and dosage forms provided herein comprise an immunomodulatory compound provided herein, or a pharmaceutically acceptable salt, solvate, hydrate, stereoisomer, clathrate, or prodrug thereof. Pharmaceutical compositions and dosage forms provided herein can further comprise one or more excipients.

Pharmaceutical compositions and dosage forms provided herein can also comprise one or more second active ingredients. Consequently, pharmaceutical compositions and dosage forms provided herein comprise the active ingredients disclosed herein (e.g., an immunomodulatory compound). Examples of optional second, or additional, active ingredients are disclosed herein (see, e.g., section 5.2).

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms provided herein will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, pharmaceutical compositions and dosage forms that contain little, if any, lactose mono- or di-saccharides. As used herein, the term "lactose-free" means that the amount of lactose present, if any, is insufficient to substantially increase the degradation rate of an active ingredient.

Lactose-free compositions provided herein can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

Further provided herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms provided herein comprise an immunomodulatory compound or a pharmaceutically acceptable salt, solvate, hydrate, stereoisomer, clathrate, or prodrug thereof in an amount of from about 0.10 to about 150 mg. Typical dosage forms comprise an immunomodulatory compound or a pharmaceutically acceptable salt, solvate, hydrate, stereoisomer, clathrate, or prodrug thereof in an amount of about 0.1, 1, 2, 2.5, 3, 4, 5, 7.5, 10, 12.5, 15, 17.5, 20, 25, 50, 100, 150 or 200 mg. In a specific embodiment, a preferred dosage form comprises 3-(4-amino-1-oxo-1,3-dihydro-isoindol-2-yl)-piperidine-2,6-dione (lenalidomide) in an amount of about 2.5, 5, 7.5, 10, 15, 20, 25 or 50 mg. In another specific embodiment, a preferred dosage form comprises 4-amino-2-(2,6-dioxopiperidin-3-yl)isoindoline-1,3-dione (pomalidomide) in an amount of about 1, 2, 3, 4 or 5 mg.

Oral Dosage Forms

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions provided herein is typically present in from about 50 to about 99 weight percent of the pharmaceutical composition or dosage form.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, or from about 1 to about 5 weight percent of disintegrant.

Disintegrants that can be used in pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A solid oral dosage form provided herein comprises an immunomodulatory compound described herein, anhydrous lactose, microcrystalline cellulose, polyvinylpyrrolidone, stearic acid, colloidal anhydrous silica, and gelatin. In a specific embodiment, the solid oral dosage form is a capsule comprising an immunomodulatory compound, lactose anhydrous, microcrystalline cellulose, croscarmellose sodium and magnesium stearate.

Kits

Kits and compositions for carrying out the methods provided herein are also contemplated. In certain embodiments, provided herein are kits useful for determining the efficacy of an immunomodulatory compound. In certain embodiments, provided herein are kits useful for assessing the efficacy of a compound in treating myelodysplastic syndromes. In some embodiments, provided herein are kits useful for determining the effect of an immunomodulatory compound. The kit comprises a solid support, and a means for detecting the gene, protein, or glycoprotein expression of at least one biomarker in a biological sample. Such a kit may employ, for example, a dipstick, a membrane, a chip, a disk, a test strip, a filter, a microsphere, a slide, a multiwell plate, or an optical fiber. The solid support of the kit can be, for example, a plastic, a silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an oral tissue, gastrointestinal tissue, an organ, an organelle, a biological fluid, a blood sample, a urine sample, or a skin sample.

In one embodiment a kit provided herein comprises an immunomodulatory compound provided herein, or a pharmaceutically acceptable salt, solvate or hydrate thereof. Kits may further comprise additional active agents, including but not limited to those disclosed herein.

It is noted that any combination of the above-listed embodiments, for example, with respect to one or more reagents, such as, without limitation, nucleic acid primers, solid support and the like, are also contemplated in relation to any of the various methods and/or kits provided herein.

EXAMPLES

Certain embodiments provided herein are illustrated by the following non-limiting example.

Pomalidomide for Kaposi Sarcoma in Patient with and without HIV

A clinical study was conducted to investigate the effects of pomalidomide in Kaposi sarcoma patient with and without HIV.

Enrollment: 22 patients (15 HIV positive and 7 HIV negative) median age 52 years (range 32-74) were studied. All patients with HIV were receiving antiretroviral therapy (ART) for median 48 months (7-227), HIV VL<50 copies/mL (all), and CD4 count 378 cells/µl (135-752). Patient characteristics are summarized in Table 1. Subjects received a median of 7 cycles of pomalidomide (range 2-12). All were evaluable for response.

TABLE 1

|  | Combined (n = 22) | HIV Positive (n = 15) | HIV Negative (n = 7) |
|---|---|---|---|
| Male Sex | 22 (100%)* | 15 (100%) | 7 (100%)* |
| Age | 52 (32-74) | 49 (32-65) | 61 (38-74) |
| Advanced ("T1") Disease | 17 (77%) | 10 (67%) | 7 (100%) |
| Prior Therapy | 19 (86%)** | 13 (87%) | 6 (86%) |

*Includes one genetically male transgendered individual
**Includes: cytotoxic chemotherapy 10; radiation therapy 5; other immunomodulatory drugs 2; interferon 1; local therapies 7

Methods: Patients received pomalidomide 5 mg per day orally for 21 days of 28 day cycles. Aspirin at 81 mg daily was administered as thromboprophylaxis. Assessments were performed every 4 weeks for lymphocyte numbers, Kaposi sarcoma associated herpesvirus (KSHV/HHV8) viral load (VL) and HIV VL and at 8 weeks for T cell subsets and activation by immunophenotyping of peripheral blood mononuclear cells (PBMC). KSHV VL in PBMC and HIV VL in plasma were assayed by quantitative PCR; an ultrasensitive single copy assay was used for HIV VL. Changes from baseline were evaluated using the Wilcoxon signed rank test with P<0.005 considered significant given multiple comparisons. Differences in changes between the HIV infected and uninfected groups were evaluated using the Wilcoxon rank sum test. Median time of the patients on therapy 7 cycles (range 2-12).

Safety and Tolerability: No dose limiting events was observed at 5 mg per day administration for 21 days of 28 day cycles. Adverse events were generally mild, self limited, or reversible following therapy. No unplanned hospitalizations, no febrile neutropenia, and no thromboembolic events were observed. One subject ceased therapy for adverse effect (exacerbation of pre-existing anxiety).

Subsequent cycles commenced on day 29. In certain cases cycles were commenced when ANC was ≥1000 cells/mm3, hemoglobin≥10 g/dL, platelets≥50,000 cells/mm3 and otherwise held until these thresholds were met. Pomalidomide was held for ANC<500 cells/mm3, platelets<25,000 mm3, or severe infection. HIV-infected patients continued baseline ART without adjustment. Prophylaxis for opportunistic infections including *Pneumocystis jiroveci* was administered following current guidelines. Pomalidomide was continued for a maximum of 12 months, and stopped earlier for complete response, unacceptable adverse events, non-adherence, or patient preference.

Kaposi sarcoma responses: KS responses were evaluated every cycle and categorized as complete (CR), partial (PR), stable disease (SD), or progressive disease (PD) using modified ACTG criteria. To be evaluable for response, patients completed at least two cycles of therapy. Evaluations included lesion counts, measurement of the sum product of the diameters of five indicator lesions, assessment of nodularity, and measurement of limb circumference if tumor-associated edema was present. PR was considered as at least 50% decrease in number of lesions and/or sum product of the diameters of marker lesions and/or nodularity of lesions, and no new lesions in previously uninvolved areas nor criteria for PD. CR was considered as clinical resolution of all lesions and tumor-associated phenomenon, with biopsy confirmation. Both CR and PR had to be sustained for 4 weeks. Best response was evaluated for each patient.

Figure 1B:
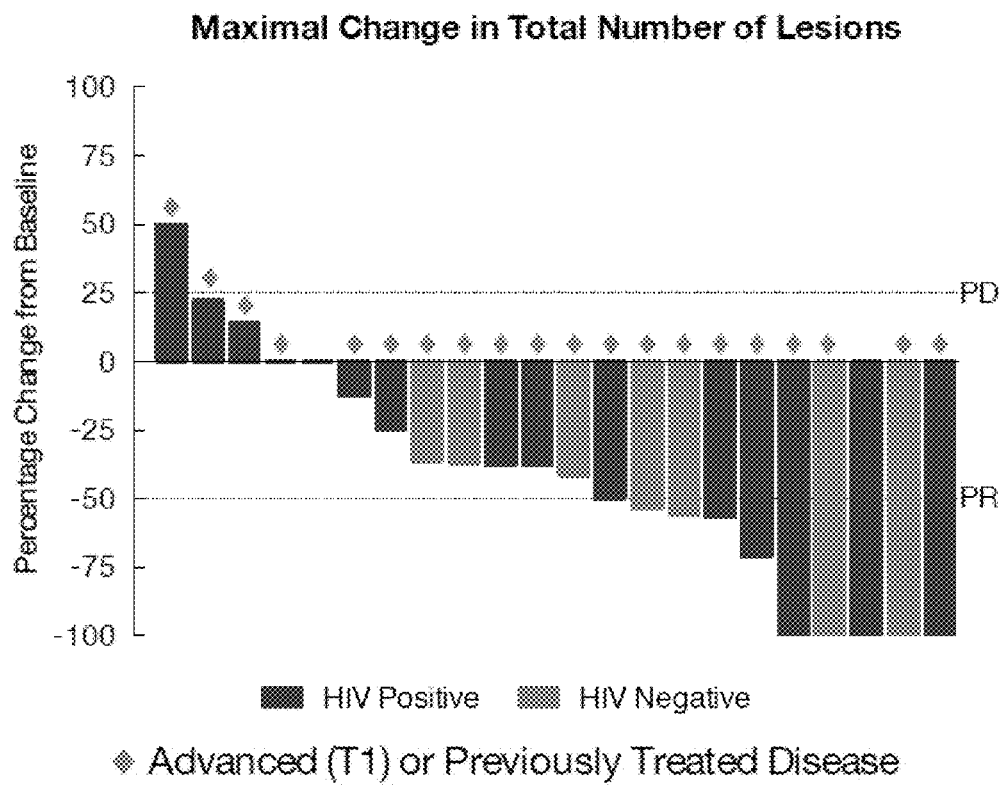
FIG. 1B shows individual responses (maximal change in total number of lesions) from Kaposi's sarcoma patients after treatment with pomalidomide.

Complete and partial responses are objective tumor responses by modified AIDS Clinical Trial Group Criteria for KS. Complete response also requires pathological confirmation. The results are summarized in Table 2. Individual responses are shown in FIG. 1A (maximal change in number of nodular lesions) and FIG. 1B (maximal change in total number of lesions). No decrease in quality of life during therapy was reported by patient. Improved satisfaction with appearance was reported by patients. The results show that responses were generally rapid, were linked to improved self reported outcomes, and occurred even in advanced and heavily pretreated KS. This includes objective responses in patients previously refractory to standard cytotoxic therapy and in patients who have previously received other immunomodulatory drugs (e.g., thalidomide, lenalidomide, or both).

Patients receiving pomalidomide also showed a decrease in tumor-associated edema: 10 of 17 subjects with edema (59%) had evidence of improvement. In 8, measurements of limb circumference showed at least a 2 cm reduction with therapy. Two additional subjects reported substantial subjective improvement: one had decreased pedal pain and one was able to resume wearing closed shoes.

At baseline HRQL by FAHI was comparable with recent reports in men with HIV, while subjects commonly reported KS-related edema (63.6%), dissatisfaction with appearance (54.6%) and KS-related pain interfering with work or activities (40.9%). HRQL by FAHI did not decrease during therapy, and was stable following completion (all p>0.05). There was a trend to improved satisfaction with appearance at the three month questionnaire (during therapy) (p=0.07) and a significant increase at the end-therapy questionnaire (p=0.03), with the number of subjects reporting little to no satisfaction decreasing from 12 (54.6%) to 5 (26.3%). Other parameters did not change significantly.

TABLE 2

|  | Enrolled (Assessable) | Overall Response (CR + PR) | Complete Response (CR) | Partial Response (PR) | Stable Disease (SD) | Progressive Disease (PD) | Time to Response |
| --- | --- | --- | --- | --- | --- | --- | --- |
| Combined | 22 (22) | 16 (73%) | 4 (18%) | 12 (55%) | 3 (14%) | 3 (14%) | 4 weeks (4-36) |
| HIV positive | 15 (15) | 9 (60%) | 3 (20%) | 6 (40%) | 3 (20%) | 3 (20%)* | 8 weeks (4-32) |
| HIV negative | 7 (7) | 7 (100%) | 1 (14%) | 6 (86%) | 0 | 0 | 4 weeks (4-36) |

*Includes one subject who became non-adherent to ART and protocol therapy

Pharmacokinetic Studies: Plasma concentrations of pomalidomide were assayed using high-performance liquid chromatography with fluorescence detection with a lower limit of quantitation (LLOQ) of 1 ng/mL. A non-compartmental analysis was used to calculate plasma pharmacokinetic parameters (Pharsight Corp, Mountain View, Calif.). The maximum plasma concentration ($C_{MAX}$) and time to $C_{MAX}$ ($T_{MAX}$) were recorded as observed values; the area under the plasma concentration vs time curve (AUC) was calculated using the log-linear trapezoidal method. For day 1 of cycle 1 ($C_1D_1$), the AUC extrapolated to infinity ($AUC_{INF}$) was used, unless the percent extrapolated exceeded 25%, in which case $AUC_{LAST}$ (to the last quantifiable time point) was used. The steady-state exposure on $C_1D_{15}$ was calculated using $AUC_{LAST}$.

Pharmacokinetic Studies were performed pre-dose on cycle 1 day 1 and day 15. Across all analyzed doses:

$T_{MAX}$=2.71±1.73 hrs, $T_{1/2}$=7.10±2.48 hours, and $C_{MAX}$=61.21±29.30 ng/mL. No evidence of accumulation was observed from day 1 to day 15. No significant differences in pharmacokinetics by HIV status was observed. No significant differences in pharmacokinetics by ART regimen was observed. Comparing HIV infected with non-infected subjects, for $C_{MAX}$ at $C_1D_1$ p=0.45, at $C_1D1_5$ p=0.80 at $C_1D_{15}$ and comparing changes from baseline p=0.91; for $AUC_{LAST}$ at $C_1D_1$, p=0.63; at $C_1D_{15}$ p=0.97 and comparing changes from baseline p=0.91.

Laboratory Assays: Lymphocyte subsets were assessed by fluorescent-activated cell sorting using the BlueOcean platform (Beckman Coulter, Carlsbad, Calif.). Plasma HIV-1 mRNA was evaluated using an ultrasensitive assay whose sensitivity was 1 viral copy per plasma volume. Briefly, a triplex PCR was used using a modification of a previously reported assay with three primers: one spanning the start codon of gag, one in the gag coding region, and one internal control. Samples were tested from 6 mL plasma aliquots, with 12 replicants per sample. KSHV VL in peripheral blood mononuclear cells (PBMC) was assessed by quantitative real-time PCR.

Statistical Considerations: This study determined the safety, tolerability and pharmacokinetics of pomalidomide in subjects with KS. For the phase II component, the overall response rate (ORR, comprising CRs and PRs) was determined for patients treated with pomalidomide at 5 mg 21/28 days. HIV infected and uninfected cohorts were evaluated separately and combined. The unacceptable ORR for further development was defined as 10% and a desirable (targeted) ORR as 40%. Up to 10 HIV negative patients were to be enrolled, with the goal of obtaining responses in those 10 patients; that would have 83.3% probability of occurring if the true ORR were 40% and 7.0% probability of occurring if the true ORR were 10%. Up to 15 HIV positive patients were to be enrolled, with the goal of obtaining responses in those 15 patients; that would have 90.9% probability of occurring if the true ORR were 40% and 5.6% probability of occurring if the true ORR were 10%. Progression free survival (PFS), defined as time from day 1 of pomalidomide therapy until progression requiring a change in therapy, was estimated using the Kaplan-Meier method.

Changes in immunologic and virologic parameters were evaluated by a Wilcoxon signed rank test. Exact Wilcoxon rank sum tests were used to compare pharmacokinetic parameters at each time point and differences from baseline. All p-values are two-tailed and reported without adjustment for multiple comparisons. HRQL was analyzed using a using a mixed model repeated measures analysis for FAHI and the marginal homogeneity test for KS-specific questions Immunologic Correlatives: Significant increases in CD4 and CD8 counts were observed at week 4 and week 8 of therapy, with a decline in CD19 B-cells and no change in NK cells or HIV VL. A transient increase in KSHV VL was seen at week 4, but was not sustained at week 8. The immunologic results are summarized in Table 3.

TABLE 3

| Parameter | Baseline | Change to Week 4 (Med, range) | P Value | Change to Week 8 (Med, range) | P Value | Change to End Therapy (Med, range) | P Value |
|---|---|---|---|---|---|---|---|
| CD3 (cells/µL) | 1184 (525-3325) | +275 (−506-1524) | 0.0044 | +190 (−972-1455) | 0.0083 | +11 (−1368-903) | 0.93 |
| CD4 (cells/µL) | 440 (135-1171) | +108 (−147-650) | 0.0006 | +40 (−279-491) | 0.0099 | −46 (−496-260) | 0.35 |
| CD8 (cells/µL) | 500 (259-2385) | +101 (−444-915) | 0.017 | +142 (−710-834) | 0.015 | 104 (−882-418) | 0.50 |
| NK (cells/µL) | 178 (28-557) | +23 (−130-117) | 0.71 | −6 (−174-127) | 0.72 | 10 (−279-94) | 0.53 |
| CD19 (cells/µL) | 141 (0-322) | −35 (−117-76) | 0.0031 | −70 (−169-62) | <0.0001 | −87 (−271-79) | <0.0001 |
| KSHV VL (copies/PBMC)* | 0 (0-8750) | 0† (−238-5250) | 0.05 | 0 (−238-20850) | 0.56 | 0 (−238-160674) | 0.63 |
| Plasma HIV VL (copies/mL)** | 1.5 (<0.5-58) | +0.3 (−1.5-27) | 0.41 | +0.75 (−35-40) | 0.16 | −0.5 (−38-218.5) | 0.25 |

*Comparisons made with log10 transformed KSHV VL and HIV VL
**Restricted to the 15 HIV positive subjects; paired data available for 10-13 patients
†10 subjects (45%) showed an increase in KSHV VL in PBMCs at week 4 including 8 (35%) who became detectable from undetectable In addition, at week 8 both CD4 and CD8 T-cells showed significant increases in activation (CD38+, HLADR+ and DR+/38+) and decreases in senescence (CD57+). Both also showed a significant shift towards increased central memory (CM) and away from naive (N) and effector (E) phenotypes, with no change in effector memory (EM) cells. There was no significant change in NK cells, and a reversible decrease in CD19+B cells. There was no significant change in plasma HIV VL by ultrasensitive single copy assay. There was a significant increase in KSHV VL at week 4 (p=0.05): 10 subjects (45%) showed an increase in KSHV VL including 8 (35%) who became detectable from undetectable. This resolved at subsequent time points. There were no significant changes in Ki67 or PD-1 expression in either CD4 or CD8 cells. There was no significant difference between HIV infected and uninfected patient groups in the observed effects on any parameter including cell number and phenotype. The results are summarized in Table 4.

TABLE 4

| CD4 Subsets | Baseline (%) (med, range) | Absolute Change in % at Week 8 (med, range) | P Value |
|---|---|---|---|
| RO− 27+ (N) | 32.6 (13.3-76.5) | −6.6 (−35.8-21.6) | 0.002 |
| RO+ 27+ (CM) | 41.9 (13.6-63.6) | +6.4 (−15.5-32.5) | 0.027 |
| RO+ 27− (EM) | 16.7 (4.6-31.7) | +1.7 (−7.2-21.0) | 0.28 |
| RO− 27− (E) | 3.3 (0.4-14.3) | −1.5 (−5.7-0.3) | 0.0004 |
| 38+ | 34.5 (11.2-67.3) | +4.3 (−13.0-19.4) | 0.024 |
| HLA DR+ | 8.9 (3.3-25.0) | +8.3 (0.7-19.5) | <0.0001 |
| 38+ DR+ | 2.5 (0.6-11.7) | +2 (−1.0-8.1) | <0.0001 |
| 57+ | 6.3 (0.6-26.6) | −1.34 (−16.2-7.6) | 0.034 |

TABLE 4-continued

| CD8 Subsets | Baseline (%) (med, range) | Absolute Change in % at Week 8 (med, range) | P Value |
|---|---|---|---|
| RO− 27+ (N) | 21.0 (9.7-70.4) | −5.1 (−13.7-14.3) | 0.019 |
| RO+ 27+ (CM) | 17.1 (2.5-37.9) | +8.1 (−8.4-18.6) | 0.0047 |
| RO+ 27− (EM) | 18.4 (4.6-40.8) | +1.0 (−9.4-44.9) | 0.35 |
| RO− 27− (E) | 31.8 (4.1-63.7) | −6.1 (−47.3-22.5) | 0.01 |
| 38+ | 33.4 (8.3-66.0) | +19.9 (−0.8-40.6) | <0.0001 |
| HLA DR+ | 19.6 (5.0-46.4) | +11.6 (−4.7-32.1) | 0.0001 |
| 38+ DR+ | 8.0 (0.4-33.3) | +8.5 (0.1-22.6) | <0.0001 |
| 57+ | 30.8 (2.9-72.9) | −11.0 (−28.5-6.1) | <0.0001 |

Pomalidomide induced significant increases in the number of CD4 and CD8 T-cells and the proportion of activated and central memory cells and decreased senescence in both HIV infected and uninfected subjects. In addition, administration of pomalidomide induced a shift towards central memory T cells (RO+27+) and away from naïve T cells (RO−27+). The transient early rise in KSHV VL may reflect reactivation of latent infection and enhance immune killing of KSHV infected cells. This supports a role for T-cell modulation as one potential mechanism of the observed activity. The results of this study suggests potential use of immunomodulatory drugs to augment immune responsiveness in patients having HIV and other immunodeficiencies.

Adverse effects: Pomalidomide was well tolerated, and AEs in both cohorts were consistent with previous studies. Common adverse events were neutropenia, constipation, anemia not requiring transfusion, fatigue, and rash. These were generally mild and self-limited, or resolved following cessation of therapy. There were no unplanned hospitalizations, no episodes of febrile neutropenia, and no thromboembolic events.

This study demonstrates that the immune modulatory agent pomalidomide at a dose of 5 mg for 21 of 28 days appears tolerable and active in subjects with symptomatic KS regardless of HIV status. The overall response rate was 73%, and it is particularly striking that all HIV-uninfected subjects responded.

KS response rates are affected by patient immune status and disease bulk, and can be confounded by ART initiation. The response estimate in this study is strengthened by the predominance of subjects with advanced and previously treated disease. Importantly too, any therapeutic effect of ART was controlled for in two respects: first by including HIV-uninfected subjects where no such effect could be seen, and secondly by excluding HIV-infected subjects who had recently commenced ART. Indeed, the median time on ART among HIV-infected subjects was 4 years, greatly exceeding common time estimates of maximal KS response to ART.

Pomalidomide with aspirin thromboprophylaxis was well-tolerated, with minimal AEs and no impairment of self-reported HRQL during therapy. This study also represents the first guidance for use of pomalidomide in HIV-infected patients, an important consideration given its activity in hematologic malignancies that may develop in this population. Pharmacokinetic studies showed no differences in pomalidomide absorption or elimination in HIV-infected subjects, and no evidence of accumulation even among subjects receiving tenofovir. There were no excess or idiosyncratic AEs in HIV-infected subjects. This supports the use of pomalidomide at standard doses in people with HIV.

This study provides formative evidence that pomalidomide can address key unmet clinical needs for people KS. In resource-rich regions, pomalidomide may be of particular utility in HIV-uninfected patients, in patients who have received substantial cumulative doses of anthracyclines and in patients with less extensive but symptomatic disease for whom avoidance of cytotoxic chemotherapy would be beneficial. In resource-limited regions, there is an urgent need for effective and tolerable oral agents; with appropriate safeguards and monitoring, pomalidomide could address this.

Pomalidomide in Combination with Doxorubicin in Patients with Advanced Kaposi's Sarcoma Provided herein is a clinical trial protocol to investigate the effects of pomalidomide in combination with doxorubicin in patients with advanced Kaposi's sarcoma.

Enrollment eligibility criteria: Patients with biopsy proven (confirmed in the laboratory of pathology, CCR) Kaposi's sarcoma (KS). Patients can meet eligibility criteria of either Group I or Group II as following:

Group I: KS that requires systemic therapy (no prior therapy required). This includes (i) T1 KS or KS affecting quality of life due to local symptoms or psychological distress, (ii) KS patients with an inadequate response to pomalidomide (either progressive disease or stable disease after 4 months), and (iii) KS patients with an inadequate response to liposomal doxorubicin (either progressive disease or stable disease after 6 cycles). Group I excludes patients eligible for Group II. A wash out period off treatment of 3 weeks is required, except in the case of patients with progressive disease.

Group II: KS in one of the following high-risk groups (no prior therapy required): (i) concurrent KSHV-associated multicentric Castleman's disease (MCD), or (ii) KSHV Inflammatory Cytokine Syndrome (KICS), including those also meeting clinical criteria for KS immune reconstitution syndrome (KS IRIS).

Patients can be HIV positive or negative. All HIV positive patients must be willing to be compliant with highly active antiretroviral therapy (HAART). HIV positive patients of Groups I are on HAART for 1 month with stable disease and there is no minimum time restriction with progressive disease. For HIV positive patient of Group II, there is no minimum time restriction on prior HAART and patients may be HAART naive.

Study Design: Patients receive pomalidomide once a day consecutively on days 1-14 of a 21-day cycle, at the dose levels described below in Table 5, combined with liposomal doxorubicin on day 1 of the 21-day cycle, at the dose levels described below in Table 5. Pegfilgrastim is given 24 h after the end of liposomal doxorubicin.

Dose escalation design: The study starts by enrolling 3 patients into each of two groups of patients (Group I and Group II), each receives the drug combination starting on dose level 1.

If 1 dose limiting toxicity (DLT) in the first 3 patients is noted in either cohort, that cohort is expanded to 3 additional patients at that dose level. If 0/3 or 1/6 DLT occur in a Group at a particular dose, the dosing in that Group increases to the next dose level. Dose escalation for each cohort stops when 2 or more DLTs occur (in a cohort of 3 or 6 patients). If dose escalation proceeds to DL3, 6 patients are treated at this dose (unless 2 DLT occur before that time). If 2 or more DLTs occur at dose level 1 in either cohort, that cohort dose de-escalates to DL-1.

The MTD is the highest dose of the combination where fewer than 2 of 6 subjects experience a DLT. The MTD is determined for Group I and Group II independently, as it may differ. If 2 or more DLTs out of six patients are noted at DL-1, additional dose reductions are considered.

TABLE 5

| Dose level | Pomalidomide (mg) | Liposomal doxorubicin (mg/m²) |
|---|---|---|
| −1 | 2 | 15 |
| 1 | 2 | 20 |
| 2 | 3 | 20 |
| 3 | 5 | 20 |

Dose limiting toxicity includes any Grade 4 Toxicity (CTACE v4.0) that is at least possibly attributable to pomalidomide or liposomal doxorubicin and unlikely attributable to HIV, its therapy or manifestations of KSHV-associated malignancy, and any Grade 3 adverse event (CTCAE v4.0) possibly, probably, definitely attributed to pomalidomide or liposomal doxorubicin, excluding certain specific adverse effects.

Immunomodulatory Drugs Inhibit Primary Effusion Lymphoma Cell Proliferation

A study was conducted to investigate the potential use of immunomodulatory drugs in inhibiting primary effusion lymphoma (PEL) cell proliferation and their effects on immune modulation.

Methods: BCBL-1, BC-3, and JSC-1 PEL cell lines as well as an uninfected Burkett's lymphoma line (CA-46) were treated with three immunomodulatory drugs (thalidomide, lenalidomide, and pomalidomide), and the effects on cell viability, NF-κB and IRF4 levels were investigated. In addition, the effect of the immunomodulatory drugs on KSHV down-regulation of MHC-1 during lytic activation was investigated by FACS analysis after pretreating the cells with Immunomodulatory drugs prior to lytic activation with butyrate.

Cell Viability: Cells were plated in triplicate at a density of 30,000-60,000 cells per well in 96-well plates. Cell lines were kept separate on different plates. Cell viability after indicated treatments were assayed by Trypan Blue or by adding the CellTiter-Glo reagent to measure the total ATP in cells cultured with serum-supplemented medium. For the latter, the corresponding luminescence values, correlated to the number of cells, were measured using a luminometer. The values for percentage of living cells were normalized to the control.

Cell Culture: The PEL lines JSC-1 (John Hopkins University, Baltimore, Md.), dually infected with Epstein-Barr virus (EBV) and HHV-8, and BC-3 (ATCC, Rockville, Md.) and BCBL-1(National Institute of Health AIDS Research and Reagent Program, Rockville, Md.), harboring KSHV only, and CA-46, an uninfected cancerous B-cell line, were grown in RPMI 1640 medium (Invitrogen, Carlsbad, Calif.) supplemented with 15% fetal-bovine serum (FBS) (Thermo Scientific, Rockford, Ill.) and Pen/Strep glutamine at 37° C. with 5% $CO_2$.

Western Blotting: At the end of an incubation period, cells were lysed and nuclear/cytoplasmic extracts were prepared using the NE-PER nuclear extraction kit (Pierce). Samples were subjected to SDS-PAGE (4 to 12% NuPAGE Tris-Bis) (Invitrogen) and transferred to nitrocellulose. The membrane was blocked with 5% w/v nonfat dry milk in 1×TBST (10 mM Tris-Hcl, pH 80, 150 mM NaCl, and 0.05% Tween 20) overnight at 4° C. Blots were incubated with indicated antibodies such as anti-IRF-7 (Santa Cruz), anti-IRF-4 (Cell Signaling), anti-p21 (Cell Signaling), anti-NF-κB p65 (Cell Signaling), anti-NF-κB phospho-p65 (Cell Signaling), IFN-γRa (Cell Signaling), or anti-CRBN (Sigma-Aldrich), and subjected to the appropriate secondary antibody conjugated to alkaline phosphatase (Promega). Bands were visualized with Western Blue stabilized substrate (Promega). Membranes were scanned and images were processed as described.

Flow Cytometry Analysis and Antibodies: For flow cytometry analysis of MHC-I expression, cells were plated at 400,000 cells/mL and pretreated with immunomodulatory agents as indicated. After twenty-four hours, cells were treated with butyrate at indicated amounts to induce lytic activation and down-regulation of MHC-I. After another twenty-four hours, cells were analyzed on FACS and extracts were prepared as indicated. For flow cytometry analysis, the cells, 1×105 per sample, were incubated with indicated conjugated monoclonal antibodies for 30 min at 4° C. After washing twice with PBS, cells were resuspended in PBS and flow cytometry analysis was performed with a FACSCalibur. FITC-conjugated antibodies to anti-HLA MHC Class I (Sigma-Aldrich) and PE-conjugated antibodies to anti-DR MHC Class II (BioLegend) were used for flow cytometry.

Results:

Drug concentrations tested were based on multiples of the plasma serum Cmax concentrations determined in patients at the approved doses listed below.

| Drug | Dose | Cmax | Plasma Serum Concentration |
|---|---|---|---|
| Thalidomide | 200 mg | 1.76 μg/mL | 7 μM |
| Lenalidomide | 25 mg | 451 ng/mL | 2 μM |
| Pomalidomide | 4 mg | 75 ng/mL | 0.3 μM |

Figure 2A:
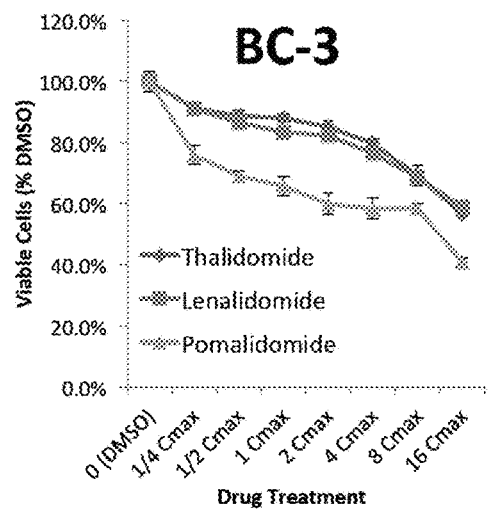
FIG. 2A shows the effects of thalidomide, lenalidomide, and pomalidomide on the cell viability in BC-3 cell line.
Figure 2B:
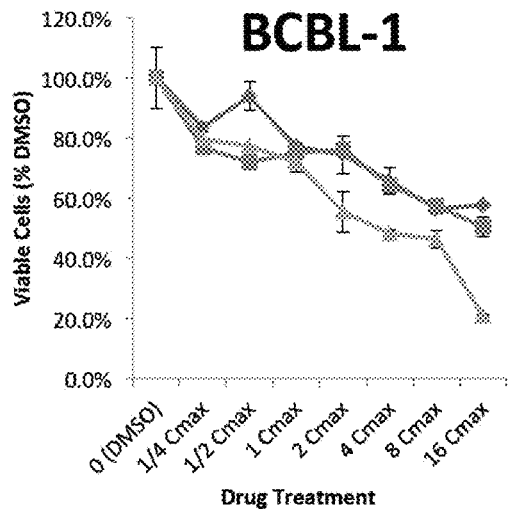
FIG. 2B shows the effects of thalidomide, lenalidomide, and pomalidomide on the cell viability in BCBL-1 cell line.
Figure 2C:
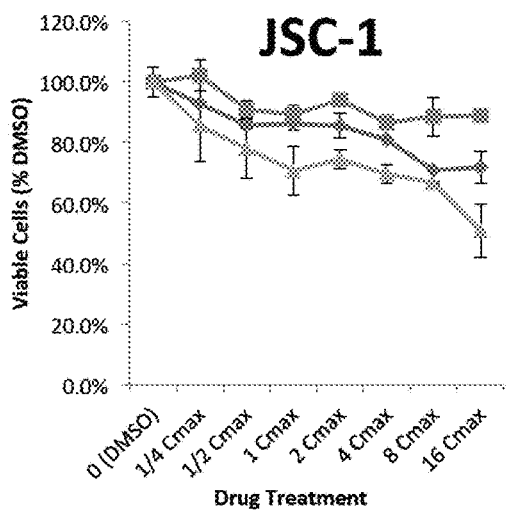
FIG. 2C shows the effects of thalidomide, lenalidomide, and pomalidomide on the cell viability in JSC-1 cell line.
Figure 2D:
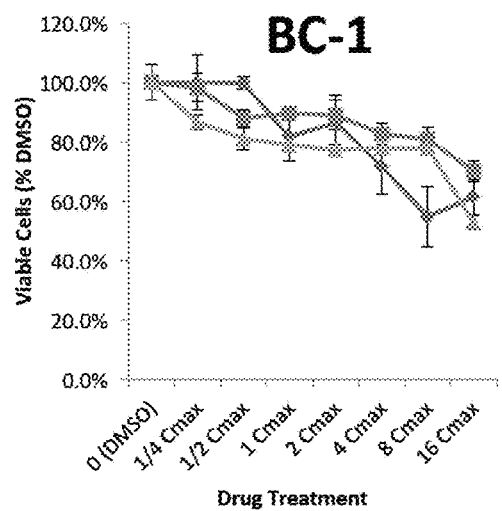
FIG. 2D shows the effects of thalidomide, lenalidomide, and pomalidomide on the cell viability in BC-1 cell line.
Figure 2E:
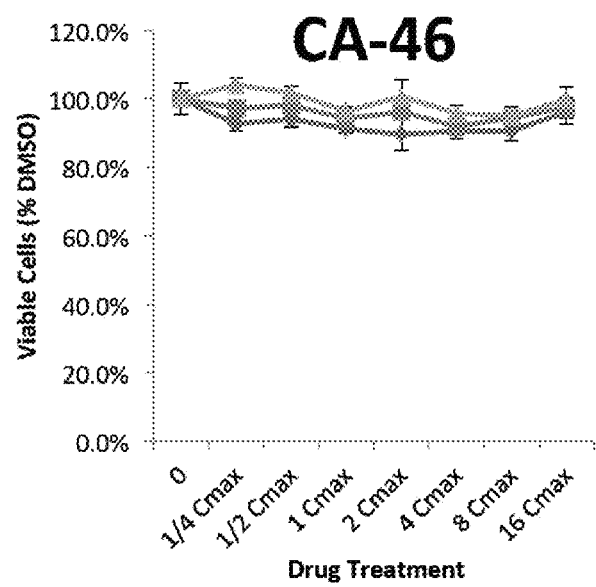
FIG. 2E shows the effects of thalidomide, lenalidomide, and pomalidomide on the cell viability in CA-46 cell line.

The effects of the immunomodulatory drugs on the cell viability in different cell lines are depicted in FIG. 2A (BC-3), FIG. 2B (BCBL-1), FIG. 2C (JSC-1), FIG. 2D (BC-1), and FIG. 2E (CA-46). The results show that CA-46, a KSHV negative B-cell line, was insensitive to the immunomodulatory drugs compared to KSHV-infected PEL lines, suggesting the immunomodulatory drugs specifically inhibit PEL proliferation. Among the three tested compounds, pomalidomide was the most effective one at killing KSHV infected cells.

Figures 3A, 3B, 3C:
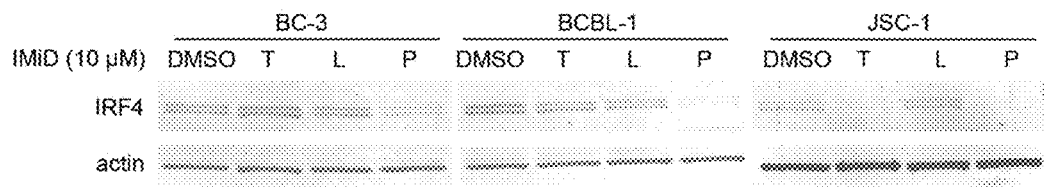
FIG. 3A shows the effect of thalidomide, lenalidomide, and pomalidomide on the regulation of IRF4 and NF-kB in BC-3 cell line.
FIG. 3B shows the effect of thalidomide, lenalidomide, and pomalidomide on the regulation of IRF4 and NF-kB in BCBL-1 cell line.
FIG. 3C shows the effect of thalidomide, lenalidomide, and pomalidomide on the regulation of IRF4 and NF-kB in JSC-1 cell line.
Figures 4A, 4B, 4C:
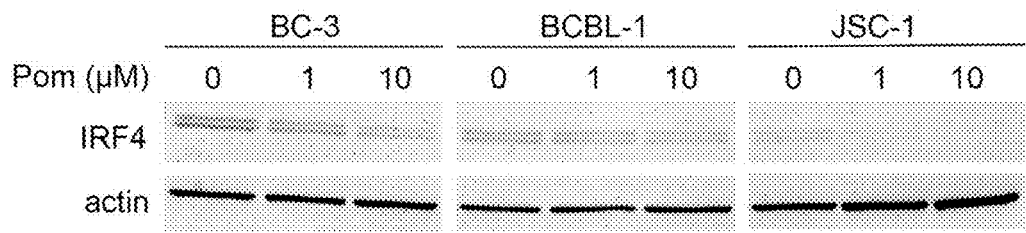
FIG. 4A shows the effect of pomalidomide at 1 µM and 10 µM on the regulation of IRF4 in BC-3 cell line.
FIG. 4B shows the effect of pomalidomide at 1 µM and 10 µM on the regulation of IRF4 in BCBL-1 cell line.
FIG. 4C shows the effect of pomalidomide at 1 µM and 10 µM on the regulation of IRF4 in JSC-1 cell line.
Figure 4D:
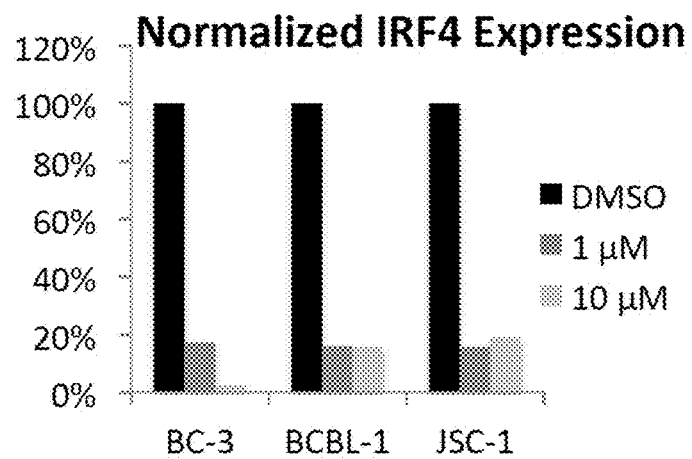
FIG. 4D shows the normalized expression of IRF4 in BC-3, BCBL-1, and JSC-1 cell lines after exposure to pomalidomide.
Figure 5:
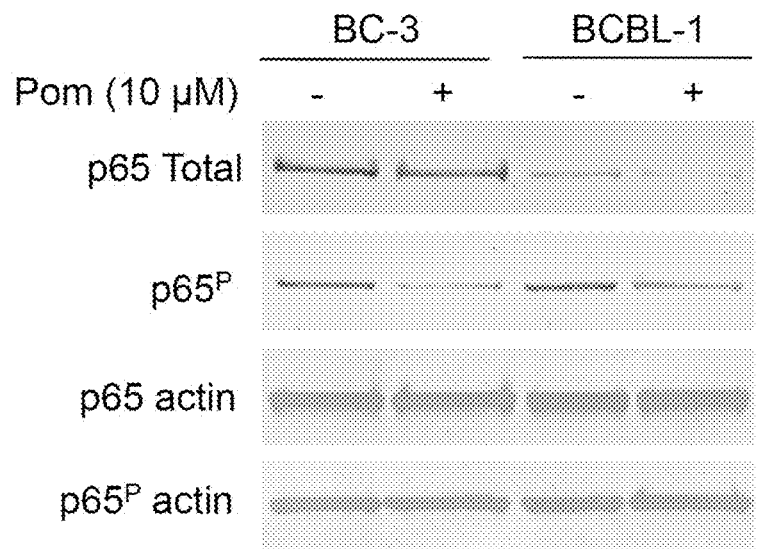
FIG. 5 shows the effect of pomalidomide at 10 µM on the regulation of NF-kB in the BC-3 and BCBL-1 cell lines.

Treatment of cells with immunomodulatory drugs led to a down-regulation of IRF4 and NF-κB: In Primary Effusion Lymphoma, the KSHV vFLIP protein upregulates IRF4 and NF-κB and promotes cellular proliferation. FIGS. 3A-3C. Cells were treated with thalidomide, lenalidomide, and pomalidomide at indicated concentrations for 72 hours and expression levels were measured. Among the three tested compounds, pomalidomide was most effective in downregulating IRF4 in all three KSHV cell lines (BC-3, BCBL-1, and JSC-1). FIGS. 4A-4D. Pomalidomide at 1 μM and 10 μM downregulated IRF4 in all three PEL lines (BC-3, BCBL-1, and JSC-1). Cells were treated with pomalidomide at 10 μM concentrations for 72 hours and cell lysates were prepared and expression levels were assessed by western blot. FIG. 5. Among all three tested compounds, pomalidomide was most effective at inhibiting NF-κB activity (measured by the ratio of $p65^P$:total p65).

Figure 6A:
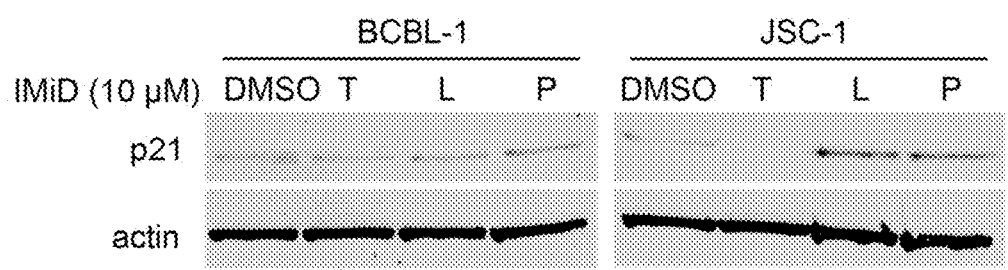
FIG. 6A shows the effect of thalidomide, lenalidomide, and pomalidomide on regulation of p21 in BCBL-1 and JSC-1 cell lines.
Figure 6B:
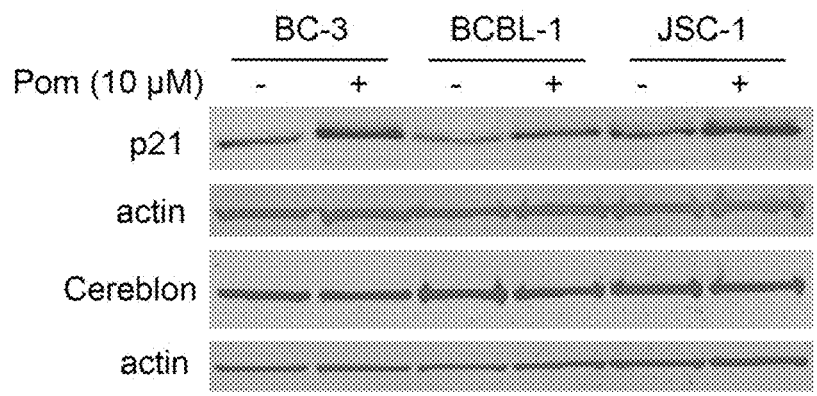
FIG. 6B shows the effect of 10 µM pomalidomide on the regulation of p21 and cereblon in BC-3, BCBL-1, and JSC-1 cells.
Figure 7A:
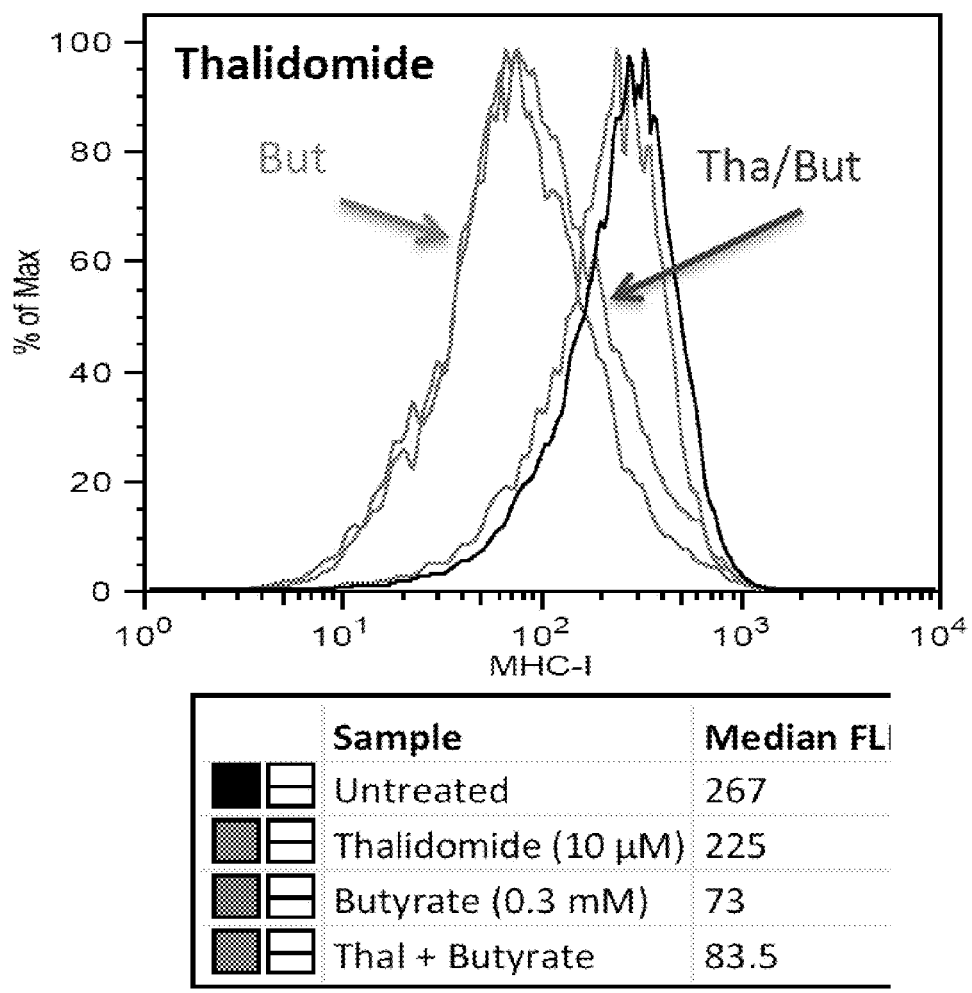
FIG. 7A shows the effect of thalidomide on inhibition of butyrate induced MHC-1 down-regulation in BCBL-1 cells.
Figure 7B:
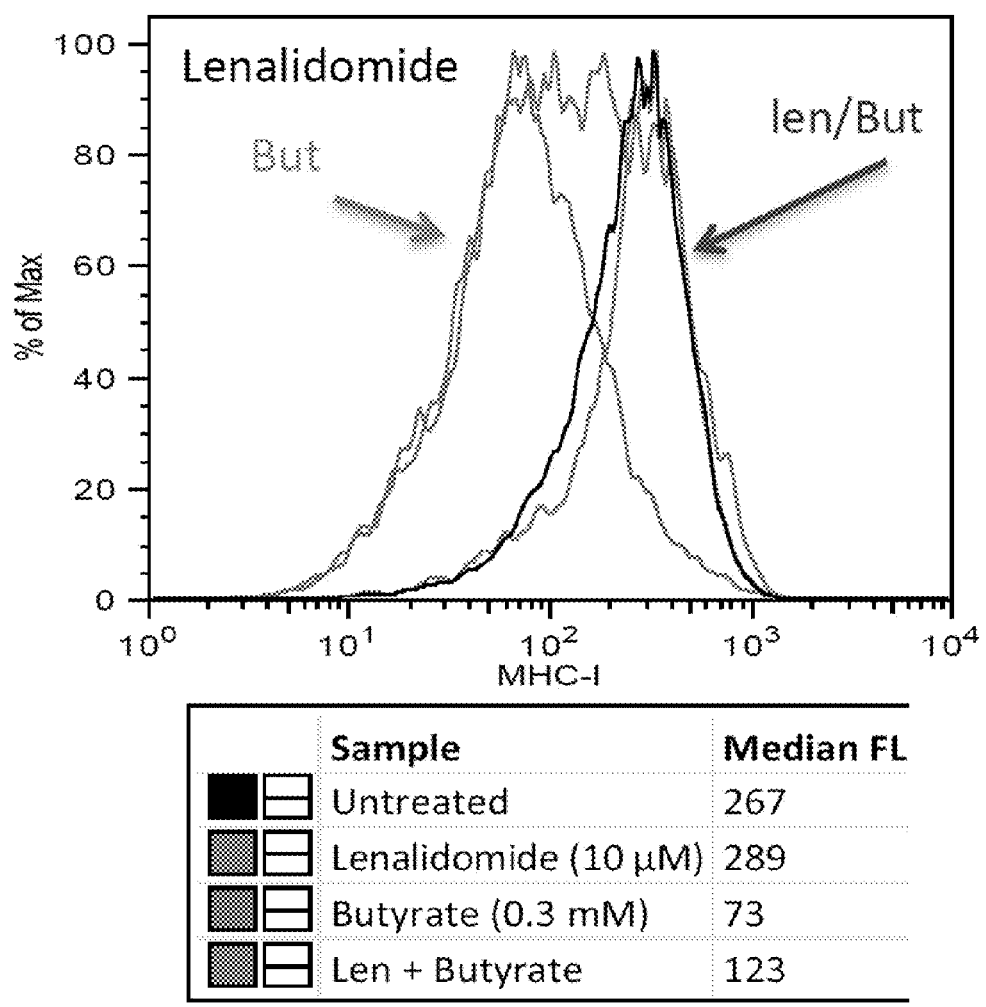
FIG. 7B shows the effect of lenalidomide on inhibition of butyrate induced MHC-1 down-regulation in BCBL-1 cells
Figure 7C:
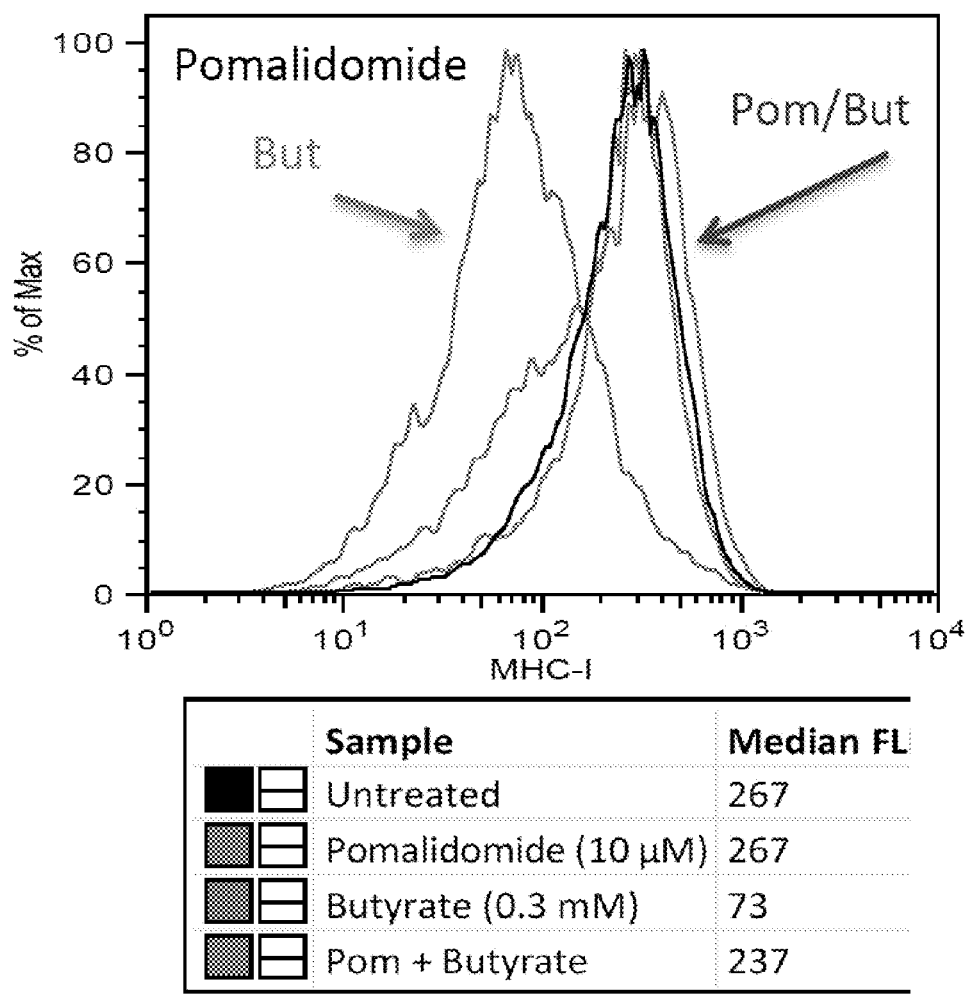
FIG. 7C shows the effect of pomalidomide on inhibition of butyrate induced MHC-1 down-regulation in BCBL-1 cells
Figure 8:
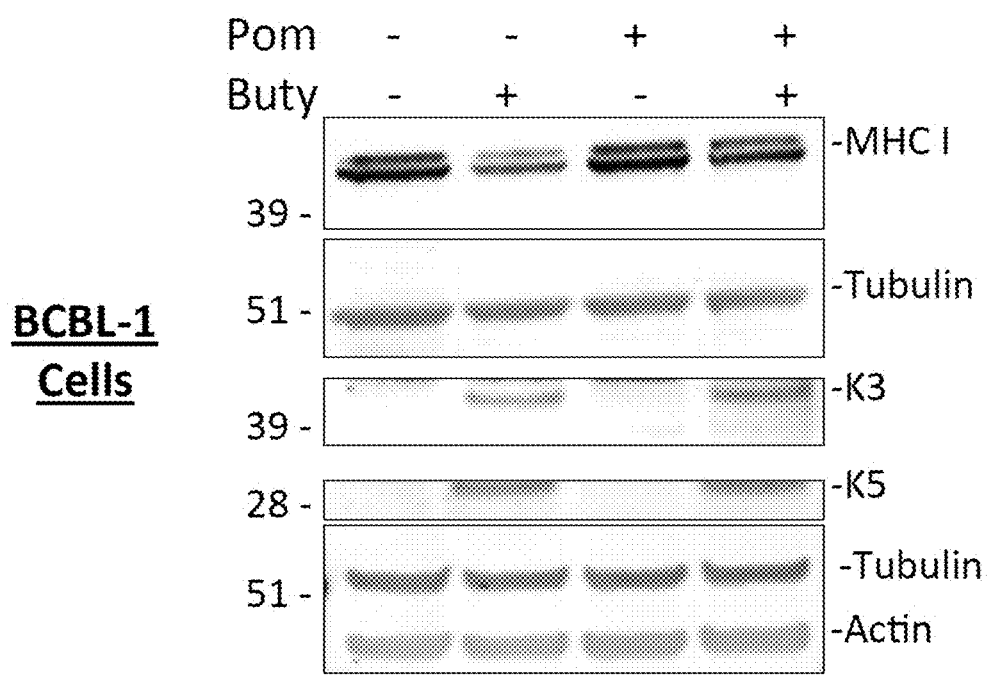
FIG. 8 shows a Western blot of BCBL-1 cells treating with pomalidomide where pomalidomide inhibits MHC-1 down-regulation but appears not to prevent K3 and K5 expression.
Figure 9A:
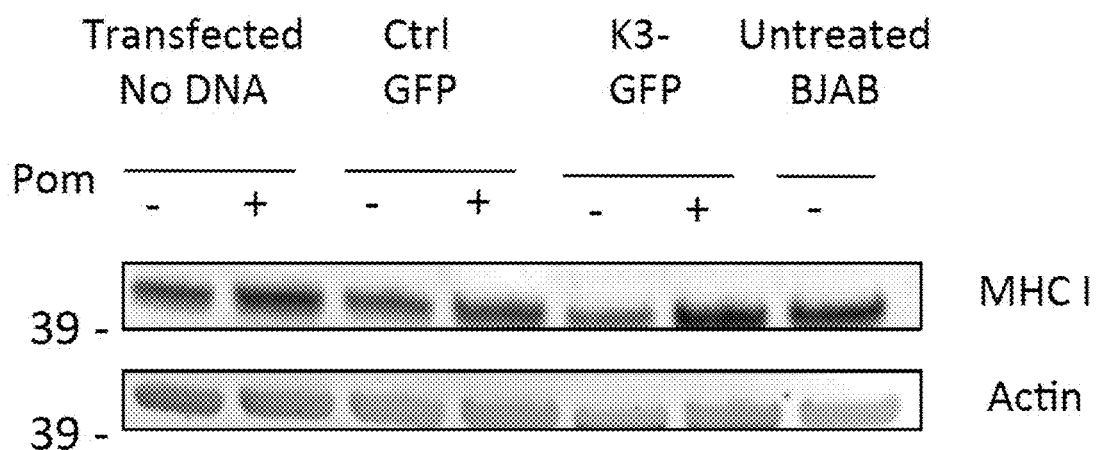
FIGS. 9A-9C show K3-transfected KSHV-negative BJAB cells treated with pomalidomide and prevention of K3/K5 mediated MHC-1 down-regulation.
Figure 9B:
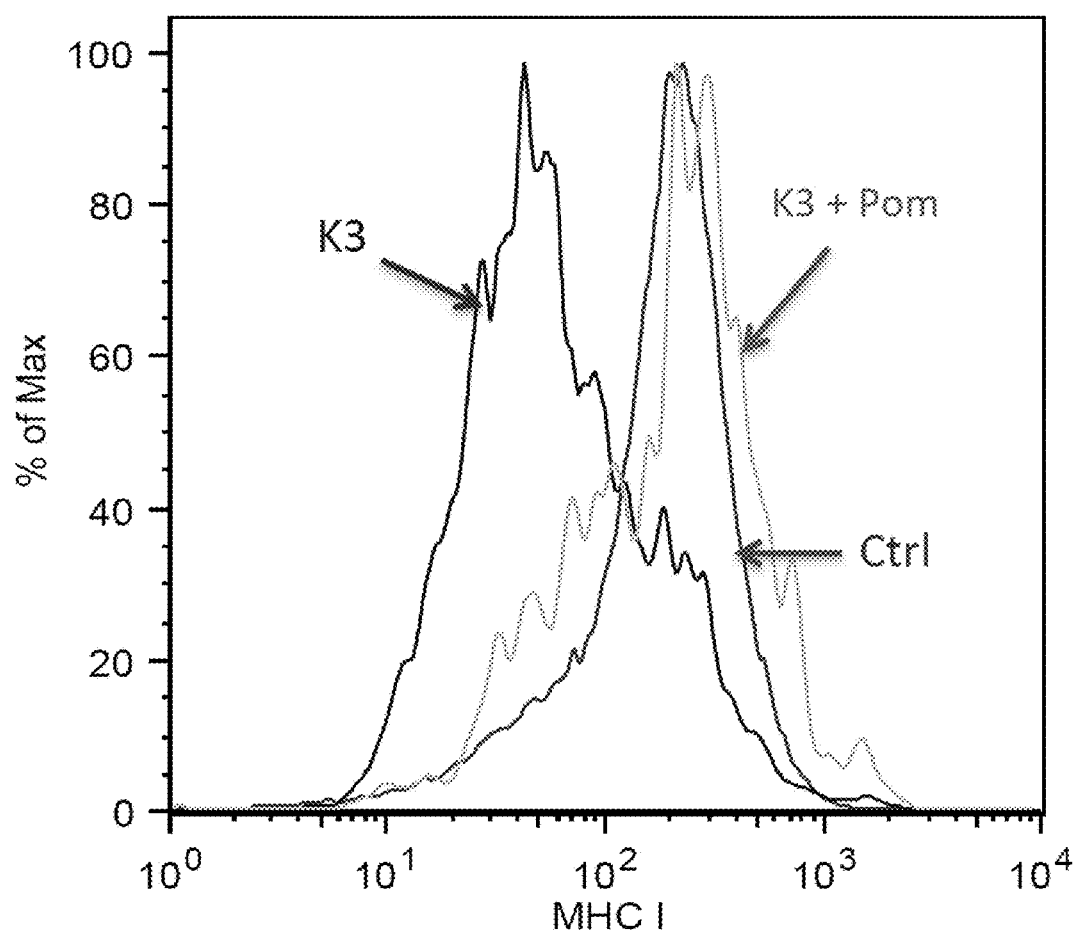
Figure 9C:
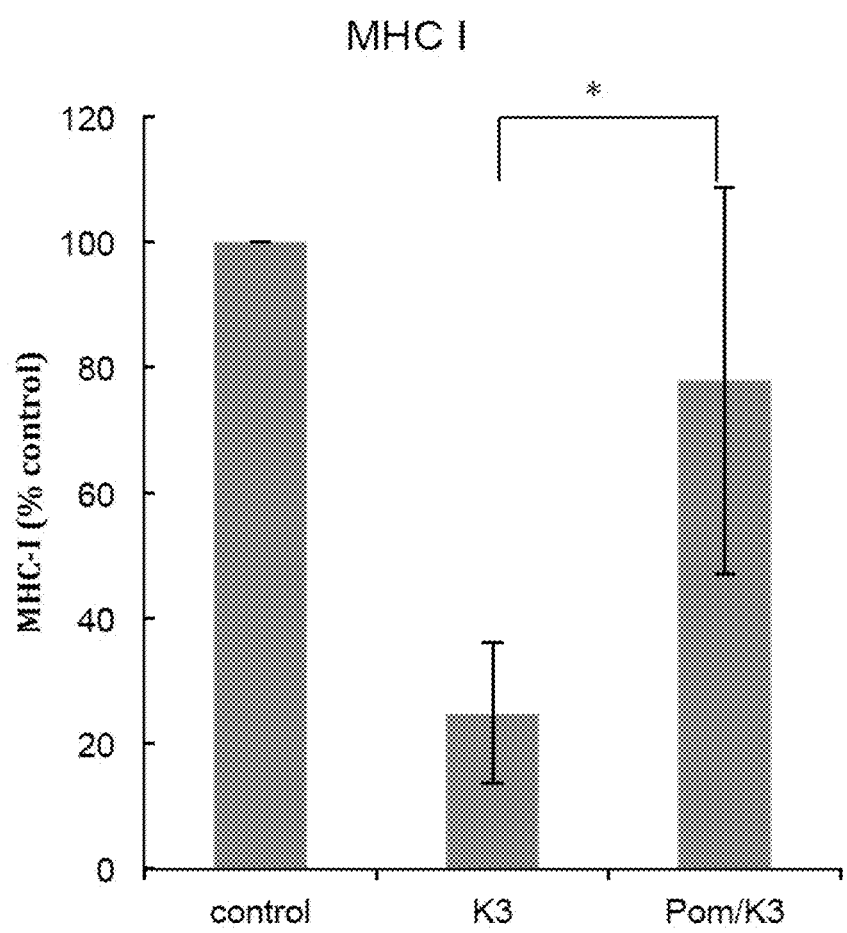
Figure 9D:
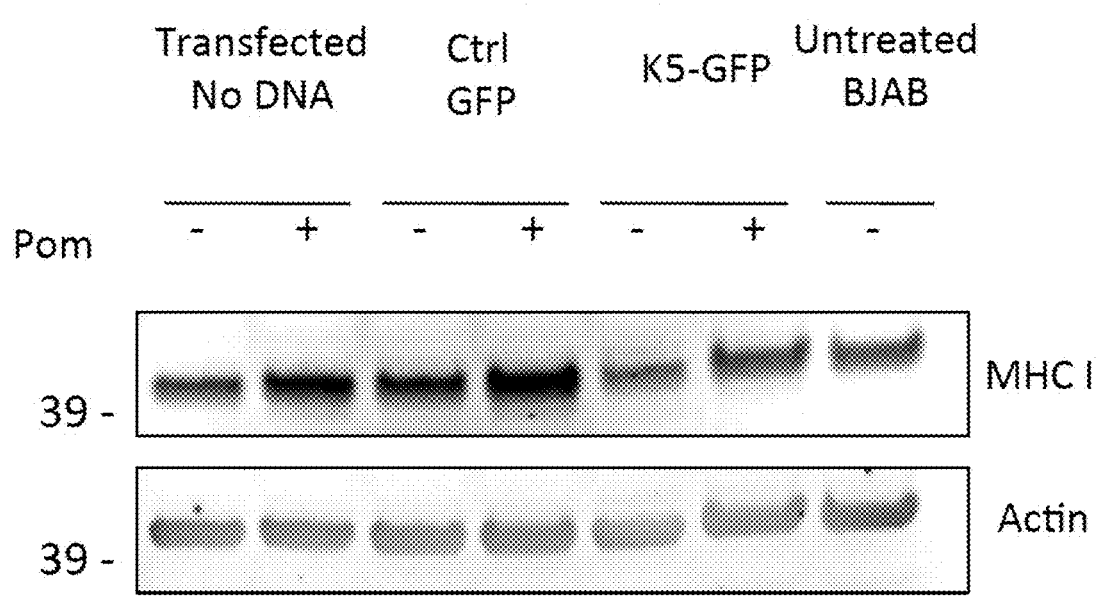
FIGS. 9D-9F show K3-transfected KSHV-negative BJAB cells treated with pomalidomide and prevention of K3/K5 mediated MHC-1 down-regulation.
Figure 9E:
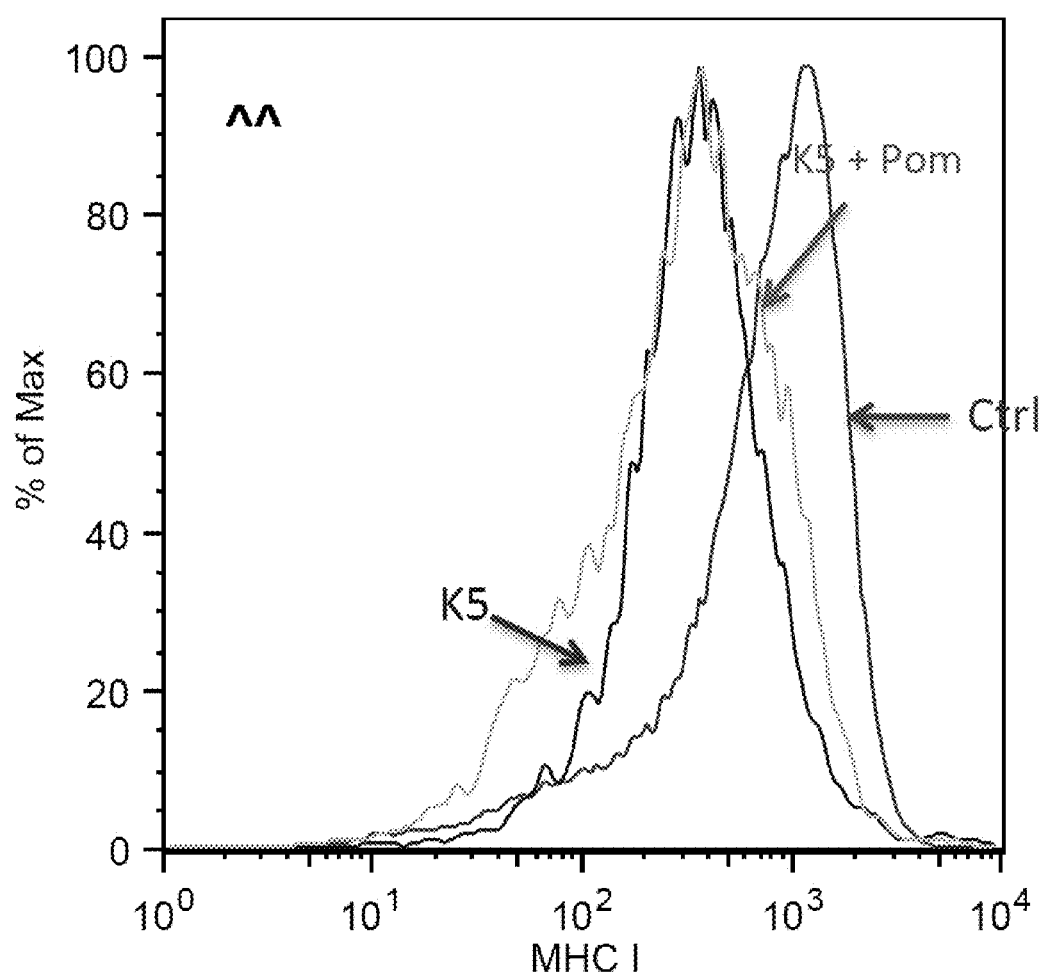
Figure 9F:
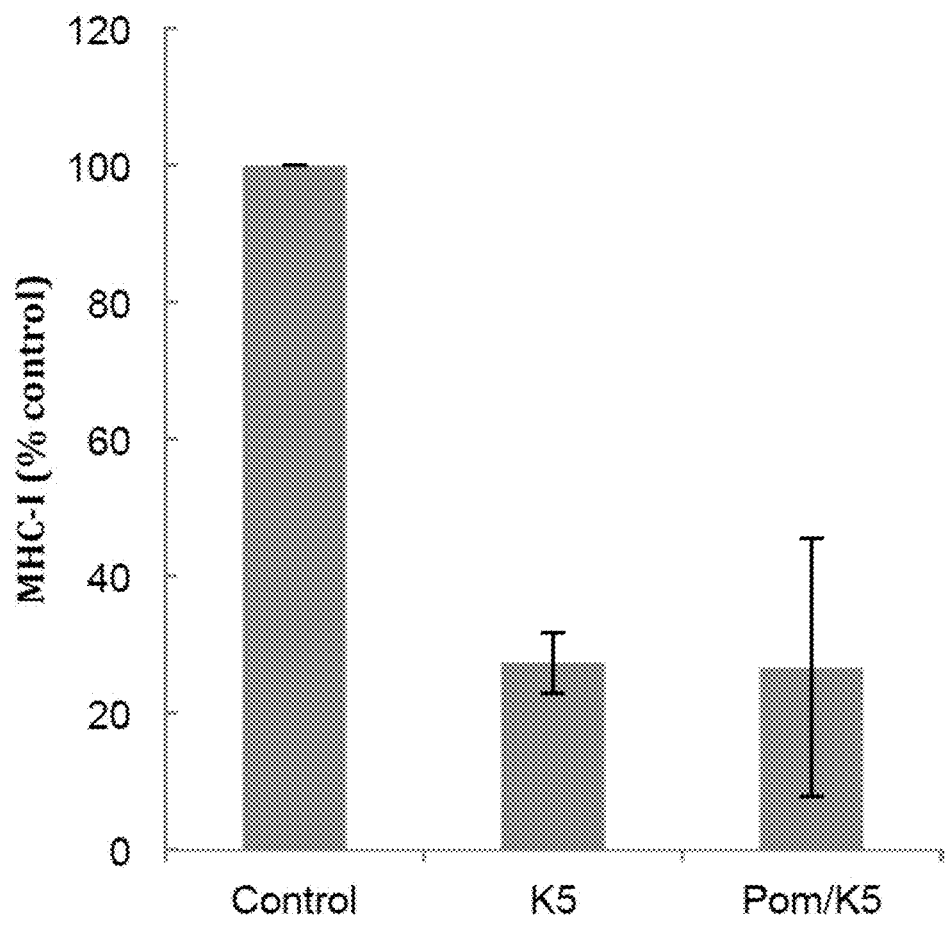

Immunomodulatory drugs treatment increased p21: The tumor suppressor p21 is a cell cycle inhibitor and is known to be down-regulated in cancers to promote cellular proliferation. Cells were treated at 10 ii M for 72 hours and p21 levels were measured. FIGS. 6A-6B. Pomalidomide was most effective in up-regulating p21 compared to thalidomide and lenalidomide. These changes coincided with a decrease in cellular proliferation and an increase in cell death.

Pomalidomide inhibited MHC-1 Down-Regulation but did not prevent K3 and K5 expression: KSHV Lytic proteins K3 and K5 are ubiquitin ligases that down-regulate MHC-I as a means of viral immune evasion. Pretreatment with the immunomodulatory drugs prevented the down-regulation of MHC Class I expression that normally occurs upon lytic KSHV activation. Pomalidomide was substantially more effective at preventing the down-regulation of MEW Class I expression compared to lenalidomide and thalidomide. See FIGS. 7A-7C and FIG. 8. Pomalidomide did not significantly change the protein expression level of KSHV K3 or K5, suggesting it was interfering with their effects on MHC-1 rather than inhibiting their production following lytic activation.

Additionally, BJAB cells transfected with plasmids encoding K3 or K5 led to down-regulation of MHC-1 that could also be prevented by pretreating cells with pomalidomide. FIGS. 9A-9E. BJAB cells were treated with 10 μM Pomalidomide (Pom) for 48 hours, and then electroporated with GFP-tagged K3 or K5 plasmids (or GFP controls). 24 hours after electroporation, FACS analysis was done using half of the cells. FACS peaks showed MHC I expression in GFP-positive cells. The remaining cells were subjected to lysis, protein extraction, and western blot. Blots were probed with antibodies to the indicated proteins. While western blots showed Pomalidomide preventing MHC I knockdown, this was not consistently observed by FACS analysis with K5. These data suggest that these drugs could be a potential treatment for primary effusion lymphoma and possibly other KSHV-induced cancers.

28 Day Cycle of Pomalidomide in Combination with Doxorubicin in Patients with Advanced Kaposi's Sarcoma Provided herein is a clinical trial protocol to investigate the effects of pomalidomide in combination with doxorubicin in patients with advanced Kaposi's sarcoma.

Enrollment eligibility criteria: Patients with biopsy proven (confirmed in the laboratory of pathology, CCR) Kaposi's sarcoma (KS). Patients can meet eligibility criteria of either Group I or Group II as following:

Group I: KS that requires systemic therapy (no prior therapy required). This includes (i) KS on skin sufficiently widespread that it is not amenable to local therapy, or T1 KS or KS affecting quality of life due to local symptoms or psychological distress, (ii) KS patients with an inadequate response to pomalidomide (either progressive disease or stable disease after 4 months), and (iii) KS patients with an inadequate response to liposomal doxorubicin (either progressive disease or stable disease after 6 cycles) or other systemic chemotherapy (either progressive disease or stable disease after 6 cycles). Group I excludes patients eligible for Group II. A wash out period off treatment of 3 weeks is required, except in the case of patients with progressive disease.

Group II: KS in one of the following high-risk groups (no prior therapy required): (i) concurrent KSHV-associated multicentric Castleman's disease (MCD), or (ii) KSHV Inflammatory Cytokine Syndrome (KICS), including those also meeting clinical criteria for KS immune reconstitution syndrome (KS IRIS). Patients with primary effusion lymphoma or a large cell lymphoma arising in KSHV-associated MCD are excluded.

Patients can be HIV positive or negative. All HIV positive patients must be willing to be compliant with highly active antiretroviral therapy (HAART). HIV positive patients of Groups I are on HAART for 1 month with stable disease and there is no minimum time restriction with progressive disease. For HIV positive patient of Group II, there is no minimum time restriction on prior HAART and patients may be HAART naive.

Study Design: Patients receive pomalidomide once a day consecutively on days 1-21 of a 28-day cycle, at the dose levels described below in Table 5, combined with liposomal doxorubicin IV on day 1 of the 21-day cycle, at the dose levels described below in Table 6. All patients receive thromboprophylaxis, generally with aspirin 81 mg tablet daily. Pegfilgrastim is given 24 h after the end of liposomal doxorubicin as secondary prophylaxis for participants who develop Grade 3 or worse neutropenia on study.

Dose escalation design: The study starts by enrolling 3 patients into each of two groups of patients (Group I and Group II), each receives the drug combination starting on dose level 1.

If 1 dose limiting toxicity (DLT) in the first 3 patients is noted in either cohort, that cohort is expanded to 3 additional patients at that dose level. If 0/3 or 1/6 DLT occur in a Group at a particular dose, the dosing in that Group increases to the next dose level. Dose escalation for each cohort stops when 2 or more DLTs occur (in a cohort of 3 or 6 patients). If dose escalation proceeds to DL3, 6 patients are treated at this dose (unless 2 DLT occur before that time). If 2 or more DLTs occur at dose level 1 in either cohort, that cohort dose de-escalates to DL-1.

Liposomal doxorubicin dosing begins at 20 mg, but dosing is adjusted every 4 weeks rather than every three weeks. This schedule slightly decreases the dose intensity of doxsorubicin. The optional 4th dose level evaluates a combination of de-escalated liposomal doxorubicin in combination with pomalidomide to determine safety and tolerability for at least 6 to 12 months in patients with KS.

TABLE 6

| Dose level | Pomalidomide (mg) | Liposomal doxorubicin (mg/m$^2$) |
| --- | --- | --- |
| −1 | 2 | 15 |
| 1 | 2 | 20 |
| 2 | 3 | 20 |
| 3 | 5 | 20 |
| 4 (optional) | 5 | 10 |

Dose limiting toxicity includes any Grade 4 Toxicity (CTACE v4.0) that is at least possibly attributable to pomalidomide or liposomal doxorubicin and unlikely attributable to HIV, its therapy or manifestations of KSHV-associated malignancy, and any Grade 3 adverse event (CTCAE v4.0) possibly, probably, definitely attributed to pomalidomide or liposomal doxorubicin, excluding certain specific adverse effects.

In patients with pulmonary KS, pulmonary function is evaluated every 3 cycles and after the last cycle administered. Subjects with residual PFT abnormalities are further evaluated on this schedule until PFTs are normal or there is a plateau in improvement. Pulmonary function tests include spirometry, lung volumes evaluation and quantification of diffuse capacity for carbon monoxide (DLCO). PFTs are a helpful tool to diagnose restrictive, obstructive and interstitial pulmonary disorders. They are also useful in assessing severity, monitoring response to therapeutic interventions and screening for lung pathologies.

HIV infected subjects must be receiving and adherent to, HAART.

Complete Response: is measured by the absence of any detectable residual disease, including tumor associated edema, persisting for at least 4 weeks. Patients with KS may have residual pigmented macular skin lesions persisting after apparent complete response; for such patients a biopsy of at least one representative lesion is required to document the absence of malignant cells. If a lesion has not been biopsied, the patient may be classified as having a clinical CR. It should be noted that since KSHV can infect cells other than KS spindle cells, the existence of occasional cells (not spindle cells) infected with KSHV in the biopsy does not necessarily indicate the presence of continued KS. CR will be based on histologic and IHC features only, PCR to evaluate for KSHV DNA will not be used indetermination.

For subjects with visceral disease, the diagnostic radiologic or endoscopic study should be repeated if not medically contraindicated and found to be negative for evidence of disease. If such procedures are medically contraindicated but the patient has no clinical evidence of visceral disease, the patient may be classified as having a clinical CR.

Clinical Complete Response is measured by the absence of any detectable residual disease, including tumor associated edema, persisting for at least 4 weeks. For subjects with pigmented macular skin lesions persisting after apparent complete response, if a representative lesion has not been biopsied.

For subjects with visceral disease, the diagnostic radiologic or endoscopic study should be repeated if not medically contraindicated and found to be negative for evidence of disease. If such procedures are medically contraindicated but the patient has no clinical evidence of visceral disease, the patient may be classified as having a clinical CR.

Partial Response is measured by no progressive disease (see below and noting, that single lesions which split up into 2 or more smaller lesions during the course of treatment will still be counted as one); no new lesions occurring in previously uninvolved areas of the body; no new visceral sites of involvement or the appearance or worsening of tumor-associated edema or effusions and: a 50% or greater decrease in the number and/or size of previously existing lesions lasting for at least 4 weeks or Complete flattening of at least 50% of all previously raised lesions (i.e., 50% of all previously nodular or plaque-like lesions become macular) lasting for at least 4 weeks or a 50% decrease in radiologically measurable visceral lesions sustained without evidence of regrowth for at least 4 weeks or a 50% decrease in radiologically measurable visceral lesions sustained without evidence of regrowth for at least 4 weeks or subjects who otherwise meet the criteria for a CR but still have residual tumor-associated edema or effusions will be classified as having a PR.

Progressive Disease is measured for those criteria that involve measurement of lesions in the clinic, the designation of progression should be made, when feasible, only when the criteria below have been met in two measurements spaced at least 1 week apart. For the assignment of progressive disease for the primary outcome analysis, progression will be defined in comparison to baseline measurements. An increase of 25% or more over baseline in the number of lesions and/or the size (sum of the products of the largest perpendicular diameters) of the marker lesions or a change in character from macular to plaque-like or nodular of at least 25% of the lesions or new visceral sites of involvement or progression of visceral disease or The development of new or increasing tumor-associated edema or effusion that lasts at least 1 week and interferes with the patient's normal activities.

Stable Disease is any tumor measurement not meeting the criteria for Complete Response, Partial Response, or Progressive Disease.

Overall Response is measured as the sum of complete responses, clinical complete responses, and partial responses.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the embodiments and are encompassed by the appended claims.

What is claimed is:

1. A method of treating or managing Kaposi's sarcoma-associated herpesvirus (KSHV) induced lymphoma, comprising:
   identifying a patient having KSHV-induced lymphoma sensitive to treatment with a compound of the formula:

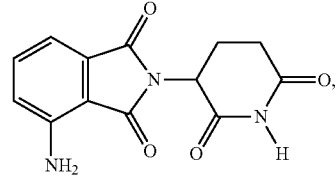 [SMILES: Nc1cccc2c1C(=O)N(C1CCC(=O)NC1=O)C2=O]

or a pharmaceutically acceptable salt, solvate or stereoisomer thereof;
   wherein said identifying comprises measuring a level of major histocompatibility complex class I (MHC-1) in a biological sample obtained from the patient, wherein a decreased level of MHC-1 relative to a control sample indicates a likelihood that the patient is sensitive to treatment with the compound; and
   (ii) administering to the patient a therapeutically effective amount of the compound in a 28 day cycle comprising 21 consecutive days of administration followed by seven consecutive days of rest.

2. The method of claim 1, wherein the KSHV-induced lymphoma is a B-cell lymphoma.

3. The method of claim 2, wherein the B-cell lymphoma is primary effusion lymphoma (PEL).

4. The method of claim 1, wherein KSHV-induced lymphoma is multicentric Castleman's disease (MCD).

5. The method of claim 1, wherein the patient is human immunodeficiency virus (HIV) positive.

6. The method of claim 1, wherein the KSHV-induced lymphoma is newly diagnosed, relapsed, refractory, or relapsed and refractory.

7. The method of claim 1, wherein the patient has received previous therapy for KSHV-induced lymphoma.

8. The method of claim 7, wherein the previous therapy is treatment with cytotoxic chemotherapy, treatment with radiation therapy, treatment with an immunomodulatory compound, treatment with interferon, or treatment with local therapy.

9. The method of claim 8, wherein the previous therapy is treatment with thalidomide, lenalidomide, or a combination thereof.

10. The method of claim 1, wherein the compound is administered in an amount of about 1, 2, 3, 4, or 5 mg per day.

11. The method of claim 1, wherein the compound is administered as a free base.

12. The method of claim 1, wherein the compound is administered orally.

13. The method of claim 12, wherein the compound is administered in a capsule or tablet.

14. The method of claim 1, which further comprises administering a therapeutically effective amount of an additional active agent, wherein the additional active agent is doxorubicin, a PD-1 inhibitor, a PD-L1 inhibitor, or a CTLA-4 inhibitor.

15. The method of claim 14, wherein the additional active agent is a PD-1 inhibitor or a PD-L1 inhibitor.

16. The method of claim 15, wherein the PD-1 inhibitor is nivolumab, pembrolizumab, pidilizumab, REGN2810, PDR 001, AMP-224, or MEDI0680.

17. The method of claim 15, wherein the PD-L1 inhibitor is durvalumab, avelumab, atezolizumab, or BMS-936559.

18. The method of claim 3, wherein the patient is human immunodeficiency virus (HIV) positive.

19. The method of claim 3, wherein the patient has received previous treatment with cytotoxic chemotherapy, radiation therapy, an immunomodulatory compound, interferon, or local therapy.

20. The method of claim 19, wherein the previous therapy is treatment with thalidomide, lenalidomide, or a combination thereof.

21. The method of claim 3, wherein the compound is administered in an amount of about 1, 2, 3, 4, or 5 mg per day.

22. The method of claim 21, wherein the compound is administered as a free base.

23. The method of claim 21, wherein the compound is administered orally.

24. The method of claim 23, wherein the compound is administered in a capsule or tablet.

25. The method of claim 3, wherein the compound is orally administered in an amount of 5 mg per day for 21 consecutive days followed by seven consecutive days of rest in a 28 day cycle.

26. The method of claim 3, which further comprises administering a therapeutically effective amount of an additional active agent, wherein the additional active agent is doxorubicin, a PD-1 inhibitor, a PD-L1 inhibitor, or a CTLA-4 inhibitor.

27. The method of claim 26, wherein the additional active agent is a PD-1 inhibitor or a PD-L1 inhibitor.

28. The method of claim 27, wherein the PD-1 inhibitor is nivolumab, pembrolizumab, pidilizumab, REGN2810, PDR 001, AMP-224, or MEDI0680.

29. The method of claim 27, wherein the PD-L1 inhibitor is durvalumab, avelumab, atezolizumab, or BMS-936559.

* * * * *